(12) United States Patent
Pulapura et al.

(10) Patent No.: US 10,939,901 B2
(45) Date of Patent: Mar. 9, 2021

(54) CUSTOMIZABLE ANCHORAGE DEVICES AND METHODS OF USE

(71) Applicant: TYRX, Inc., Monmouth Junction, NJ (US)

(72) Inventors: Satish Pulapura, Bridgewater, NJ (US); Fatima Buevich, Highland Park, NJ (US); Archana Rajaram, Monmouth Junction, NJ (US); Jonathan M. Mahoney, Fanwood, NJ (US); Dan Thanh Le, Franklin Park, NJ (US)

(73) Assignee: MEDTRONIC, INC., Minneapolis, MN (US)

( * ) Notice: Subject to any disclaimer, the term of this patent is extended or adjusted under 35 U.S.C. 154(b) by 143 days.

(21) Appl. No.: 15/583,153

(22) Filed: May 1, 2017

(65) Prior Publication Data
US 2017/0319193 A1    Nov. 9, 2017

Related U.S. Application Data

(60) Provisional application No. 62/331,675, filed on May 4, 2016.

(51) Int. Cl.
*A61B 17/04* (2006.01)
*A61L 31/14* (2006.01)
(Continued)

(52) U.S. Cl.
CPC .......... *A61B 17/0401* (2013.01); *A61L 31/04* (2013.01); *A61L 31/10* (2013.01);
(Continued)

(58) Field of Classification Search
CPC ...... A61L 31/16; A61L 31/148; A61L 31/146; A61L 31/10; A61L 31/04; C08G 63/02; A61B 17/0401; A61F 13/02
(Continued)

(56) References Cited

U.S. PATENT DOCUMENTS

| 4,600,001 | A  | * | 7/1986 | Gilman | ................. A61F 13/023 |
|           |    |   |        |        | 602/52 |
| 2002/0019602 | A1 | * | 2/2002 | Geng   | ................ A61F 13/00063 |
|           |    |   |        |        | 602/42 |

(Continued)

OTHER PUBLICATIONS

Documents mailed from International Searching Authority—EPO, European Patent Office, P.B. 5818 Patentlaan 2, NL-2280 HV Rijswijk, in International Application No. PCT/US2017/030530—PCT/ISA/220—Notification of Transmittal of the International Search Report and the Written Opinion of the International Searching Authority, or the Declaration; PCT/ISA/210 International Search Report, Form PCT/ISA/237 Written Opinion of the International Searching Authority (European Patent Office).
(Continued)

*Primary Examiner* — George J Ulsh
*Assistant Examiner* — Andrew P. Restaino
(74) *Attorney, Agent, or Firm* — Sorell, Lenna & Schmidt, LLP

(57) ABSTRACT

An anchorage device includes a substrate extending along a longitudinal axis between a first end having a first bonding area and an opposite second end having a second bonding area. The substrate has a third bonding area between the first and second bonding areas. Kits, systems and methods are disclosed.

19 Claims, 37 Drawing Sheets

(51) Int. Cl.
*A61L 31/16* (2006.01)
*A61L 31/10* (2006.01)
*A61L 31/04* (2006.01)
*C08G 63/02* (2006.01)

(52) U.S. Cl.
CPC ........... *A61L 31/146* (2013.01); *A61L 31/148* (2013.01); *A61L 31/16* (2013.01); *C08G 63/02* (2013.01); *A61B 2017/0409* (2013.01); *A61B 2017/0446* (2013.01)

(58) Field of Classification Search
USPC ...................................... 623/23.72
See application file for complete search history.

(56) References Cited

U.S. PATENT DOCUMENTS

| | | | |
|---|---|---|---|
| 2002/0170918 A1* | 11/2002 | Solovay | A61F 15/002 221/73 |
| 2005/0033215 A1* | 2/2005 | Lebner | A61B 17/085 602/54 |
| 2005/0226916 A1* | 10/2005 | Cochrum | A61L 15/225 424/445 |
| 2008/0138387 A1 | 6/2008 | Machiraju | |
| 2008/0241212 A1 | 10/2008 | Moses et al. | |
| 2010/0268198 A1* | 10/2010 | Buan | A61F 13/0206 604/543 |
| 2013/0150796 A1* | 6/2013 | Souza | A61M 25/02 604/180 |
| 2013/0184722 A1* | 7/2013 | Stopek | B32B 9/047 606/151 |
| 2014/0031912 A1* | 1/2014 | McJames | A61L 31/10 607/120 |
| 2014/0343673 A1* | 11/2014 | Matheny | A61L 31/005 623/3.29 |
| 2016/0030247 A1* | 2/2016 | Salvino | A61L 15/44 604/290 |
| 2016/0045634 A1* | 2/2016 | Williams | A61F 13/0236 604/307 |

OTHER PUBLICATIONS

PCT/US2017/030530 International Preliminary Report on Patentability Chapter I mailed from WIPO dated Nov. 15, 2018 and Written Opinion of the International Searching Authority—European Patent Office.
N. Coker, et al. "Tranexamic acid applied topically to achieve haemostasis," Anaesthesia, vol. 55, No. 6, Jun. 15, 2000, pp. 600-601.
International Search Report of the International Searching Authority(ISA/EPO) dated Aug. 1, 2017 of International PCT Application No. PCT/US2017/030510 filed on May 2, 2017.
International Search Report of the International Searching Authority(ISA/EPO) dated Aug. 3, 2017 of International PCT Application No. PCT/US2017/030513 filed on May 2, 2017.
International Search Report of the International Searching Authority(ISA/EPO) dated Aug. 10, 2017 of International PCT Application No. PCT/US2017/030517 filed on May 2, 2017.
International Search Report of the International Searching Authority(ISA/EPO) dated Aug. 3, 2017 of International PCT Application No. PCT/US2017/030504 filed on May 2, 2017.
European Patent Office, Patentlaan 2, 2288 EE Rijswijk, Netherlands, Communication from the Examining Division, Application No. 1772307.1 dated Nov. 17, 2020, response due within 4 months.
European Patent Office, Patentlaan 2, 2288 EE Rijswijk, Netherlands, Communication from the Examining Division, Application No. 17726393.6 dated Oct. 28, 2020, response due within 4 months.
European Patent Office, Patentlaan 2, 2288 EE Rijswijk, Netherlands, Communication from the Examining Division, Application No. 17723206.3 dated Oct. 28, 2020, response due within 4 months.

* cited by examiner

| # | MATERIAL | ABSORPTION RATING | COMMENTS | |
|---|---|---|---|---|
| 1 | SURGIFOAM | 5 | FASTER THAN JELLO |  |
| 2 | CHITOSAN FILM | 1 | WITHIN 1-2 SEC |  |
| 3 | CHITOSAN + MESH | 4 | WITHIN 3 MIN |  |
| 4 | PVP + MESH | 2 | WITHIN 3 MIN | 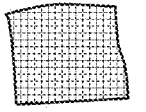 |
| 6 | PEG + MESH | 3 | WITHIN 3 MIN | 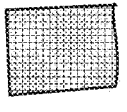 |
| 7 | JELLO | 6 | SEVERAL HOURS |  |
| 5 | CHITOSAN + PVP + MESH | | LONGER THAN 3 MIN BUT FASTER THAN SURGIFOAM, MAY BE WAS DRYER THAN OTHER SAMPLES | |
FIG. 12

| PREPARED SAMPLES OF ORC AND GLYCOPRENE | | | BEFORE IMMERSION | BEFORE INCUBATION | AFTER INCUBATION 48 H | AFTER INCUBATION 48 H, BUFFER DECANTED |
|---|---|---|---|---|---|---|
| GROUP 1 | SAMPLE | DESCRIPTION | | | | |
| A | 1, 2 | GLYCOPRENE & TYRC-COATED ORC |  | 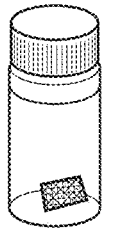 | 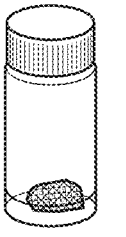 | 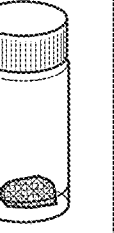 |
| B | 3, 4 | TYRX-COATED GLYCOPRENE & ORC |  | 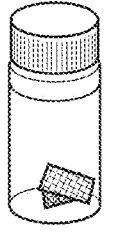 | 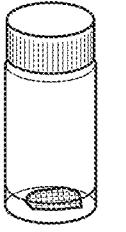 |  |
| C | 5, 6 | TYRX-COATED GLYCOPRENE & TYRX-COATED ORC |  | 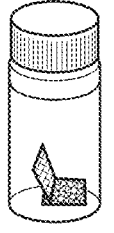 | 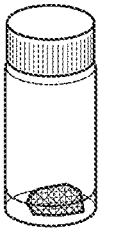 |  |
| D | 9, 10 | TYRX-COATED ORC |  | 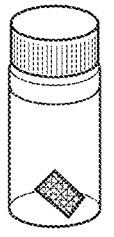 | 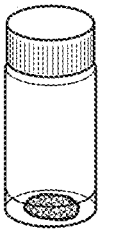 |  |
| E | 11, 12 | TYRX-COATED GLYCOPRENE |  | 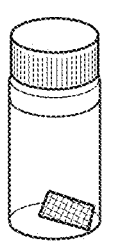 | 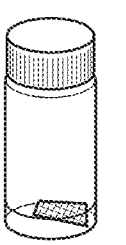 | 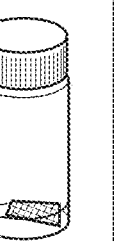 |
*FIG. 17*

EXPECTED TOTAL DRUG CONTENT OF EACH SAMPLE

| | WEIGHT (mG) | | DRUG FROM COATED ORC | | DRUG FROM COATED GLYCO | | TOTAL DRUG | |
|---|---|---|---|---|---|---|---|---|
| SAMPLE | COATED ORC | COATED GLYCOPRENE | EPI+MINO | RIF | EPI+MINO | RIF | EPI+MINO | RIF |
| 1 | 60.4 | 0 | 6633476 | 8297348 | 0 | 0 | 6633476 | 8297348 |
| 2 | 57.7 | 0 | 6336946 | 7926440 | 0 | 0 | 6336946 | 7926440 |
| 3 | 0 | 14.4 | 0 | 0 | 4009884 | 3789638 | 4009884 | 3789638 |
| 4 | 0 | 14.9 | 0 | 0 | 4149117 | 3921223 | 4149117 | 3921223 |
| 5 | 63.6 | 14.7 | 6984918 | 8736942 | 4093424 | 3868589 | 11078342 | 12605531 |
| 6 | 59.1 | 13.3 | 6490702 | 8118962 | 3703574 | 3500152 | 10194276 | 11618914 |

| | | | | | | | | |
|---|---|---|---|---|---|---|---|---|
| 9 | 49.3 | 0 | 5414410 | 6772504 | 0 | 0 | 5414410 | 6772504 |
| 10 | 53.2 | 0 | 5842730 | 7308260 | 0 | 0 | 5842730 | 7308260 |
| 11 | 0 | 10.3 | 0 | 0 | 2868181 | 2710644 | 2868181 | 2710644 |
| 12 | 0 | 11.5 | 0 | 0 | 3202338 | 3026447 | 3202338 | 3026447 |

100% OF DRUG IN SAMPLE

"MINO" REFERS TO MINOCYCLINE, "RIF" REFERS TO RIFAMPIN AND "EPI" REFERS TO EPINEPHRINE.

*FIG. 19F*

ELUTION RESULTS

| GLYCOPRENE & TYRX-COATED ORC | | PEAK AREA | | | CONCENTRATION = RF*AREA | | | TOTAL DRUG AT TIMEPT | | | TOTAL DRUG OVER TIME | | | % DRUG RELEASE OVER TIME | | |
|---|---|---|---|---|---|---|---|---|---|---|---|---|---|---|---|---|
| SAMPLE | PBS VOLUME (mL) | TIME | EPI+MINO | MINO | RIF | EPI+MINO | RIF | | EPI+MINO | RIF | | EPI+MINO | RIF | | EPI+MIN | RIF | MINO | RIF |
| 1 | 0 | 0 | 0 | 0 | 0 | 0 | 0 | | 0 | 0 | | 0 | 0 | | 0% | 0% | 0% | 0% |
| | 20 | 2 | 19137 | 31015 | 14038 | 50152 | 14038 | | 1003040 | 280760 | | 1003040 | 280760 | | 15% | 3% | 16% | 4% |
| | 10 | 4 | 41620 | 51945 | 36992 | 93565 | 36992 | | 935650 | 369920 | | 1938690 | 650680 | | 29% | 8% | 30% | 8% |
| | 5 | 6 | 124225 | 140802 | 146848 | 265027 | 146848 | | 1325135 | 734240 | | 3263825 | 1384920 | | 49% | 17% | 51% | 17% |
| | 2 | 26 | 268006 | 392109 | 332954 | 660115 | 332954 | | 1320230 | 665908 | | 4584055 | 2050828 | | 69% | 25% | 70% | 25% |
| | 2 | 30 | 660873 | 839769 | 2029683 | 1500642 | 2029683 | | 3001284 | 4059366 | | 7585339 | 6110194 | | 114% | 74% | 116% | 75% |
| 2 | 0 | 0 | 0 | 0 | 0 | 0 | 0 | | 0 | 0 | | 0 | 0 | | 0% | 0% | 0% | 0% |
| | 20 | 2 | 20678 | 33248 | 14715 | 53926 | 14715 | | 1078520 | 294300 | | 1078520 | 294300 | | 17% | 4% | 17% | 4% |
| | 10 | 4 | 41300 | 50426 | 37316 | 91726 | 37316 | | 917260 | 373160 | | 1995780 | 667460 | | 31% | 8% | 30% | 8% |
| | 5 | 6 | 122306 | 138199 | 132796 | 260505 | 132796 | | 1302525 | 663980 | | 3298305 | 1331440 | | 52% | 17% | 51% | 17% |
| | 2 | 26 | 245110 | 364796 | 313035 | 609906 | 313035 | | 1219812 | 626070 | | 4518117 | 1957510 | | 71% | 25% | 70% | 25% |
| | 2 | 30 | 659586 | 828742 | 2022220 | 1488328 | 2022220 | | 2976656 | 4044440 | | 7494773 | 6001950 | | 118% | 76% | 116% | 75% |

FIG. 19G

ELUTION RESULTS

| TYRX-COATED GLYCOPRENE & ORC | | PEAK AREA | | | CONCENTRATION = RF*AREA | | TOTAL DRUG AT TIMEPT | | TOTAL DRUG OVER TIME | | % DRUG RELEASE OVER TIME | | |
|---|---|---|---|---|---|---|---|---|---|---|---|---|---|
| SAMPLE | PBS VOLUME (mL) | TIME | EPI+MINO | MINO | RIF | EPI+MINO | RIF | EPI+MINO | RIF | EPI+MINO | RIF | EPI+MIN | RIF | MINO | RIF |
| 3 | 0 | 0 | 0 | 0 | 0 | 0 | 0 | 0 | 0 | 0 | 0 | 0% | 0% | 0% | 0% |
|  | 20 | 2 | 17879 | 41181 | 48747 | 59060 | 48747 | 1181200 | 974940 | 1181200 | 974940 | 29% | 26% | 28% | 24% |
|  | 10 | 4 | 57269 | 104342 | 143275 | 161611 | 143275 | 1616110 | 1432750 | 2797310 | 2407690 | 70% | 64% | 73% | 66% |
|  | 5 | 6 | 37537 | 52912 | 87956 | 90499 | 87956 | 452495 | 439780 | 3249805 | 2847470 | 81% | 75% | 85% | 79% |
|  | 2 | 26 | 34921 | 59446 | 69479 | 94367 | 69479 | 188734 | 138958 | 3438539 | 2986428 | 86% | 79% | 89% | 82% |
|  | 2 | 30 | 48834 | 67577 | 153374 | 116411 | 153374 | 232822 | 306748 | 3671361 | 3293176 | 92% | 87% | 96% | 91% |
| 4 | 0 | 0 | 0 | 0 | 0 | 0 | 0 | 0 | 0 | 0 | 0 | 0% | 0% |  |  |
|  | 20 | 2 | 16404 | 37152 | 43346 | 53556 | 43346 | 1071120 | 866920 | 1071120 | 866920 | 26% | 22% |  |  |
|  | 10 | 4 | 73490 | 133950 | 184024 | 207440 | 184024 | 2074400 | 1840240 | 3145520 | 2707160 | 76% | 69% |  |  |
|  | 5 | 6 | 46933 | 68490 | 114634 | 115423 | 114634 | 577115 | 573170 | 3722635 | 3280330 | 90% | 84% |  |  |
|  | 2 | 26 | 16324 | 32107 | 29531 | 48431 | 29531 | 96862 | 59062 | 3819497 | 3339392 | 92% | 85% |  |  |
|  | 2 | 30 | 67255 | 89185 | 195597 | 156440 | 195597 | 312880 | 391194 | 4132377 | 3730586 | 100% | 95% |  |  |

*FIG. 19H*

ELUTION RESULTS

| TYRX-COATED GLYCOPRENE & TYRX-COATED ORC | | | PEAK AREA | | | CONCENTRATION = RF*AREA | | | TOTAL DRUG AT TIMEPT | | | TOTAL DRUG OVER TIME | | | % DRUG RELEASE OVER TIME | | |
|---|---|---|---|---|---|---|---|---|---|---|---|---|---|---|---|---|---|
| SAMPLE | PBS VOLUME (mL) | TIME | EPI+MINO | MINO | RIF | EPI+MINO | RIF | | EPI+MINO | RIF | | EPI+MINO | RIF | | EPI+MIN | RIF | MINO | RIF |
| 5 | 0 | 0 | 0 | 0 | 0 | 0 | 0 | | 0 | 0 | | 0 | 0 | | 0% | 0% | 0% | 0% |
|  | 20 | 2 | 35510 | 69016 | 57751 | 104526 | 57751 | | 2090520 | 1155020 | | 2090520 | 1155020 | | 19% | 9% | 24% | 11% |
|  | 10 | 4 | 85401 | 133154 | 146594 | 218555 | 146594 | | 2185550 | 1465940 | | 4276070 | 2620960 | | 39% | 21% | 45% | 24% |
|  | 5 | 6 | 166903 | 210876 | 225697 | 377779 | 225697 | | 1888895 | 1128485 | | 6164965 | 3749445 | | 56% | 30% | 64% | 34% |
|  | 2 | 26 | 107557 | 223674 | 142872 | 331231 | 142872 | | 662462 | 285744 | | 6827427 | 4035189 | | 62% | 32% | 81% | 44% |
|  | 2 | 30 | 904673 | 1136696 | 2179775 | 2041369 | 2179775 | | 4082738 | 4359550 | | 10910165 | 8394739 | | 98% | 67% | 109% | 74% |
| 6 | 0 | 0 | 0 | 0 | 0 | 0 | 0 | | 0 | 0 | | 0 | 0 | | 0% | 0% | | |
|  | 20 | 2 | 51925 | 93395 | 73989 | 145320 | 73989 | | 2906400 | 1479780 | | 2906400 | 1479780 | | 29% | 13% | | |
|  | 10 | 4 | 93036 | 143471 | 161113 | 236507 | 161113 | | 2365070 | 1611130 | | 5271470 | 3090910 | | 52% | 27% | | |
|  | 5 | 6 | 190265 | 231814 | 283505 | 422079 | 283505 | | 2110395 | 1417525 | | 7381865 | 4508435 | | 72% | 39% | | |
|  | 2 | 26 | 572850 | 821904 | 951334 | 1394754 | 951334 | | 2789508 | 1902668 | | 10171373 | 6411103 | | 100% | 55% | | |
|  | 2 | 30 | 451012 | 584713 | 1576514 | 1035725 | 1576514 | | 2071450 | 3153028 | | 12242823 | 9564131 | | 120% | 82% | | |

*FIG. 19I*

ELUTION RESULTS

| | TYRX-COATED ORC | | PEAK AREA | | | CONCENTRATION = RF*AREA | | | TOTAL DRUG AT TIMEPT | | | TOTAL DRUG OVER TIME | | | % DRUG RELEASE OVER TIME | | |
|---|---|---|---|---|---|---|---|---|---|---|---|---|---|---|---|---|---|
| SAMPLE | PBS VOLUME (mL) | TIME | EPI+MINO | MINO | RIF | EPI+MINO | RIF | | EPI+MINO | RIF | | EPI+MINO | RIF | | EPI+MIN | RIF | MINO | RIF |
| 9 | 0 | 0 | 0 | 0 | 0 | 0 | 0 | | 0 | 0 | | 0 | 0 | | 0% | 0% | 0% | 0% |
| | 20 | 2 | 15474 | 24188 | 11774 | 39633 | 11774 | | 793240 | 235480 | | 793240 | 235480 | | 15% | 3% | 15% | 3% |
| | 10 | 4 | 42228 | 52553 | 41925 | 94781 | 41925 | | 947810 | 419250 | | 1741050 | 654730 | | 32% | 10% | 30% | 8% |
| | 5 | 6 | 157128 | 175633 | 255303 | 332761 | 255303 | | 1663805 | 1276515 | | 3404855 | 1931245 | | 63% | 29% | 54% | 22% |
| | 2 | 26 | 576200 | 777329 | 1432680 | 1353529 | 1432680 | | 2707058 | 2865360 | | 6111913 | 4796605 | | 113% | 71% | 88% | 47% |
| | 2 | 30 | 148018 | 182966 | 445777 | 330984 | 445777 | | 661968 | 891554 | | 6773881 | 5688159 | | 125% | 84% | 117% | 77% |
| 10 | 0 | 0 | 0 | 0 | 0 | 0 | 0 | | 0 | 0 | | 0 | 0 | | 0% | 0% | | |
| | 20 | 2 | 16720 | 26959 | 12519 | 43679 | 12519 | | 873580 | 250380 | | 873580 | 250380 | | 15% | 3% | | |
| | 10 | 4 | 31732 | 40584 | 27785 | 72316 | 27785 | | 723160 | 277850 | | 1596740 | 528230 | | 27% | 7% | | |
| | 5 | 6 | 100818 | 117072 | 130127 | 217890 | 130127 | | 1089450 | 650635 | | 2686190 | 1178865 | | 46% | 16% | | |
| | 2 | 26 | 181500 | 293105 | 259567 | 474605 | 259567 | | 949210 | 519134 | | 3635400 | 1697999 | | 62% | 23% | | |
| | 2 | 30 | 612622 | 758657 | 1721196 | 1371279 | 1721196 | | 2742558 | 3442392 | | 6377958 | 5140391 | | 109% | 70% | | |

FIG. 19J

| TYRX-COATED GLYCOPRENE | | | PEAK AREA | | | CONCENTRATION = RF*AREA | | | TOTAL DRUG AT TIMEPT | | | TOTAL DRUG OVER TIME | | | % DRUG RELEASE OVER TIME | | |
|---|---|---|---|---|---|---|---|---|---|---|---|---|---|---|---|---|---|
| SAMPLE | PBS VOLUME (mL) | TIME | EPI-MINO | MINO | RIF | EPI+MINO | RIF | | EPI+MINO | RIF | | EPI+MINO | RIF | | EPI+MIN | RIF | MINO | RIF |
| 11 | 0 | 0 | 0 | 0 | 0 | 0 | 0 | | 0 | 0 | | 0 | 0 | | 0% | 0% | 0% | 0% |
| | 20 | 2 | 40576 | 86595 | 96710 | 127171 | 96710 | | 2543420 | 1934200 | | 2543420 | 1934200 | | 89% | 67% | 87% | 68% |
| | 10 | 4 | 11973 | 15530 | 25453 | 27503 | 25453 | | 275030 | 254530 | | 2818450 | 2188730 | | 98% | 76% | 96% | 77% |
| | 5 | 6 | 10658 | 9532 | 12388 | 20190 | 12388 | | 100950 | 61940 | | 2919400 | 2250670 | | 102% | 78% | 99% | 79% |
| | 2 | 26 | 7704 | 8470 | 10293 | 16174 | 10293 | | 32348 | 20586 | | 2951748 | 2271256 | | 103% | 79% | 100% | 79% |
| | 2 | 30 | 3658 | 4063 | 13183 | 7721 | 13183 | | 15442 | 26366 | | 2967190 | 2297622 | | 103% | 80% | 100% | 80% |
| 12 | 0 | 0 | 0 | 0 | 0 | 0 | 0 | | 0 | 0 | | 0 | 0 | | 0% | 0% | 0% | 0% |
| | 20 | 2 | 42855 | 92896 | 104242 | 135751 | 104242 | | 2715020 | 2084840 | | 2715020 | 2084840 | | 85% | 69% | | |
| | 10 | 4 | 12340 | 16191 | 28143 | 28531 | 28143 | | 285310 | 281430 | | 3000330 | 2366270 | | 94% | 78% | | |
| | 5 | 6 | 9649 | 6794 | 8955 | 16443 | 8955 | | 82215 | 44775 | | 3082545 | 2411045 | | 96% | 80% | | |
| | 2 | 26 | 5532 | 4105 | 0 | 9637 | 0 | | 19274 | 0 | | 3101819 | 2411045 | | 97% | 80% | | |
| | 2 | 30 | 0 | 0 | 0 | 0 | 0 | | 0 | 0 | | 3101819 | 2411045 | | 97% | 80% | | |

*FIG. 19K*

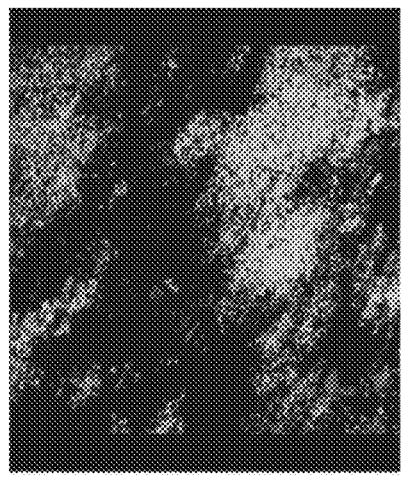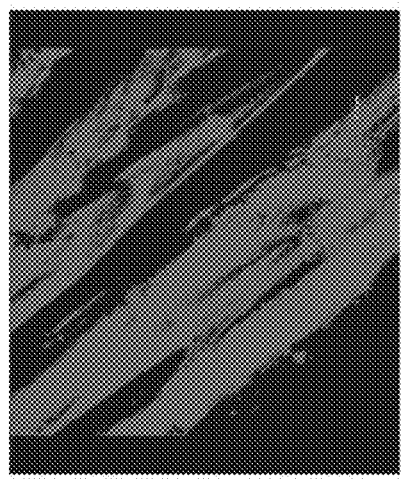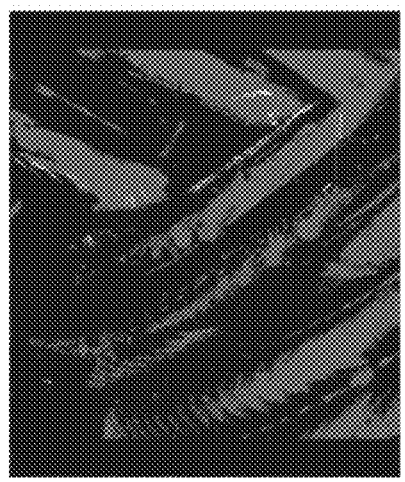
FIG. 25

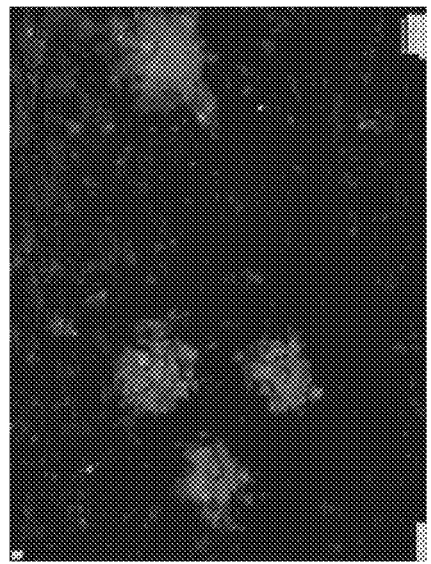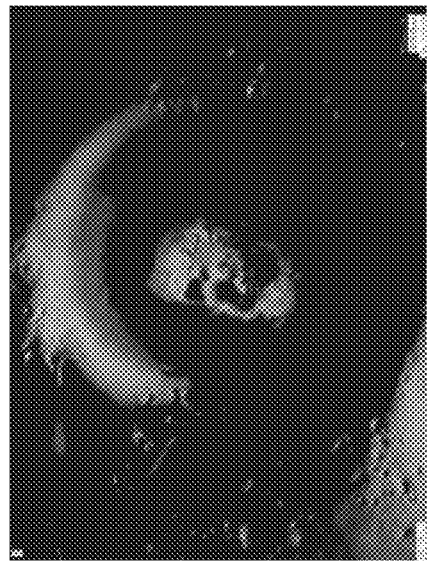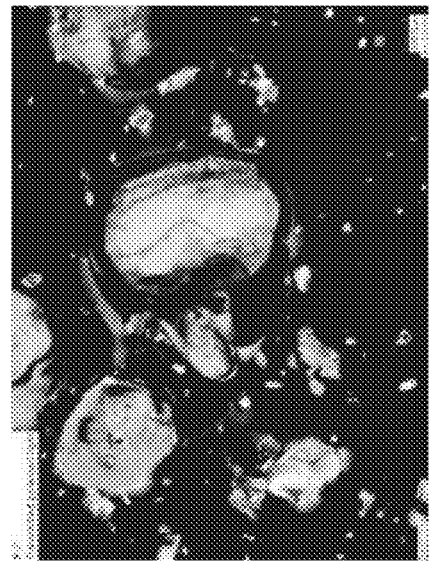
FIG. 26

| | | Weight (mg) | | | | | Sample |
|---|---|---|---|---|---|---|---|
| | Sample | Glycoprene | AIGIS-R | ORC | TYRX-coated ORC | | |
| Drug Elution | 1 | 16.1 | - | - | 60.4 | | 1 |
| | 2 | 13.7 | - | - | 57.7 | | 2 |
| | 3 | - | 14.4 | 56.8 | - | | 3 |
| | 4 | - | 14.9 | 56.1 | - | | 4 |
| | 5 | - | 14.7 | - | 63.6 | | 5 |
| | 6 | - | 13.3 | - | 59.1 | | 6 |
| | 9 | - | - | - | 49.3 | | 9 |
| | 10 | - | - | - | 53.2 | | 10 |
| | 11 | - | 10.3 | - | - | | 11 |
| | 12 | - | 11.5 | - | - | | 12 |
| Drug Content | 13 | - | - | - | 113.9 | | |
| | 14 | - | - | - | 118.1 | | |
| | 15 | - | 87.8 | - | - | | |
| | 16 | - | 95.6 | - | - | | |

FIG. 27

CUSTOMIZABLE ANCHORAGE DEVICES AND METHODS OF USE

TECHNICAL FIELD

The present disclosure generally relates to anchorage devices and methods configured for anchoring an implantable medical device within a body, and more particularly to anchorage devices that can be customized to accommodate different size medical devices.

BACKGROUND

Some known anchorage devices may be used to secure an implantable medical device within a body of a patient. The anchorage device and implantable medical device can be inserted into a desired location within the body of the patient. The anchorage device can be used to help anchor or support the implantable medical device to surrounding tissue. Some known anchorage devices are used to provide temporary support to tissue during a healing process. However, the anchorage devices must be provided in a variety of different sizes to accommodate different size implantable medical devices. For example, small anchorage devices are used for small implantable medical devices and large anchorage devices are used for large implantable medical devices. As such, a medical practitioner is required to have several different size anchorage devices on hand in order to use an anchorage device that appropriately sized for a given implantable medical device. This disclosure describes an improvement over these prior art technologies.

SUMMARY

New anchorage devices and methods are provided to help anchor or support an implantable medical device to surrounding tissue. In one embodiment, an anchorage device is provided that includes a substrate extending along a longitudinal axis between a first end comprising a first bonding area and an opposite second end comprising a second bonding area. The substrate comprises a third bonding area between the first and second bonding areas. In some embodiments, the substrate is configured to be folded along the longitudinal axis such that first portions of the bonding areas engage second portions of the bonding areas.

In some embodiments, the bonding areas each include an adhesive and a removable nonstick material that covers the adhesive. First sections of the adhesives of the first and second bonding areas engage second sections of the adhesives of the first and second bonding areas when the first portions of the first and second bonding areas engage the second portions of the first and second bonding areas. A first section of the nonstick material of the third bonding area engages a second section of the nonstick material of the third bonding area when the first portion of the third bonding area engages the second portion of the third bonding area. As such, a first section of the adhesive of the third bonding area does not engage a second section of the adhesive of the third bonding area, thus leaving an open pocket between first and second bonding areas into which an implantable medical device may be positioned.

In some embodiments, the bonding areas each include an adhesive and a removable nonstick material that covers the adhesive. First sections of the adhesives of the first and third bonding areas engage second sections of the adhesives of the first and third bonding areas when the first portions of the first and third bonding areas engage the second portions of the first and third bonding areas. A first section of the nonstick material of the second bonding area engages a second section of the nonstick material of the second bonding area when the first portion of the second bonding area engages the second portion of the second bonding area. As such, a first section of the adhesive of the second bonding area does not engage a second section of the adhesive of the second bonding area. A portion of the second end from the third bonding area to the second bonding area can then be severed or otherwise removed from the first end, the first end comprising an open pocket between first and third bonding areas into which an implantable medical device may be positioned.

In one embodiment, an anchorage device is provided that includes a substrate extending along a longitudinal axis between a first end comprising a first bonding area and an opposite second end comprising a second bonding area. The substrate comprises a plurality of spaced apart bonding areas between the first and second bonding areas. In some embodiments, the plurality of spaced apart bonding areas comprises third and fourth bonding areas. In some embodiments, the substrate is configured to be folded along the longitudinal axis such that first portions of the bonding areas engage second portions of the bonding areas.

In some embodiments, the bonding areas each include an adhesive and a removable nonstick material that covers the adhesive. First sections of the adhesives of the first and second bonding areas engage second sections of the adhesives of the first and second bonding areas when the first portions of the first and second bonding areas engage the second portions of the first and second bonding areas. First sections of the nonstick materials of the third and fourth bonding areas engage second sections of the nonstick materials of the third and fourth bonding areas when the first portions of the third and fourth bonding areas engage the second portions of the third and fourth bonding areas. As such, first sections of the adhesives of the third and fourth bonding areas do not engage second sections of the adhesives of the third and fourth bonding areas, thus leaving an open pocket between first and second bonding areas into which an implantable medical device may be positioned.

In some embodiments, the bonding areas each include an adhesive and a removable nonstick material that covers the adhesive. First sections of the adhesives of the first and third bonding areas engage second sections of the adhesives of the first and third bonding areas when the first portions of the first and third bonding areas engage the second portions of the first and third bonding areas. First sections of the nonstick materials of the second and fourth bonding areas engage second sections of the nonstick materials of the second and fourth bonding areas when the first portions of the second and fourth bonding areas engage the second portions of the second and fourth bonding areas. As such, first sections of the adhesive of the second and fourth bonding areas do not engage second sections of the adhesives of the second and fourth bonding areas. A portion of the second end from the third bonding area to the second bonding area can then be severed or otherwise removed from the first end, the first end comprising an open pocket between first and third bonding areas into which an implantable medical device may be positioned. In some embodiments, the fourth bonding area is positioned between the second and third bonding areas. In some embodiments, the fourth bonding area is positioned between the first and third bonding areas.

In some embodiments, the anchorage device includes a polymer that is applied to the substrate. In some embodiments, the polymer covers all or a portion of the substrate. In some embodiments, the polymer includes the hemostatic agent such that the hemostatic agent elutes over time in an area surrounding or adjacent to the anchorage device. In some embodiments, the polymer includes an active pharmaceutical ingredient such that the active pharmaceutical agent elutes over time in the area surrounding or adjacent to the anchorage device. In some embodiments, the polymer includes an active pharmaceutical ingredient and a hemostatic agent. In some embodiments, the anchorage device includes a first polymer that includes a hemostatic agent and a second polymer that includes an active pharmaceutical ingredient.

In some embodiments, the substrate includes the hemostatic agent. That is, the substrate is made from the hemostatic agent. In some embodiments, the substrate that is made from the hemostatic agent has an active pharmaceutical ingredient applied to the substrate. In some embodiments, a polymer including the active pharmaceutical ingredient is applied to the substrate such that the active pharmaceutical agent elutes over time in the area surrounding or adjacent to the anchorage device.

In some embodiments, the substrate is a mesh. In some embodiments, the substrate is a thin walled structure, such as, for example, a wafer, sheet or tissue.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which:

FIG. 12 is a table showing results for Example 2;

FIG. 17 is a table showing results for Example 13;

FIG. 19F is a table showing the expected drug content of Samples 1-6 and 9-12 in Example 13;

FIG. 19G is a table showing elution results for Samples 1-6 in Example 13;

FIG. 19H is a table showing elution results for Samples 9-12 in Example 13;

FIG. 19I is a table showing elution results for Samples 9-12 in Example 13;

FIG. 19J is a table showing elution results for Samples 9-12 in Example 13;

FIG. 19K is a table showing elution results for Samples 9-12 in Example 13;

FIG. 25 includes slides showing results discussed in Example 19;

FIG. 26 includes images of samples discussed in Example 21;

FIG. 27 includes a table showing results discussed in Example 13; and

DETAILED DESCRIPTION

Figure 1:
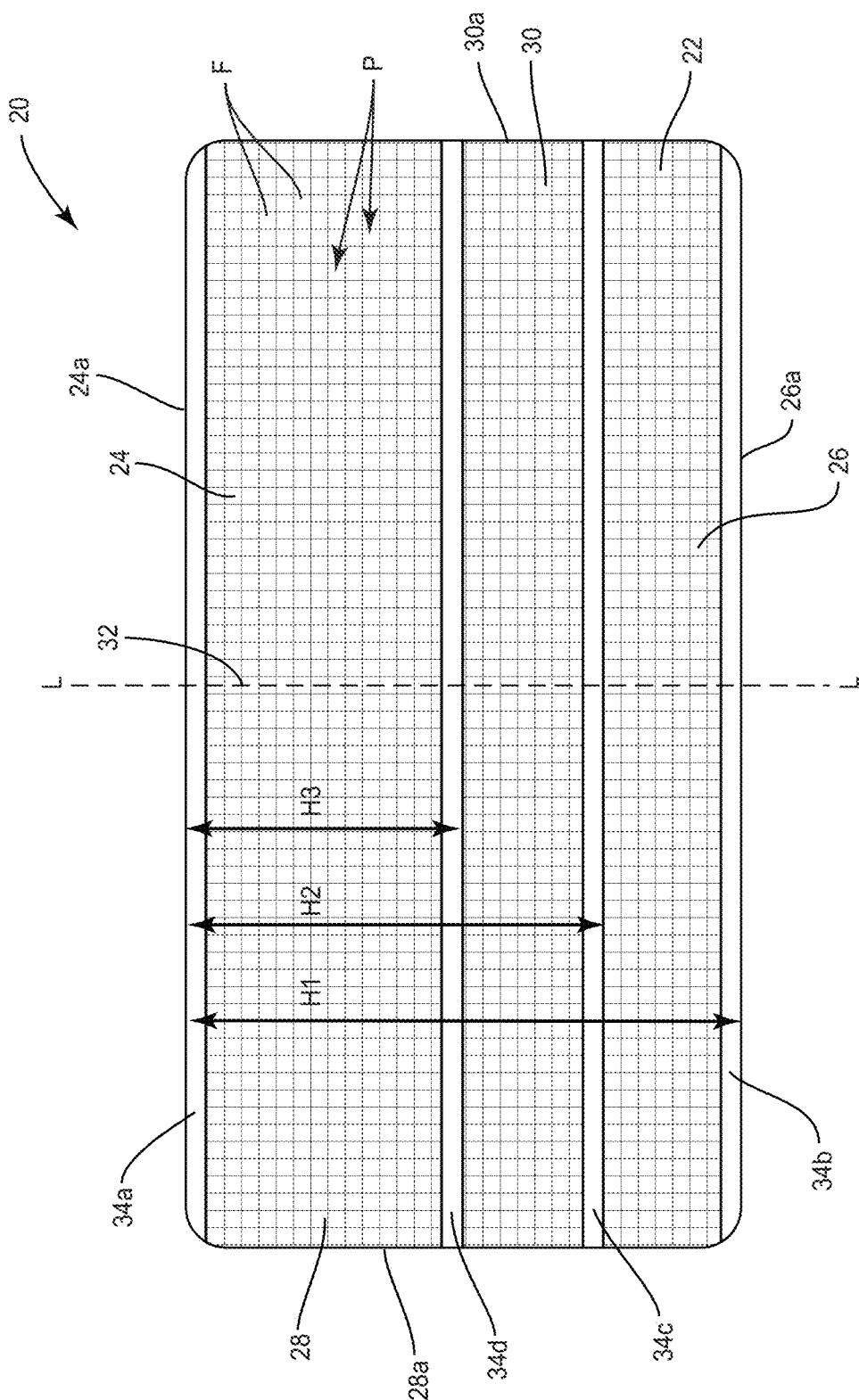
FIG. 1 is a top view of one embodiment of an anchorage device in accordance with the principles of the present disclosure.

For the purposes of this specification and appended claims, unless otherwise indicated, all numbers expressing quantities of ingredients, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

This disclosure is directed to anchorage devices, such as, for example, an anchorage device 20. In some embodiments, the components of anchorage device 20 can be fabricated from biologically acceptable materials suitable for medical applications, including metals, synthetic polymers, allografts, xenografts, isografts, ceramics and bone material and/or their composites, depending on the application and/or preference of a medical practitioner. For example, the components of anchorage device 20, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of anchorage device 20 may have material composites, including the above materials, to achieve various desired characteristics such as strength, rigidity, elasticity, compliance, biomechanical performance, durability and radiolucency or imaging preference. The components of anchorage device 20, individually or collectively, may also be fabricated from a heterogeneous material such as a combination of two or more of the above-described materials. The components of anchorage device 20 may be monolithically formed, integrally connected or include fastening elements and/or instruments, as described herein.

Substrate

Anchorage device 20 includes a substrate, such as, for example, substrate 22. Substrate 22 is configured to be coupled to and/or applied to a device, such as, for example, an implantable medical device or a non-implantable medical device, as discussed herein. In some embodiments, substrate 22 is configured to surround and/or enclose at least a portion of the implantable medical device, as discussed herein. Substrate 22 is configured to be secured to tissue to support the implantable medical device at a treatment site. Implantable medical devices include, for example, vascular devices such as grafts (e.g., abdominal aortic aneurysm grafts, etc.), stents, catheters (including arterial, intravenous, blood pressure, stent graft, etc.), valves (e.g., polymeric or carbon mechanical valves,), embolic protection filters (including distal protection devices), vena cava filters, aneurysm exclusion devices, artificial hearts, cardiac jackets, and heart assist devices (including left ventricle assist devices), implantable defibrillators, subcutaneous implantable defibrillators, implantable monitors, for example, implantable cardiac monitors, electrostimulation devices and leads (including pacemakers, lead adapters and lead connectors), implanted medical device power supplies, peripheral cardiovascular devices, atrial septal defect closures, left atrial appendage filters, valve annuloplasty devices, mitral valve repair devices, vascular intervention devices, ventricular assist pumps, and vascular access devices (including parenteral feeding catheters, vascular access ports, central venous access catheters).

Implantable medical devices may also include, for example, surgical devices such as sutures of all types, anastomosis devices (including anastomotic closures), suture anchors, hemostatic barriers, screws, plates, clips, vascular implants, tissue scaffolds, cerebro-spinal fluid shunts, shunts for hydrocephalus, drainage tubes, catheters including thoracic cavity suction drainage catheters, abscess drainage catheters, biliary drainage products, and implantable pumps. Implantable medical devices may also include, for example, orthopedic devices such as joint implants, acetabular cups, patellar buttons, bone repair/augmentation devices, spinal devices (e.g., vertebral disks and the like), bone pins, cartilage repair devices, and artificial tendons. Implantable medical devices may also include, for example, dental devices such as dental implants and dental fracture repair devices. Implantable medical devices may also include, for example, drug delivery devices such as drug delivery pumps, implanted drug infusion tubes, drug infusion catheters, and intravitreal drug delivery devices. Implantable medical devices may also include, for example, ophthalmic devices such as scleral buckles and sponges, glaucoma drain shunts and intraocular lenses.

Implantable medical devices may also include, for example, urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices. Implantable medical devices may also include, for example, synthetic prostheses such as breast prostheses and artificial organs (e.g., pancreas, liver, lungs, heart, etc.). Implantable medical devices may also include, for example, respiratory devices including lung catheters. Implantable medical devices may also include, for example, neurological devices such as neurostimulators, neurological catheters, neurovascular balloon catheters, neuro-aneurysm treatment coils, and neuropatches, splints, ear wicks, ear drainage tubes, tympanostomy vent tubes, otological strips, laryngectomy tubes, esophageal tubes, esophageal stents, laryngeal stents, salivary bypass tubes, and tracheostomy tubes. Implantable medical devices may also include, for example, oncological implants. Implantable medical devices may also include, for example, pain management implants.

In some embodiments, substrate 22 is configured to be coupled to and/or applied to or to surround and/or enclose at least a portion of a non-implantable medical device, as discussed herein. Non-implantable devices can include dialysis devices and associated tubing, catheters, membranes, and grafts; autotransfusion devices; vascular and surgical devices including atherectomy catheters, angiographic catheters, intraaortic balloon pumps, intracardiac suction devices, blood pumps, blood oxygenator devices (including tubing and membranes), blood filters, blood temperature monitors, hemoperfusion units, plasmapheresis units, transition sheaths, dialators, intrauterine pressure devices, clot extraction catheters, percutaneous transluminal angioplasty catheters, electrophysiology catheters, breathing circuit connectors, stylets (vascular and non-vascular), coronary guide wires, peripheral guide wires; dialators (e.g., urinary, etc.); surgical instruments (e.g. scalpels and the like); endoscopic devices (such as endoscopic surgical tissue extractors, esophageal stethoscopes); and general medical and medically related devices including blood storage bags, umbilical tape, membranes, gloves, surgical drapes, wound dressings, wound management devices, needles, percutaneous closure devices, transducer protectors, pessary, uterine bleeding patches, PAP brushes, clamps (including bulldog clamps), cannulae, cell culture devices, materials for in vitro diagnostics, chromatographic support materials, infection control devices, colostomy bag attachment devices, birth control devices; disposable temperature probes; and pledgets.

Substrate 22 can have a variety of different configurations, shapes and sizes. For example, substrate 22 can be provided with a size and shape or other configuration that can provide the functionality of supporting and immobilizing the implantable medical device at a treatment site within a patient's body, while also improving the removability of anchorage device 20 after the treatment has been completed. In some embodiments, the implantable medical device can be disposed within ae pocket defined by substrate 22 and anchorage device 20 can be implanted and secured to tissue at a desired treatment site within a body of a patient. As discussed herein, during implantation, scar tissue can form at the treatment site and/or tissue can become ingrown within substrate 22. After the treatment is completed, the implantable medical device can remain in the patient as discussed below or can be removed from the patient leaving anchorage device 20 implanted. To remove anchorage device 20, tissue that is ingrown within substrate 22 can be cut or otherwise detached from substrate 22. In some embodiments, a portion of anchorage device 20 may not be removable from the tissue and will remain implanted within the patient.

Substrate 22 may be formed with one or more biocompatible materials, which may be synthetic or naturally occurring. In some embodiments, the one or more biocompatible materials include, for example, polypropylene, polyester, polytetrafluoroethylene, polyamides, silicones, polysulfones, metals, alloys, titanium, stainless steel, shape memory metals (e.g. Nitinol), and/or combinations thereof.

In some embodiments, substrate 22 is configured to be implanted temporarily within a body of a patient and/or is configured to be removed (e.g., explanted) from the patient's body after a period of time. In such embodiments, substrate 22 may include a non-biodegradable material and/or a non-bioresorbable material. For example, substrate 22 may be made entirely from a non-biodegradable material and/or a non-bioresorbable material such that substrate 22 is made only from the non-biodegradable material and/or non-bioresorbable material. In some embodiments, substrate 22 may include one or more non-biodegradable and/or a non-bioresorbable material and one or more biodegradable and/or resorbable material. In some embodiments, one side of substrate 22 may include one or more non-biodegradable and/or a non-bioresorbable material and another side of substrate 22 can include one or more biodegradable and/or resorbable material.

As used herein, the term "biodegradable" refers to, for example, a material that can be at least partially broken down or degraded by a bodily fluid and discarded as waste from the body and/or a material that can be broken down or degraded by a living organism. Thus, "non-biodegradable" can refer to a material that cannot be broken down or degraded by a bodily fluid and/or cannot be broken down or degraded by a living organism. As used herein the term "resorbable" refers to, for example, a material that can be at least partially broken down or degraded by a bodily fluid and assimilated within the body. Thus, a "non-resorbable" material as used herein can refer to, for example, a material that cannot be broken down or degraded by bodily fluid and assimilated within the body.

In some embodiments, the biocompatible biodegradable and/or bioresorbable material or materials may include polymeric and/or non-polymeric materials, such as, for example, one or more poly (alpha-hydroxy acids), poly (lactide-co-glycolide) (PLGA), polylactide (PLA), poly(L-lactide), polyglycolide (PG), polyethylene glycol (PEG) conjugates of poly (alpha-hydroxy acids), polyorthoesters (POE), polyaspirins, polyphosphazenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, silicone, hyaluronic acid, chitosan, or combinations thereof. In one embodiment, substrate 22 comprises Glycoprene, which is sold by Poly-Med, Inc. As used herein, the term "glycoprene" or "Glycoprene" refers to Glycoprene® or Glycoprene II®. Glycoprene® can refer to different variations of the material sold under the trade name Glycoprene®, such as, for example, Glycoprene®6829, Glycoprene®8609 and Glycoprene®7027. In one embodiment, substrate 22 comprises a hemostatic agent, such as, for example, at least one of the hemostatic agents discussed herein.

In some embodiments, the biocompatible non-biodegradable and/or non-bioresorbable material or materials may include polymeric and/or non-polymeric materials, such as, for example, polyurethane, polyester, polytetrafluoroethylene (PTFE), polyethylacrylate/polymethylmethacrylate, polylactide, polylactide-co-glycolide, polyamides, polydioxanone, polyvinyl chloride, polymeric or silicone rubber, collagen, thermoplastics, or combinations thereof.

In some embodiments, substrate 22 is configured to be permanently implanted within a body of a patient. In such embodiments, substrate 22 may include a biodegradable material and/or a bioresorbable material. For example, substrate 22 may be made entirely from a biodegradable material and/or a bioresorbable material such that substrate 22 is made only from the biodegradable material and/or bioresorbable material.

In some embodiments, substrate 22 is provided in the form of a mesh, as shown in FIGS. 1-4. In some embodiments, the mesh is web or fabric with a construction of knitted, braided, woven or non-woven filaments or fibers F that are interlocked in such a way to create a fabric or a fabric-like material that includes a matrix of filaments that define multiple pores P. That is, the space between adjacent filaments or fibers F define pores P of the mesh. Pores P may be beneficial to allow tissue in-growth, for example. In some embodiments, apertures may be formed in the mesh by cutting the filaments or fibers F to decrease the areal density (e.g., surface density) or mass of the mesh and/or further facilitate tissue in-growth. In some embodiments, the apertures that extend through the filaments or fibers F are larger than pores P defined by the filaments or fibers F.

In some embodiments, substrate 22 is provided in the form of a thin walled structure, such as, for example, a wafer, sheet or tissue, as shown in FIGS. 5-8. In some embodiments, the thin walled structure does not include any pores or apertures, in contrast to the mesh discussed herein. In some embodiments, the thin walled structure includes pores or apertures that are smaller than the pores or apertures of the mesh discussed herein. In some embodiments, the thin walled structure has a thickness that is less than a thickness of the mesh discussed herein. In some embodiments, the thickness of the thin walled structure is between about 0.001 inches and about 0.1 inches.

Substrate 22 extends along a longitudinal axis L between opposite ends 24, 26. End 24 includes a surface 24a and end 26 includes a surface 26a, as shown in FIG. 1. Surfaces 24a, 26a each extend between surfaces 28a, 30a of opposite sides 28, 30 of substrate 22. Substrate 22 includes a fold 32 positioned equidistant between surfaces 28a, 30a. In some embodiments, fold 32 has a thickness that is less than a thickness of substrate 22 between fold 32 and surface 28a and/or between fold 32 and surface 30a to facilitate the folding of substrate 22 along longitudinal axis L. In some embodiments, fold 32 is defined by zones of weakness, such as, for example, perforations that extend along longitudinal axis L to facilitate folding of substrate 22. In some embodiments, the perforations each extend completely through a thickness of substrate 22. In some embodiments, the perforations extend into the material that forms substrate 22 without extending through the thickness of substrate 22. In some embodiments, the perforations are uniformly spaced apart from one another. In some embodiments, fold 32 is defined by a single perforation that extends from surface 24a to surface 26a.

In some embodiments, substrate 22 may be manipulated to form a pocket or envelope in which an implantable medical device can be at least partially disposed. That is, substrate 22 is folded along longitudinal axis L at fold 32 to form a cavity C. In particular, substrate 22 is folded such that side 28 engages side 30. Surface 24a adjacent to surface 28a engages surface 24a adjacent to surface 30a and surface 26a adjacent to surface 28a engages surface 26a adjacent to surface 30a. The space between surfaces 28a, 30a define an opening O such that an implantable medical device can be inserted through opening O and into cavity C to enclose, encase or surround all or a portion of the implantable medical device within cavity C.

Figure 2:
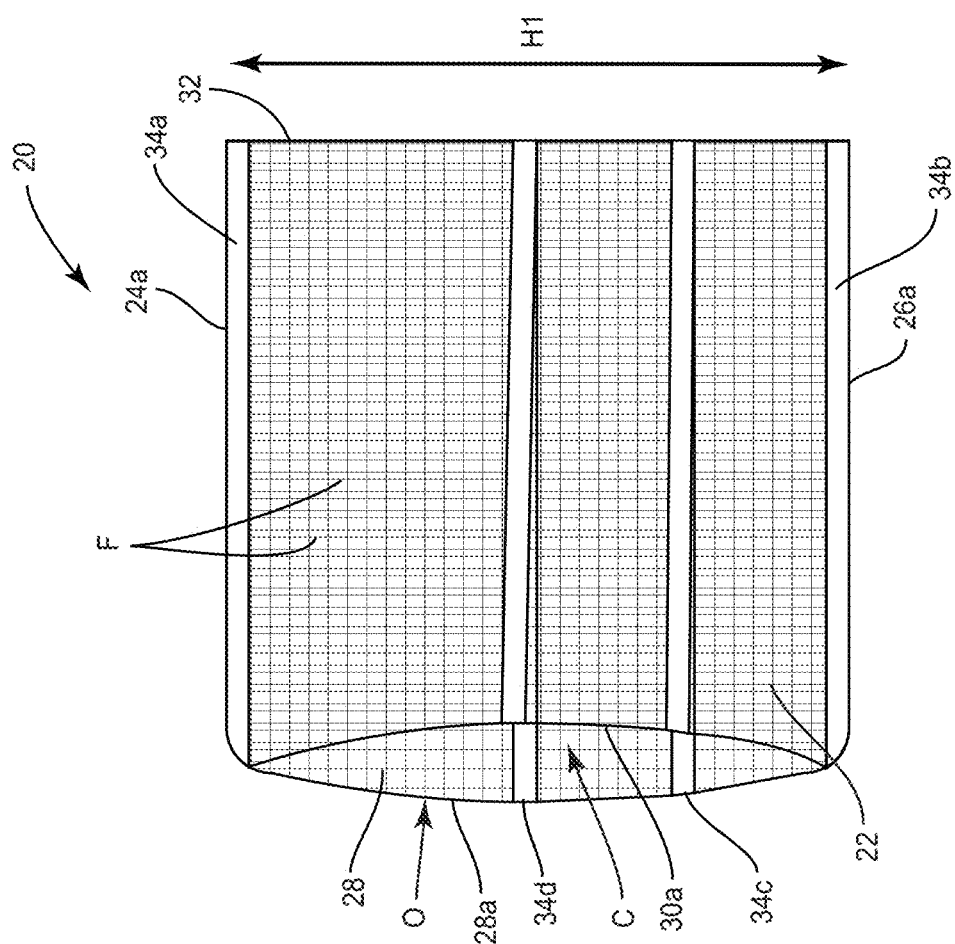
FIG. 2 is a perspective view of one embodiment of the anchorage device shown in FIG. 1.
Figure 3:
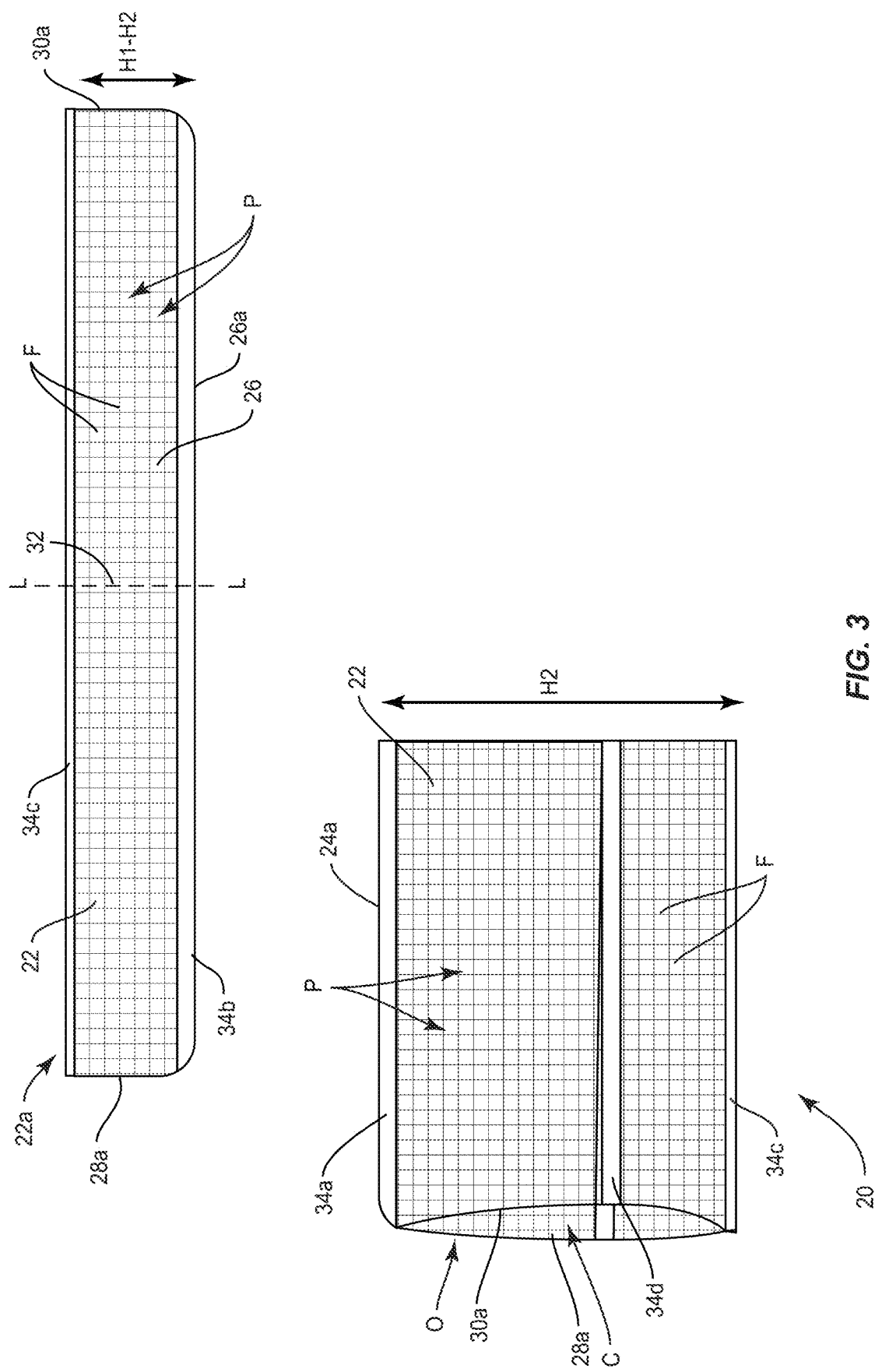
FIG. 3 shows top and perspective views of one embodiment of the anchorage device shown in FIG. 1.
Figure 4:
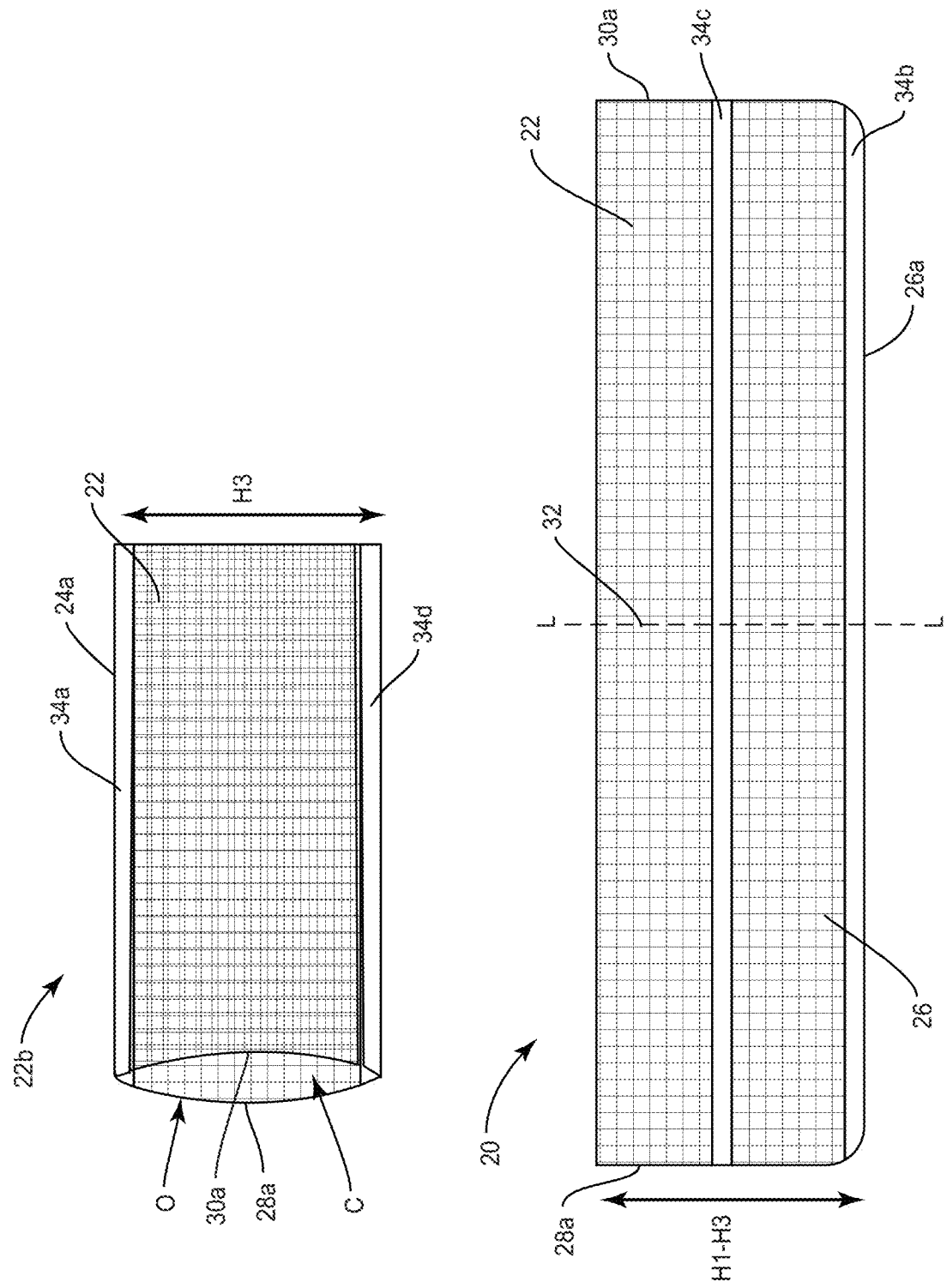
FIG. 4 shows top and perspective views of one embodiment of the anchorage device shown in FIG. 1.
Figure 6:
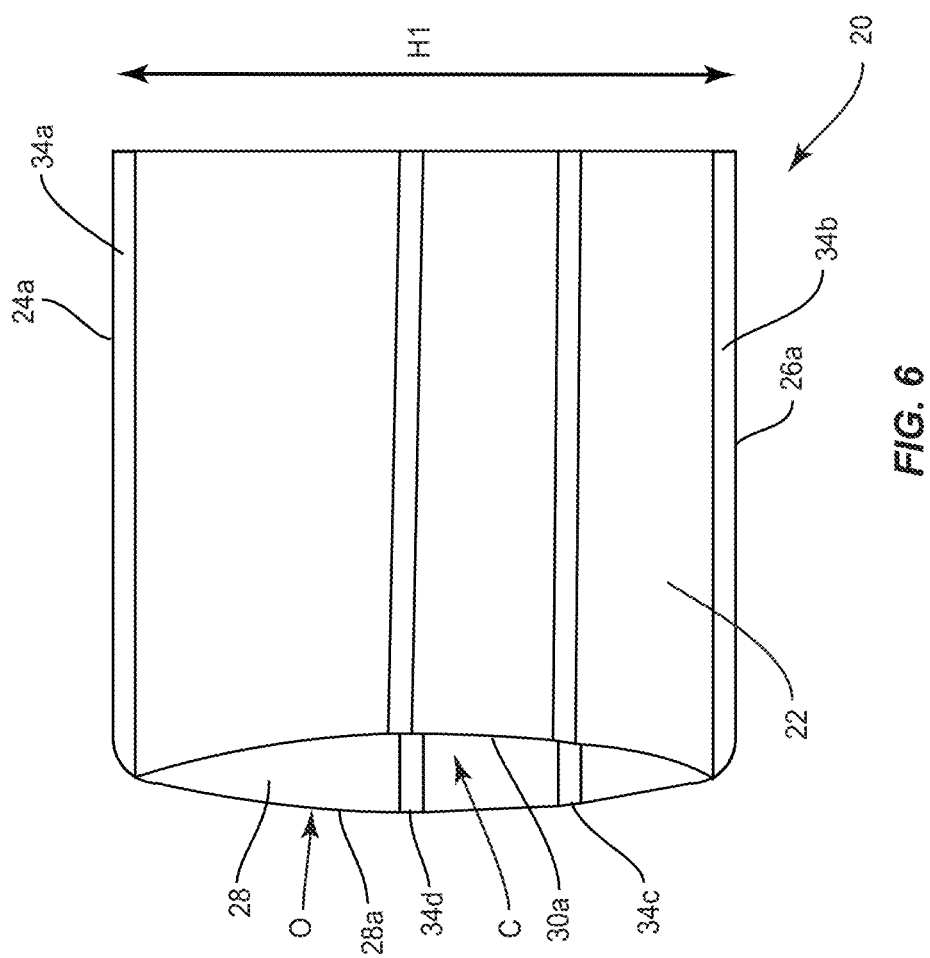
FIG. 6 is a perspective view of one embodiment of the anchorage device shown in FIG. 5.
Figure 7:
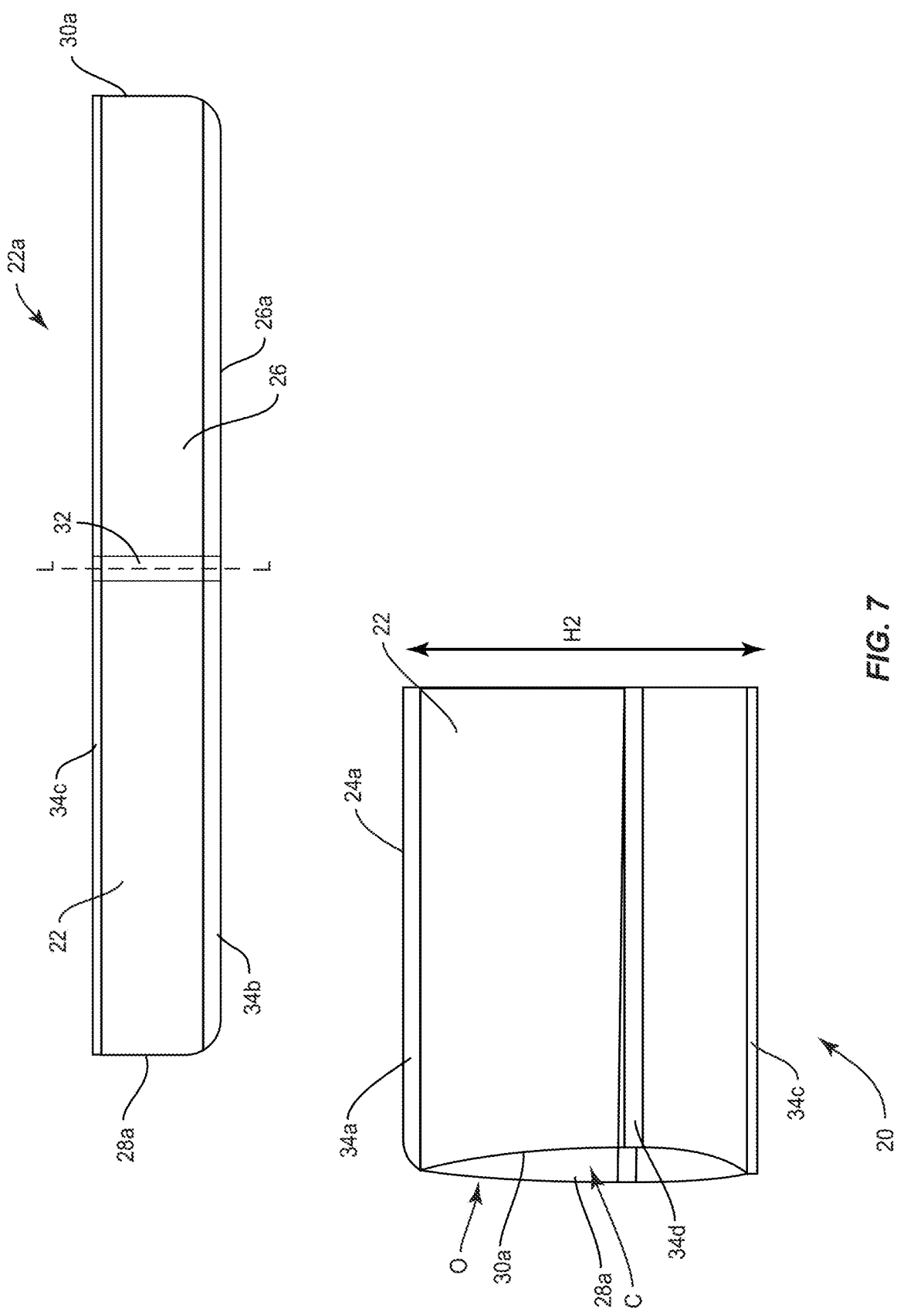
FIG. 7 shows top and perspective views of one embodiment of the anchorage device shown in FIG. 5.
Figure 8:
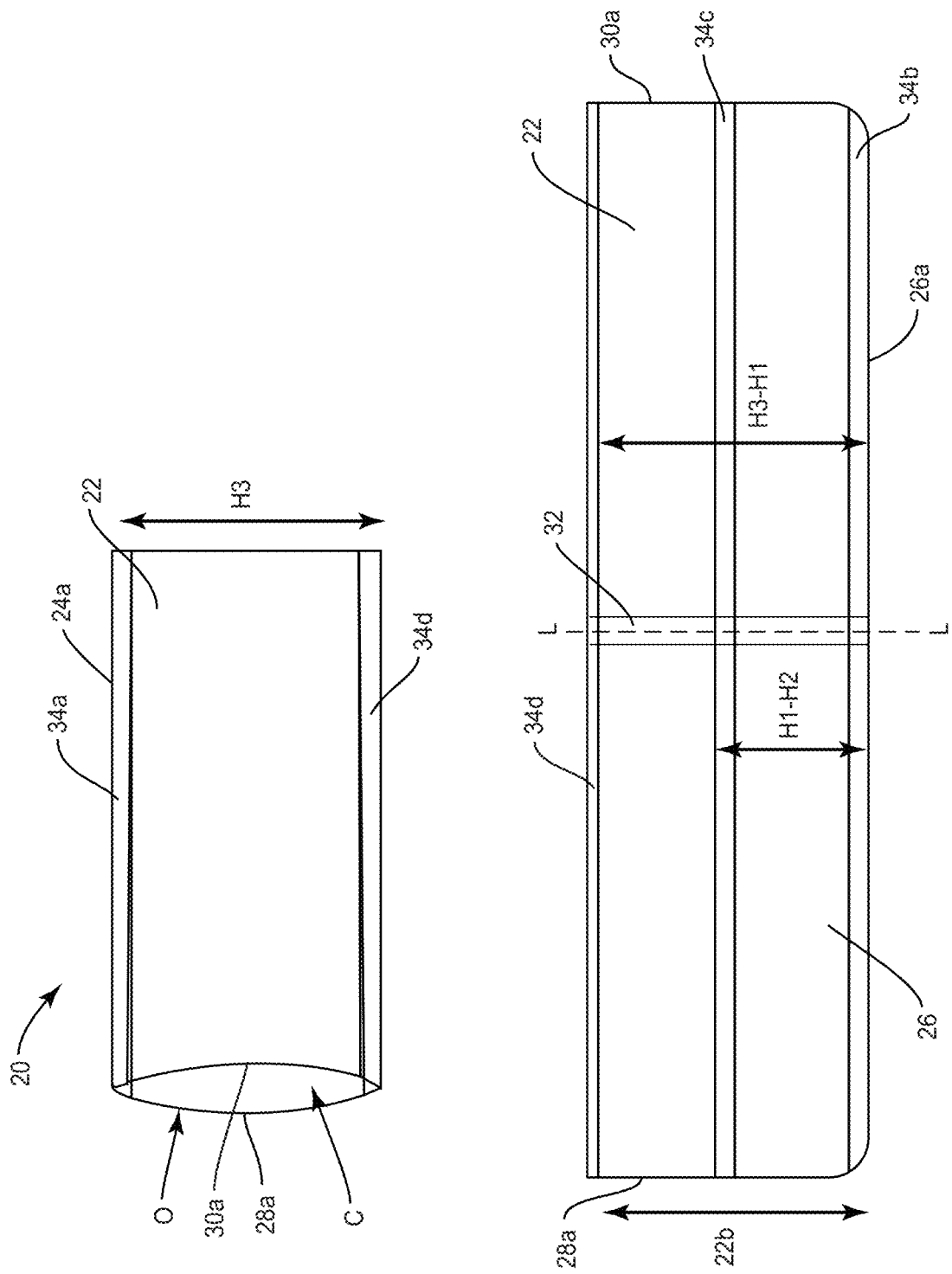
FIG. 8 shows top and perspective views of one embodiment of the anchorage device shown in FIG. 5.

As discussed herein, substrate 22 may be used to form pockets of envelopes that vary in size to accommodate implantable medical devices of different sizes. For example, substrate 22 may form a large pocket, as shown in FIGS. 2 and 6, a medium size pocket, as shown in FIGS. 3 and 7, or a small pocket, as shown in FIGS. 4 and 8. This allows substrate 22 to be customized to accommodate implantable medical devices of different sizes. Indeed, in at least some instances it is preferable to have anchorage device 20 closely match the size of the implantable medical device such that when the implantable medical device is inserted into anchorage device 20, substrate 22 supports the implantable medical device in a manner that minimizes movement of the implantable medical device relative to substrate 22.

Figure 5:
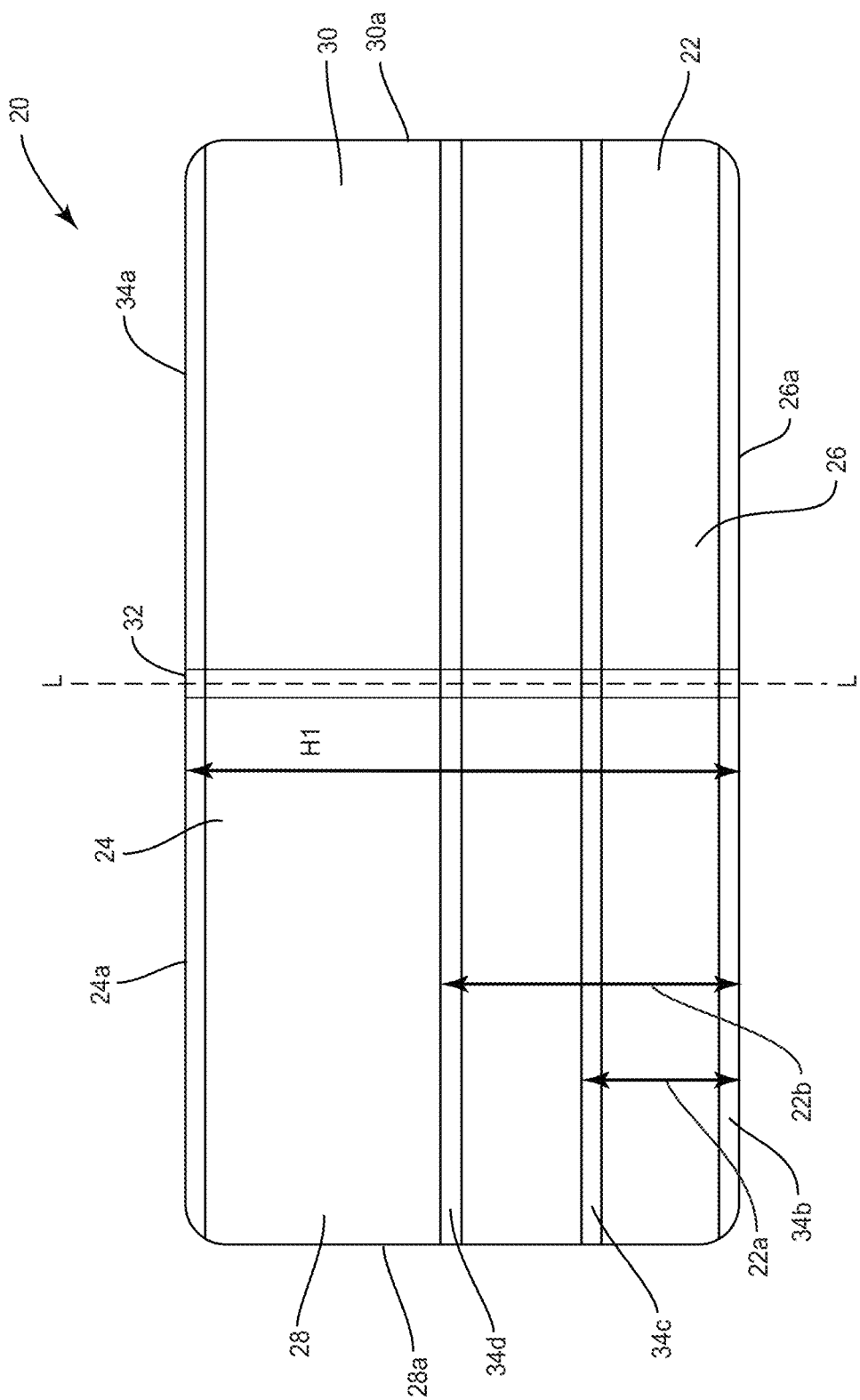
FIG. 5 is a top view of one embodiment of an anchorage device in accordance with the principles of the present disclosure.

To customize the size of anchorage device 20, substrate 22 includes a plurality of bonding areas 34 that are spaced apart from one another along longitudinal axis L, such as, for example, bonding areas 34a, 34b, 34c, 34d, as shown in FIGS. 1 and 5. Bonding area 34a extends along surface 24a and bonding area 34b extend along surface 26a. Bonding area 34d is positioned between bonding areas 34a, 34b and bonding area 34c is positioned between bonding areas 34b, 34d. In some embodiments, bonding area 34d is positioned equidistant between bonding areas 34a, 34b and/or bonding area 34c is positioned equidistant between bonding areas 34b, 34d. It is envisioned that substrate 22 can include any number of bonding areas 34, depending upon, for example, the number of different size anchorage devices 20 that can be made from a single substrate 22. In some embodiments, bonding areas 34 each extend parallel to one another. In some embodiments, bonding areas 34 each extend transverse or perpendicular to longitudinal axis L.

In some embodiments, bonding areas 34 each include an adhesive and a nonstick material that covers the adhesive. The nonstick material is removable from the adhesive such that each bonding area 34 can be movable from a first configuration in which one portion of each bonding area 34 can stick to another portion of that bonding area 34 and a second configuration in which the portions of each bonding area 34 cannot stick to the other portion of that bonding area 34. For example, when the nonstick material is positioned on the adhesive of bonding area 34a, a first portion of bonding area 34a adjacent to side 28 will not stick to a second portion of bonding area 34a adjacent to side 28 when substrate 22 is folded along longitudinal axis L at fold 32 such that surface 28a engages surface 30a. However, when the nonstick material is removed from the adhesive of bonding area 34a, the first portion of bonding area 34a adjacent to side 28 will stick to the second portion of bonding area 34a adjacent to side 28 when substrate 22 is folded along longitudinal axis L at fold 32 such that surface 28a engages surface 30a. In some embodiments, the nonstick material is a removable strip. In some embodiments, the nonstick material is a waxy material.

To create a pocket having a first height H1, the nonstick material on the adhesive of bonding areas 34a, 34b is removed, while the nonstick material of bonding areas 34c, 34d remains on the adhesive of bonding areas 34c, 34d. Substrate 22 is folded along fold 32 such that surface 28a engages surface 30a. As substrate 22 is folded along fold 32 the adhesive along the first portion of bonding area 34a adjacent to side 28 will stick to the adhesive along the second portion of bonding area 34a adjacent to side 28 and the adhesive along the first portion of bonding area 34b adjacent to side 28 will stick to the adhesive along the second portion of bonding area 34b adjacent to side 28 such that substrate forms a pocket having first height H1, as shown in FIGS. 2 and 6. Cavity C and opening O of the pockets shown in FIGS. 2 and 6 each have a diameter or height that is equal to first height H1 such that an implantable medical device having a width that is approximately equal to first height H1 can be inserted through opening O and into cavity C.

To create a pocket having a second height H2, the nonstick material on the adhesive of bonding areas 34a, 34c is removed, while the nonstick material of bonding areas 34b, 34d remains on the adhesive of bonding areas 34b, 34d. Substrate 22 is folded along fold 32 such that surface 28a engages surface 30a. As substrate 22 is folded along fold 32 the adhesive along the first portion of bonding area 34a adjacent to side 28 will stick to the adhesive along the second portion of bonding area 34a adjacent to side 28 and the adhesive along the first portion of bonding area 34c adjacent to side 28 will stick to the adhesive along the second portion of bonding area 34c adjacent to side 28 such that substrate forms a pocket having second height H2, as shown in FIGS. 3 and 7. In some embodiments, a portion 22a of substrate 22 from bonding area 34c to bonding area 34b is removed from the portion of substrate 22 from bonding area 34a to bonding area 34c. In some embodiments, portion 22a is removed by severing portion 22a from the portion of substrate 22 from bonding area 34a to bonding area 34c. In some embodiments, severing includes cutting substrate 22 along or adjacent to bonding area 34c with a blade or scissors, for example. Cavity C and opening O of the pockets shown in FIGS. 3 and 7 each have a diameter or height that is equal to second height H2 such that an implantable medical device having a width that is approximately equal to second height H2 can be inserted through opening O and into cavity C.

To create a pocket having a third height H3, the nonstick material on the adhesive of bonding areas 34a, 34d is removed, while the nonstick material of bonding areas 34b, 34c remains on the adhesive of bonding areas 34b, 34c. Substrate 22 is folded along fold 32 such that surface 28a engages surface 30a. As substrate 22 is folded along fold 32 the adhesive along the first portion of bonding area 34a adjacent to side 28 will stick to the adhesive along the second portion of bonding area 34a adjacent to side 28 and the adhesive along the first portion of bonding area 34d adjacent to side 28 will stick to the adhesive along the second portion of bonding area 34d adjacent to side 28 such that substrate forms a pocket having third height H3, as shown in FIGS. 4 and 8. In some embodiments, a portion 22b of substrate 22 from bonding area 34d to bonding area 34b is removed from the portion of substrate 22 from bonding area 34a to bonding area 34d. In some embodiments, portion 22b is removed by severing portion 22b from the portion of substrate 22 from bonding area 34a to bonding area 34d. In some embodiments, severing includes cutting substrate 22 along or adjacent to bonding area 34c with a blade or scissors, for example. Cavity C and opening O of the pockets shown in FIGS. 4 and 8 each have a diameter or height that is equal to third height H3 such that an implantable medical device having a width that is approximately equal to third height H3 can be inserted through opening O and into cavity C.

As demonstrated above, a single substrate 22 can be manipulated to form pockets having a plurality of different heights, such as, for example, height H1, height H2 and height H3. As such, a medical practitioner can tailor substrate 22 to accommodate implantable medical devices of different sizes. For example, an anchorage device 20 including any of heights H1, H2, H3 can be created from a single substrate 22 to closely fit implantable medical devices having at least three different heights therein. This allows the medical practitioner to form pockets that are closest in size to the implantable medical device that is going to be inserted into the pocket. As such, the need to carry a variety of different size anchorage devices or substrates is eliminated, thus reducing inventory.

As demonstrated above, bonding areas 34 can be selectively positioned along longitudinal axis to create anchorage devices 20 having selected heights. That is, an anchorage device 20 having a height X can be created by positioning one of bonding areas 34 a distance X from bonding area 34a. The nonstick material on the adhesive of bonding area 34a and the bonding area 34 distance X from bonding area 34a is removed, while the nonstick material of the other bonding areas 34 remains on the adhesive of the other bonding areas 34. Substrate 22 is folded along fold 32 such that surface 28a engages surface 30a. As substrate 22 is folded along fold 32 the adhesive along the first portion of bonding area 34a adjacent to side 28 will stick to the adhesive along the second portion of bonding area 34a adjacent to side 28 and the adhesive along the first portion of the bonding area 34 distance X from bonding area 34a adjacent to side 28 will stick to the adhesive along the second portion of the bonding area 34 distance X from bonding area 34a adjacent to side 28 such that substrate forms a pocket having height X. In some embodiments, a portion of substrate 22 from the bonding area 34 distance X from bonding area 34a to bonding area 34b is removed from the portion of substrate 22 from bonding area 34a to the bonding area 34 distance X from bonding area 34*a*. Cavity C and opening O of the resulting pockets will each have a diameter or height that is equal to height X such that an implantable medical device having a width that is approximately equal to height X can be inserted through opening O and into cavity C.

In some embodiments, sides 28, 30 each include a mesh discussed herein. In some embodiments, side 28 includes a mesh including pores having a first size and side 30 includes a mesh including pores having a second size, wherein the first size is different than the first size. In some embodiments, the first size is greater than the second size. In some embodiments, the first size is less than the second size. In some embodiments, sides 28, 30 each include a thin walled structure discussed herein. In some embodiments one of sides 28, 30 includes a mesh discussed herein and the other one of sides 28, 30 includes a thin walled structure discussed herein that does not have any pores or apertures.

In some embodiments, sides 28, 30 are formed from the same material. In some embodiments one of sides 28, 30 is formed from a first material, such as, for example, one of the materials discussed herein, and the other one of sides 28, 30 is made from a second material, such as, for example, one of the materials discussed herein, wherein the second material is different than the first material. For example, side 28 may be formed from a biodegradable and/or bioresorbable material and side 30 may be formed from a non-biodegradable and/or non-bioresorbable material, or vice versa. In some embodiments, sides 28, 30 are each formed from a biodegradable and/or bioresorbable material, wherein the biodegradable and/or bioresorbable materials degrade and/or resorb at the same rate. In some embodiments, sides 28, 30 are formed from different biodegradable and/or bioresorbable materials, wherein one of the biodegradable and/or bioresorbable materials degrades and/or resorbs more quickly than the other biodegradable and/or bioresorbable material.

In some embodiments, sides 28, 30 each include a single layer of material, such as, for example, one of the materials discussed herein. In some embodiments, at least one of sides 28, 30 includes multiple layers. In some embodiments, the multiple layers include more than one layer of the mesh discussed herein. In some embodiments, the multiple layers include more than one layer of the thin walled structure discussed herein. In some embodiments, the multiple layers include one or more layer of the mesh discussed herein and one or more layer of the thin walled structure discussed herein. In some embodiments, the multiple layers include one or more layer of the mesh discussed herein and one or more layer of the thin walled structure discussed herein, wherein one of the layers of mesh is positioned between two layers of the thin walled structure. In some embodiments, the multiple layers include one or more layer of the mesh discussed herein and one or more layer of the thin walled structure discussed herein, wherein one of the layers of thin walled structure is positioned between two layers of the mesh.

Figure 9:
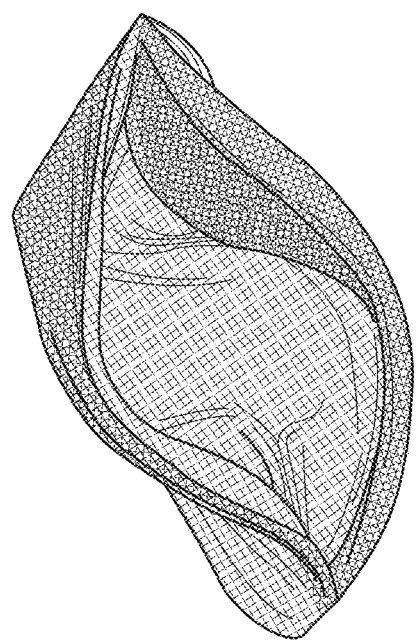
FIG. 9 is a top perspective view of one embodiment of an anchorage device in accordance with the principles of the present disclosure.

In one embodiment, sides 28, 30 may be folded inwardly after substrate 22 is manipulated to form a pocket such that surfaces 28*a*, 30*a* are positioned within cavity C, as shown in FIG. 9. This allows a medical practitioner to further customize the size of anchorage device 20, such as, for example, the size of cavity C. In particular, the medical practitioner can fold sides 28, 30 inwardly at different points along ends 24, 26 to vary the distance surfaces 28*a*, 30*a* are positioned within cavity C. Where a deep cavity C is desired, sides 28, 30 may not be folded inwardly or may only be folded inwardly a small amount. In contrast, when a shallower cavity C is desired, sides 28, 30 may be folded inwardly a greater amount.

Hemostatic Agent(s)

Anchorage device 20 includes an agent, such as, for example, a hemostatic agent. The hemostatic agent can include one more hemostatic agent, such as, for example, epinephrine, tranexamic acid, chitosan and oxidized regenerated cellulose. In some embodiments, the hemostatic agent can include one or more of Spongostan®, Surgifoam®, Avitene, thrombin and Ostene® in addition to or in place of the hemostatic agents discussed above. The hemostatic agent can be selected from any of the hemostatic agents discussed herein and/or tranexamic acid, amino caproic acid (e.g., epsilon amino caproic acid), aprotinin, natural serine protease inhibitors, or polymers such as ORC or chitosan or other polysaccharides. In some embodiments, the hemostatic agents can include Arista AH hemostat and a desiccant. In some embodiments, the Arista AH hemostat is a hydrophilic, flowable, sterile, fine, dry white powder made by crosslinking purified plant starch through a proprietary process into MicroporousPolysaccharide Hemospheres (MPH). In some embodiments, the hemostatic agents can include those discussed by Barnard J, Millner R, "A Review of Topical Hemostatic Agents for Use in Cardiac Surgery," Ann Thorac Surg. 2009, 88: 1377-1383. 10.1016, which is incorporated herein by reference, in its entirety. In some embodiments, the hemostatic agents can include those discussed by Jill Henley, Jerry D. Brewer, "Newer Hemostatic Agents Used in the Practice of Dermatologic Surgery," Dermatology Research and Practice 2013, 1-15, which is incorporated herein by reference, in its entirety. In some embodiments, the hemostatic agents can include those discussed by F. I. Broekema, W. Van Oeveren, J. Zuidema, S. H. Visscher, and R. R. M. Bos, "In vitro analysis of polyurethane foam as a topical hemostatic agent," Journal of Materials Science, vol. 22, no. 4, pp. 1081-1086, 2011, which is incorporated herein by reference, in its entirety.

In some embodiments, hemostatic agent 24 can include one or more of protamine, norepinephrine, desmopressin, lysine analogs, collagen, gelatin, polysaccharide spheres, mineral zeolite, bovine thrombin, pooled human thrombin, recombinant thrombin, gelatin and thrombin, collagen and thrombin, cyanacrylate, fibrin glue, polyethylene glycol, and glutaraldehyde in addition to or in place of the hemostatic agents discussed above. In some embodiments, the lysine analog is tranexamic acid and has the formula:

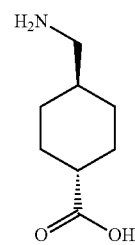

In some embodiments, the anchorage devices disclosed herein utilize one or more pharmacologic hemostatic agent since pharmacologic hemostatic agents have been found to be desirable over mechanical hemostats for a variety of reasons. Ethnographic research has showed that physicians desire a hemostat that can provide an extended elution profile to reduce bleeding events for up to 7 days post operatively. Furthermore, there is a possible effect on handling and/or allergic reactions if mechanical hemostats, such as, for example, oxidized reduced cellulose or chitosan were used.

Figure 11:
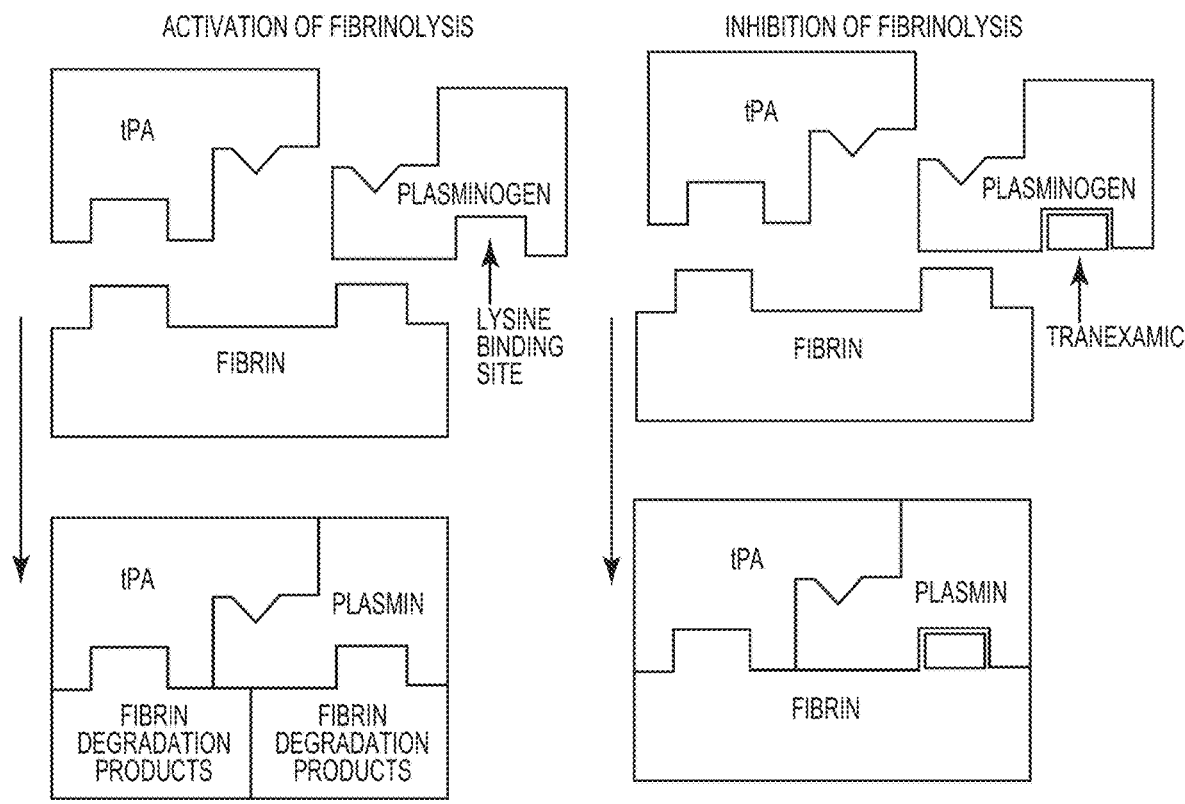
FIG. 11 is a depiction of the mechanism of action for a hemostatic agent in accordance with the principles of the present disclosure.

In some embodiments, tranexamic acid is preferred for use as hemostatic agent 24. Tranexamic acid is a synthetic analog of the amino acid lysine with a molecular weight of 157 g/mol. Tranexamic acid is an antifibrinolytic agent that acts by binding to plasminogen and blocking the interaction of plasminogen with fibrin, therefore preventing the dissolution of a fibrin clot. In the presence of a wound, fibrinolysis occurs naturally when a lysine residue such as tissue plasminogen activator (tPA), binds to plasmin causing the clot to lyse (or break). Tranexamic acid blocks tPA and keeps the clot from breaking, thus preventing unwanted bleeding. FIG. 11 depicts this process.

In some embodiments, the hemostatic agent includes a mixture or combination of the hemostatic agents discussed herein. In some embodiments, the hemostatic agent is applied directly to substrate 22. That is, the hemostatic agent is not applied to substrate 22 in a polymer, such as, for example, a polymer that includes the hemostatic agent. In some embodiments, the hemostatic agent may be applied to substrate 22 by spraying the hemostatic agent onto substrate 22, coating all or a portion of substrate 22 with the hemostatic agent, coating all or a portion of substrate 22 with a material, such as, for example, applying a polymer to substrate 22 that includes the hemostatic agent, washing substrate 22 with the hemostatic agent, or printing the hemostatic agent on substrate 22 with a printer, such as, for example a 3D printer. In some embodiments, the hemostatic agent is a material that forms substrate 22. That is, substrate 22 is made from the hemostatic agent. In some embodiments, substrate 22 is made only from the hemostatic agent.

In some embodiments, the hemostatic agent can be applied to at least one of sides 28, 30. In some embodiments, only one of sides 28, 30 includes the hemostatic agent. In some embodiments, the hemostatic agent is applied only to opposite outer surfaces of sides 28, 30. That is, the inner surfaces of sides 28, 30 that face one another and define cavity C do not have the hemostatic agent applied thereto. In some embodiments, the hemostatic agent is applied only to the inner surfaces of sides 28, 30 that define cavity C. That is, the opposite outer surfaces of sides 28, 30 that face away from one another do not have the hemostatic agent applied thereto. In some embodiments, the hemostatic agent is applied only to the inner surface of one of sides 28, 30 and to the outer surface of the other one of sides 28, 30.

In some embodiments, a first the hemostatic agent can be applied to side 28 and a second the hemostatic agent can be applied to side 30, wherein the second the hemostatic agent is different than the first the hemostatic agent. In some embodiments, a first the hemostatic agent is applied to the outer surfaces of sides 28, 30 and a second the hemostatic agent is applied to the inner surfaces of sides 28, 30, wherein the second the hemostatic agent is different than the first the hemostatic agent.

The hemostatic agent is configured to elute from anchorage device 20 into an area surrounding or adjacent to anchorage 20 to reduce or prevent bleeding within a patient, such as, for example, bleeding caused by a surgical procedure. The amount of the hemostatic agent that is applied to substrate 22 can be varied to elute a selected amount of the hemostatic agent and/or to elute the hemostatic agent at a selected rate and/or to elute hemostatic agent over a selected number of hours or days. In some embodiments, the hemostatic agent is eluted into surrounding bodily tissue, bodily fluid, or systemic fluid, to reduce or prevent bleeding. In some embodiments, the hemostatic agent may be eluted for up to 30 hours. In some embodiments, between about 40% and about 100% of the hemostatic agent is eluted over a period of at least about 30 hours. In some embodiments, 60% and about 100% of the hemostatic agent is eluted over a period of at least about 30 hours. In some embodiments, between about 65% and about 100% of the hemostatic agent is eluted over a period of at least about 36 hours. In some embodiments, 80% and about 100% of the hemostatic agent is eluted over a period of at least about 36 hours. In some embodiments, between about 60% and about 100% of the hemostatic agent is eluted over a period of at least about 48 hours. In some embodiments, 80% and about 100% of the hemostatic agent is eluted over a period of at least about 48 hours. In some embodiments, between about 60% and about 100% of the hemostatic agent is eluted over a period of at least about 60 hours. In some embodiments, 80% and about 100% of the hemostatic agent is eluted over a period of at least about 60 hours.

In some embodiments, anchorage device 20 may include a polymer that is applied to and/or coats at least a portion of substrate 22, wherein the polymer includes the hemostatic agent. That is, the hemostatic agent is applied to substrate 22 via the polymer. In some embodiments, the polymer includes a combination, blend or mixture of polymers. In some embodiments, the polymer is configured to degrade within a patient and releases the hemostatic agent as the polymer degrades. In some embodiments, the degradation rate of the polymer is known or can be predicted to allow a medical practitioner to select a polymer or a quantity of polymer that is applied to substrate 22 to produce anchorage device 20 that is customized to elute a selected quantity of the hemostatic agent at a selected rate over a selected period of time. For example, the polymer may be selected to elute a selected quantity of the hemostatic agent per hour or day for a selected number of days or hours.

In some embodiments, the polymer is selected from the group consisting of polylactic acid, polyglycolic acid, poly (L-lactide), poly(D,L-lactide)polyglycolic acid[polyglycolide], poly(L-lactide-co-D,L-lactide), poly(L-lactide-co-glycolide), poly(D, L-lactide-co-glycolide), poly(glycolide-co-trimethylene carbonate), poly(D,L-lactide-co-caprolactone), poly(glycolide-co-caprolactone), polyethylene oxide, polydioxanone, polypropylene fumarate, poly(ethyl glutamate-co-glutamic acid), poly(tert-butyloxy-carbonylmethyl glutamate), polycaprolactone, polycaprolactone co-butylacrylate, polyhydroxybutyrate, copolymers of polyhydroxybutyrate, poly(phosphazene), poly(phosphate ester), poly(amino acid), polydepsipeptides, maleic anhydride copolymers, polyiminocarbonates, poly [(97.5% dimethyl-trimethylene carbonate)-co-(2.5% trimethylene carbonate)], poly(orthoesters), tyrosine-derived polyarylates, tyrosine-derived polycarbonates, tyrosine-derived polyiminocarbonates, tyrosine-derived polyphosphonates, polyethylene oxide, polyethylene glycol, polyalkylene oxides, hydroxypropylmethylcellulose, polysaccharides such as hyaluronic acid, chitosan and regenerate cellulose. In some embodiments, the polymer may include combinations, blends or mixtures of the polymers discussed herein.

In some embodiments, the polymer is a polyarylate. In some embodiments, the polymer is a tyrosine-derived polyarylate. In some embodiments, the tyrosine-derived polyarylate is p(DTE co X % DT succinate), where X is about 10% to about 30%. In some embodiments, the tyrosine-derived polyarylate is p(DTE co X % DT succinate), where X ranges from about 26.5% to about 28.5%. In some embodiments, the tyrosine-derived polyarylate is p(DTE co X % DT succinate), where X is about 27.5%. In some embodiments, the polymer is P22-27.5 DT. In some embodiments, the polymer is p22-27.5 DT.

As used herein, DTE is the diphenol monomer desaminotyrosyl-tyrosine ethyl ester; DTBn is the diphenol monomer desaminotyrosyl-tyrosine benzyl ester; DT is the corresponding free acid form, namely desaminotyrosyl-tyrosine. BTE is the diphenol monomer 4-hydroxy benzoic acid-tyrosyl ethyl ester; BT is the corresponding free acid form, namely 4-hydroxy benzoic acid-tyrosine.

P22 is a polyarylate copolymer produced by condensation of DTE with succinate. P22-10, P22-15, P22-20, P22-xx, etc., represents copolymers produced by condensation of (1) a mixture of DTE and DT using the indicated percentage of DT (i.e., 10, 15, 20 and xx % DT, etc.) with (2) succinate.

In some embodiments, the polymer includes one or more polyarylates that are copolymers of desaminotyrosyl-tyrosine (DT) and an desaminotyrosyl-tyrosyl ester (DT ester), wherein the copolymer comprises from about 0.001% DT to about 80% DT and the ester moiety can be a branched or unbranched alkyl, alkylaryl, or alkylene ether group having up to 18 carbon atoms, any group of which can, optionally have a polyalkylene oxide therein. Similarly, another group of polyarylates are the same as the foregoing but the desaminotyrosyl moiety is replaced by a 4-hydroxybenzoyl moiety. In some embodiments, the DT or BT contents include those copolymers with from about 1% to about 30%, from about 5% to about 30% from about 10 to about 30% DT or BT. In some embodiments, the diacids (used informing the polyarylates) include succinate, glutarate and glycolic acid.

In some embodiments, the polymer includes one or more biodegradable, resorbable polyarylates and polycarbonates. These polymers, include, but are not limited to, BTE glutarate, DTM glutarate, DT propylamide glutarate, DT glycineamide glutarate, BTE succinate, BTM succinate, BTE succinate PEG, BTM succinate PEG, DTM succinate PEG, DTM succinate, DT N-hydroxysuccinimide succinate, DT glucosamine succinate, DT glucosamine glutarate, DT PEG ester succinate, DT PEG amide succinate, DT PEG ester glutarate, DT PEG ester succinate, DTMB P(Desaminotyrsoyl tyrosine methylparaben ester-glutarate), and DTPP P(Desaminotyrsoyl tyrosine propylparaben ester-glutarate).

In some embodiments, the polymer is one more polymers from the DTE-DT succinate family of polymers, e.g., the P22-xx family of polymers having from 0-50%, 5-50%, 5-40%, 1-30% or 10-30% DT, including but not limited to, about 1, 2, 5, 10, 15, 20, 25, 27.5, 30, 35, 40%, 45% and 50% DT. In some embodiments, the polymer is P22-27.5 DT.

In some embodiments, the polymer has diphenol monomer units that are copolymerized with an appropriate chemical moiety to form a polyarylate, a polycarbonate, a polyiminocarbonate, a polyphosphonate or any other polymer.

In some embodiments, the polymer is tyrosine-based polyarylate. In some embodiments, the polymer includes blends and copolymers with polyalkylene oxides, including polyethylene glycol (PEG).

In some embodiments, the polymer can have from 0.1-99.9% PEG diacid to promote the degradation process. In some embodiments, the polymer includes blends of polyarylates or other biodegradable polymers with polyarylates.

The polymer is configured to release the hemostatic agent over time, as discussed herein. In some embodiments, the polymer is configured to release the hemostatic agent over a time period ranging from about 1 hour to about 168 hours. In some embodiments, the polymer is configured to release the hemostatic agent over a time period ranging from 1 hour to 72 hours. In some embodiments, the polymer is configured to release the hemostatic agent over a time period ranging from 1 hour to 24 hours.

In some embodiments, the polymer is configured to release the hemostatic agent over time in an area surrounding or adjacent to anchorage device 20 (such as, for example, within the device "pocket" or within 3 inches in all dimensions). In some embodiments, the polymer is configured to release the hemostatic agent for up to 30 days. In some embodiments, the polymer is configured to release between about 40% and about 100% of the hemostatic agent over a period of at least about 30 hours. In some embodiments, the polymer is configured to release 60% and about 100% of the hemostatic agent over a period of at least about 30 hours. In some embodiments, the polymer is configured to release between about 65% and about 100% of the hemostatic agent over a period of at least about 36 hours. In some embodiments, the polymer is configured to release 80% and about 100% of the hemostatic agent over a period of at least about 36 hours. In some embodiments, the polymer is configured to release between about 60% and about 100% of the hemostatic agent over a period of at least about 48 hours. In some embodiments, the polymer is configured to release 80% and about 100% of the hemostatic agent over a period of at least about 48 hours. In some embodiments, the polymer is configured to release between about 60% and about 100% of the hemostatic agent over a period of at least about 60 hours. In some embodiments, the polymer is configured to release 80% and about 100% of the hemostatic agent over a period of at least about 60 hours. In some embodiments, the polymer is configured to release 80% and about 100% of the hemostatic agent within 48 hours. In some embodiments, the polymer is configured to release 80% and about 100% of the hemostatic agent within 24 hours.

In some embodiments, the polymer is configured to release no more than 60% of the hemostatic agent within 24 hours. In some embodiments, the polymer is configured to release no more than 90% of the hemostatic agent after 60 hours. In some embodiments, the polymer is configured to release no more than 50% of the hemostatic agent within 12 hours. In some embodiments, the polymer is configured to release between about 40% and about 90% between 12 and 24 hours. In some embodiments, the polymer is configured to release between about 60% and about 100% between 24 and 36 hours. In some embodiments, the polymer is configured to release between about 65% and about 100% between 36 and 48 hours. In some embodiments, the polymer is configured to release between about 70% and about 100% between 48 and 60 hours.

Substrate 22 may be coated with single or multiple coating layers of the polymer, depending on, for example, the amount of the hemostatic agent to be delivered and desired release rate. Each layer of the polymer may contain the same or different amounts of the hemostatic agent. For example, a first layer of the polymer may contain the hemostatic agent, while the second layer of the polymer contains either no the hemostatic agent or a lower concentration of the hemostatic agent. As another example, a first layer of the polymer may comprise the hemostatic agent in a first polymer, while the second layer of the polymer comprises the hemostatic agent in a second polymer that is different than the first polymer.

In some embodiments, a first polymer can be applied to side 28 and a second polymer can be applied to side 30. In some embodiments, the first and second polymers are different polymers. In some embodiments, the first and second polymers release the hemostatic agent at different rates and/or over different lengths of time. In some embodiments, the first and second polymers are different polymers, and the first polymer includes a first amount of the hemostatic agent and the second polymer includes a second amount of the hemostatic agent, the first amount being different than the second amount. In some embodiments, the first and second polymers are the same polymer, wherein the first polymer includes a first amount of the hemostatic agent and the second polymer includes a second amount of the hemostatic agent, the first amount being different than the second amount. In some embodiments, a first polymer is applied to the outer surfaces of sides 28, 30 and a second polymer is applied to the inner surfaces of sides 28, 30, wherein the first polymer includes a first amount of the hemostatic agent and the second polymer includes a second amount of the hemostatic agent, the first amount being different than the second amount. In some embodiments, the first amount is more than the second amount. In some embodiments, the first amount is less than the second amount.

Active Pharmaceutical Ingredient(s)

In some embodiments, anchorage device 20 includes an ingredient, such as, for example, an active pharmaceutical ingredient. The active pharmaceutical ingredient is applied to substrate 22 to such that anchorage device 20 delivers the hemostatic agent in combination with the active pharmaceutical ingredient. In some embodiments, the active pharmaceutical ingredient is applied directly to substrate 22. That is, the active pharmaceutical ingredient is not applied to substrate 22 in a polymer, such as, for example, a polymer that includes the active pharmaceutical ingredient. In some embodiments, the active pharmaceutical ingredient is applied to substrate 22 via a polymer, such as, for example, one of the polymers discussed herein, wherein the polymer includes the active pharmaceutical ingredient and releases active pharmaceutical agent 26 as the polymer degrades. In some embodiments, the active pharmaceutical ingredient is applied to substrate 22 via a polymer that includes the hemostatic agent. In some embodiments, the active pharmaceutical ingredient is applied to substrate 22 via a polymer that does not include the hemostatic agent, such as, for example, a polymer that is free of the hemostatic agent.

The active pharmaceutical ingredient can include one or a combination of active pharmaceutical ingredients, such as, for example, anesthetics, antibiotics, anti-inflammatory agents, procoagulant agents, fibrosis-inhibiting agents, anti-scarring agents, antiseptics, leukotriene inhibitors/antagonists, cell growth inhibitors and mixtures thereof. In some embodiments, the active pharmaceutical ingredient is an antibiotic. In some embodiments, the antibiotic is selected from the group consisting of rifampin and minocycline and mixtures thereof.

Examples of non-steroidal anti-inflammatories include, but are not limited to, naproxen, ketoprofen, ibuprofen as well as diclofenac; celecoxib; sulindac; diflunisal; piroxicam; indomethacin; etodolac; meloxicam; r-flurbiprofen; mefenamic; nabumetone; tolmetin, and sodium salts of each of the foregoing; ketorolac bromethamine; ketorolac bromethamine tromethamine; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, l, and racemic isomers); and the methyl, ethyl, propyl, isopropyl, n-butyl, sec-butyl, t-butyl, esters of acetylsalicylic acid.

Examples of anesthetics include, but are not limited to, licodaine, bupivacaine, and mepivacaine. Further examples of analgesics, anesthetics and narcotics include, but are not limited to acetaminophen, clonidine, benzodiazepine, the benzodiazepine antagonist flumazenil, lidocaine, tramadol, carbamazepine, meperidine, zaleplon, trimipramine maleate, buprenorphine, nalbuphine, pentazocain, fentanyl, propoxyphene, hydromorphone, methadone, morphine, levorphanol, and hydrocodone. Local anesthetics have weak antibacterial properties and can play a dual role in the prevention of acute pain and infection.

Examples of antibacterial agents or antimicrobials include, but are not limited to, triclosan, chlorohexidine and other cationic biguanides, rifampin, minocycline (or other tetracycline derivatives), vancomycin, gentamycin; gendine; genlenol; genfoctol; clofoctol; cephalosporins and the like. Further antibacterial agents or antimicrobials include aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; hexachlorophene; cefamandole nafate; cefepime and its hydrochloride, sulfate, and phosphate salt; cefdinir and its sodium salt; ceftriaxone and its sodium salt; cefixime and its sodium salt; cetylpyridinium chloride; ofoxacin; linexolid; temafloxacin; fleroxacin; enoxacin; gemifloxacin; lomefloxacin; astreonam; tosufloxacin; clinafloxacin; cefpodoxime proxetil; chloroxylenol; methylene chloride, iodine and iodophores (povidone-iodine); nitrofurazone; meropenem and its sodium salt; imipenem and its sodium salt; cilastatin and its sodium salt; azithromycin; clarithromycin; dirithromycin; erythromycin and hydrochloride, sulfate, or phosphate salts ethylsuccinate, and stearate forms thereof, clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; vancomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; α-terpineol; thymol; taurinamides; nitrofurantoin; silver-sulfadiazine; hexetidine; methenamine; aldehydes; azylic acid; silver; benzyl peroxide; alcohols; carboxylic acids; salts; nafcillin; ticarcillin and its disodium salt; sulbactam and its sodium salt; methylisothiazolone, moxifloxacin; amifloxacin; pefloxacin; nystatin; carbepenems; lipoic acids and its derivatives; beta-lactams antibiotics; monobactams; aminoglycosides; microlides; lincosamides; glycopeptides; tetracyclines; chloramphenicol; quinolones; fucidines; sulfonamides; macrolides; ciprofloxacin; ofloxacin; levofloxacins; teicoplanin; mupirocin; norfloxacin; sparfloxacin; ketolides; polyenes; azoles; penicillins; echinocandines; nalidixic acid; rifamycins; oxalines; streptogramins; lipopeptides; gatifloxacin; trovafloxacin mesylate; alatrofloxacin mesylate; trimethoprims; sulfamethoxazole; demeclocycline and its hydrochloride, sulfate, or phosphate salt; doxycycline and its hydrochloride, sulfate, or phosphate salt; minocycline and its hydrochloride, sulfate, or phosphate salt; tetracycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; and clarithromycin (and combinations thereof). In some embodiments, the polymer may contain rifampin and another antimicrobial agent, such as, for example, an antimicrobial agent that is a tetracycline derivative. In some embodiments, the polymer contains a cephalosporin and another antimicrobial agent. In some embodiments, the polymer contains combinations including rifampin and minocycline, rifampin and gentamycin, and rifampin and minocycline.

When a mixture of two antibiotics is used, they generally present in a ratio ranging from about 10:1 to about 1:10. In some embodiments, a mixture of rifampin and minocycline are used. In those embodiments, a ratio of rifampin to minocycline ranges from about 5:2 to about 2:5. In other embodiments, the ratio of rifampin to minocycline is about 1:1.

Examples of antifungals include amphotericin B; pyrimethamine; flucytosine; caspofungin acetate; fluconazole; griseofulvin; terbinafine and its hydrochloride, sulfate, or phosphate salt; amorolfine; triazoles (Voriconazole); flutrimazole; cilofungin; LY303366 (echinocandines); pneumocandin; imidazoles; omoconazole; terconazole; fluconazole; amphotericin B, nystatin, natamycin, liposomal amptericin B, liposomal nystatins; griseofulvin; BF-796; MTCH 24; BTG-137586; RMP-7/Amphotericin B; pradimicins; benanomicin; ambisome; ABLC; ABCD; Nikkomycin Z; flucytosine; SCH 56592; ER30346; UK 9746; UK 9751; T 8581; LY121019; ketoconazole; micronazole; clotrimazole; econazole; ciclopirox; naftifine; and itraconazole.

In some embodiments, the active pharmaceutical ingredient includes keflex, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proline, melphalan, penicillin V, aspirin, nicotinic acid, chemodeoxycholic acid, chlorambucil, paclitaxel, sirolimus, cyclosporins, 5-fluorouracil and the like.

In some embodiments, the active pharmaceutical ingredient includes one or more ingredients that act as angiogenesis inhibitors or inhibit cell growth such as epidermal growth factor, PDGF, VEGF, FGF (fibroblast growth factor) and the like. These ingredients include anti-growth factor antibodies (neutrophilin-1), growth factor receptor-specific inhibitors such as endostatin and thalidomide. Examples of useful proteins include cell growth inhibitors such as epidermal growth factor.

Examples of anti-inflammatory compounds include, but are not limited to, anecortive acetate; tetrahydrocortisol, 4,9(11)-pregnadien-17a, 21-diol-3,20-dione and its -21-acetate salt; 111-epicortisol; 17α-hydroxyprogesterone; tetrahydrocortexolone; cortisona; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its -21-acetate, -21-disodium phosphate, and -21-hemisuccinate forms; triamcinolone benetonide; triamcinolone hexacetonide; fluocinolone and fluocinolone acetate; dexamethasone and its -21-acetate, -21-(3,3-dimethylbutyrate), -21-phosphate disodium salt, -21-diethylaminoacetate, -21-isonicotinate, -21-dipropionate, and -21-palmitate forms; betamethasone and its -21-acetate, -21-adamantoate, -17-benzoate, -17,21-dipropionate, -17-valerate, and -21-phosphate disodium salts; beclomethasone; beclomethasone dipropionate; diflorasone; diflorasone diacetate; mometasone furoate; and acetazolamide.

Examples of leukotriene inhibitors/antagonists include, but are not limited to, leukotriene receptor antagonists such as acitazanolast, iralukast, montelukast, pranlukast, verlukast, zafirlukast, and zileuton.

In some embodiments, the active pharmaceutical ingredient includes sodium 2-mercaptoethane sulfonate ("MESNA"). MESNA has been shown to diminish myofibroblast formation in animal studies of capsular contracture with breast implants [Ajmal et al. (2003) Plast. Reconstr. Surg. 112:1455-1461] and may thus act as an anti-fibrosis agent.

Procoagulants include, but are not limited to, zeolites, thrombin, and coagulation factor concentrates.

In some embodiments, the amount of the active pharmaceutical ingredient that is applied to substrate 22 ranges between about 0.3 to about 2.8 micrograms/cm$^2$. In other embodiments, the amount of the active pharmaceutical ingredient that is applied to substrate 22 ranges between about 0.6 to about 1.4 micrograms/cm$^2$. In yet other embodiments, the amount of the active pharmaceutical ingredient that is applied to substrate 22 ranges between about 0.85 to about 1.20 micrograms/cm$^2$. In yet further embodiments, the amount of the active pharmaceutical ingredient that is applied to substrate 22 ranges between about 0.90 to about 1.10 micrograms/cm$^2$. In yet further embodiments, the amount of the active pharmaceutical ingredient that is applied to substrate 22 ranges between about 50 to about 150 micrograms/cm$^2$. In yet further embodiments, the amount of the active pharmaceutical ingredient that is applied to substrate 22 ranges between about 62 to about 140 micrograms/cm$^2$. In yet further embodiments, 62 micrograms/cm$^2$ of the active pharmaceutical ingredient is applied to substrate 22. In yet further embodiments, 140 micrograms/cm$^2$ of the active pharmaceutical ingredient is applied to substrate 22.

In other embodiments, the active pharmaceutical ingredient includes rifampin and minocycline and the amount of each of rifampin and minocycline that is applied to substrate 22 ranges between about 0.6 to about 1.4 micrograms/cm$^2$. In yet other embodiments, the amount of each of rifampin and minocycline that is applied to substrate 22 ranges between about 0.85 to about 1.20 micrograms/cm$^2$. In yet further embodiments, the amount of each of rifampin and minocycline that is applied to substrate 22 ranges between about 0.90 to about 1.10 micrograms/cm$^2$.

The active pharmaceutical ingredient may include any of the active pharmaceutical ingredients discussed herein. The active pharmaceutical ingredient may be incorporated into anchorage device 20 by applying the active pharmaceutical ingredient directly to substrate 22 or by applying the active pharmaceutical ingredient to substrate 22 via a polymer, such as, for example, one or more of the polymers discussed herein. Doses of the active pharmaceutical ingredients discussed herein are known and the amounts of any single active pharmaceutical ingredient to include in anchorage device 20 can readily be surmised. Any pharmaceutically acceptable form of the active pharmaceutical ingredients discussed herein can be employed in anchorage device 20, e.g., the free base or a pharmaceutically acceptable salt or ester thereof. Pharmaceutically acceptable salts, for instance, include sulfate, lactate, acetate, stearate, hydrochloride, tartrate, maleate, citrate, phosphate and the like.

In some embodiments, the active pharmaceutical ingredient is applied directly to substrate 22, as discussed herein. In some embodiments, the active pharmaceutical ingredient may be applied to substrate 22 by spraying the active pharmaceutical ingredient onto substrate 22, coating all or a portion of substrate 22 with the active pharmaceutical ingredient, coating all or a portion of substrate 22 with a material, such as, for example, one or more polymer that includes the active pharmaceutical ingredient, washing substrate 22 with the active pharmaceutical ingredient, or printing the active pharmaceutical ingredient on substrate 22 with a printer, such as, for example a 3D printer. In some embodiments, the active pharmaceutical ingredient is a material that forms substrate 22. That is, substrate 22 is made from the active pharmaceutical ingredient and the hemostatic agent is applied to substrate 22.

In some embodiments, the active pharmaceutical ingredient is positioned between the hemostatic agent and substrate 22. As such, the hemostatic agent forms a top layer of anchorage device 20 and is eluted or released before the active pharmaceutical ingredient is eluted or released. That is, the active pharmaceutical ingredient is eluted or released after all of the hemostatic agent is eluted or released. In some embodiments, substrate 22 is made from the hemostatic agent and the active pharmaceutical ingredient is applied to substrate 22. In some embodiments, the hemostatic agent is positioned between the active pharmaceutical ingredient and substrate 22. As such, the active pharmaceutical ingredient forms a top layer of anchorage device 20 and is eluted or released before active the hemostatic agent is eluted or released. That is, the hemostatic agent is eluted or released after all of the active pharmaceutical ingredient is eluted or released.

In some embodiments, the active pharmaceutical ingredient can be applied to at least one of sides 28, 30. In some embodiments, only one of sides 28, 30 includes the active pharmaceutical ingredient. In some embodiments, the active pharmaceutical ingredient is applied only to the outer surfaces of sides 28, 30. That is, the inner surfaces of sides 28, 30 that define cavity C do not have the active pharmaceutical ingredient applied thereto. In some embodiments, the active pharmaceutical ingredient is applied only to the inner surfaces of sides 28, 30. That is, the outer surfaces of sides 28, 30 do not have the active pharmaceutical ingredient applied thereto. In some embodiments, the active pharmaceutical ingredient is applied only to the inner surface of one of sides 28, 30 and to the outer surface of the other one of sides 28, 30.

In some embodiments, a first active pharmaceutical ingredient can be applied to side 28 and a second active pharmaceutical ingredient can be applied to side 30, wherein the second the active pharmaceutical ingredient is different than the first the active pharmaceutical ingredient. In some embodiments, a first the active pharmaceutical ingredient is applied to the outer surfaces of sides 28, 30 and a second the active pharmaceutical ingredient is applied to the inner surfaces of sides 28, 30, wherein the second the active pharmaceutical ingredient is different than the first the active pharmaceutical ingredient.

In some embodiments, a first polymer can be applied to one of sides 28, 30 and a second polymer can be applied to the other one of sides 28, 30. In some embodiments, the first and second polymers are the same polymer. In some embodiments, the first and second polymers are different polymers. In some embodiments, the first and second polymers each include the hemostatic agent and the active pharmaceutical ingredient, wherein one of the first and second polymers includes more of the hemostatic agent than the other of the first and second polymers and the polymer that includes more of the hemostatic agent includes less of the active pharmaceutical ingredient than the other polymer. In some embodiments, the first polymer includes the hemostatic agent and the second polymer includes the active pharmaceutical ingredient. In some embodiments, one of the first and second polymers includes the hemostatic agent and the active pharmaceutical ingredient and the other of the first and second polymers includes only the hemostatic agent. In some embodiments, one of the first and second polymers includes the hemostatic agent and the active pharmaceutical ingredient and the other of the first and second polymers includes only the active pharmaceutical ingredient. In some embodiments, one of the first and second polymers includes the hemostatic agent and the active pharmaceutical ingredient and the other of the first and second polymers does not include the hemostatic agent or the active pharmaceutical ingredient. In some embodiments, at least one of the first and second polymers includes a plurality of discrete layers, such as, for example, a first layer, a second layer, a third layer, a fourth layer, a fifth layer, etc. In some embodiments, the layers each include different polymers.

In some embodiments, the layers each include the same polymer. In some embodiments, the contents of the layers alternate. For example, in some embodiments, the first layer includes the hemostatic agent, the second layer includes active pharmaceutical agent 26, the third layer includes the hemostatic agent, the fourth layer includes active pharmaceutical agent 26 and the fifth layer includes the hemostatic agent, wherein the layers that include the hemostatic agent do not include the active pharmaceutical ingredient and the layers that include the active pharmaceutical ingredient do not include the hemostatic agent. In some embodiments, the layers each include the hemostatic agent, wherein the amount of the hemostatic agent in each layer is the same or different In some embodiments, the layers each include the active pharmaceutical ingredient, wherein the amount of the active pharmaceutical ingredient in each layer is the same or different. In some embodiments, the layers each include the hemostatic agent and the active pharmaceutical ingredient, wherein the amount of the hemostatic agent and/or the active pharmaceutical ingredient in each layer is the same or different.

In some embodiments, a first polymer can be applied to side 28 and a second polymer can be applied to side 30. In some embodiments, the first and second polymers are different polymers. In some embodiments, the first and second polymers release the hemostatic agent and/or the active pharmaceutical ingredient at different rates and/or over different lengths of time. In some embodiments, the first and second polymers are different polymers, and the first polymer includes a first amount of the hemostatic agent and/or the active pharmaceutical ingredient and the second polymer includes a second amount of the hemostatic agent and/or the active pharmaceutical ingredient, the first amount being different than the second amount. In some embodiments, the first and second polymers are the same polymer, wherein the first polymer includes a first amount of the hemostatic agent and/or the active pharmaceutical ingredient and the second polymer includes a second amount of the hemostatic agent and/or the active pharmaceutical ingredient, the first amount being different than the second amount. In some embodiments, a first polymer is applied to the outer surfaces of sides 28, 30 and a second polymer is applied to the inner surfaces of sides 28, 30, wherein the first polymer includes a first amount of the hemostatic agent and/or the active pharmaceutical ingredient and the second polymer includes a second amount of the hemostatic agent and/or the active pharmaceutical ingredient, the first amount being different than the second amount. In some embodiments, the first amount is more than the second amount. In some embodiments, the first amount is less than the second amount.

In some embodiments, the hemostatic agent and/or the active pharmaceutical ingredient is/are configured to elute/release from anchorage device 20 into an area surrounding or adjacent to anchorage 20 to reduce or stop bleeding and/or reduce the amount of associated post-surgical complications that can occur with such implantable medical devices, such as, for example, post-implant infection, pain, excessive scar tissue formation and shrinkage of the prosthesis or mesh, excessive scar tissue formation, limited patient mobility, and/or chronic pain.

In some embodiments, the hemostatic agent and/or the active pharmaceutical ingredient is configured to elute/release from anchorage device 20 into an area surrounding or adjacent to anchorage 20 to reduce or stop bleeding and/or reduce or prevent surgery-related complications associated with the implantable medical device (such as to the "pocket" surrounding the device). For example, an anesthetic agent can be eluted into the surrounding bodily tissue, bodily fluid, or systemic fluid, to attenuate pain experienced at the implantation site. In another example, replacing the anesthetic agent with an anti-inflammatory agent can reduce the swelling and inflammation associated implantation of the mesh substrate and/or the implantable medical device. In yet another example, an antimicrobial agent can be provided at a rate of drug release sufficient to prevent or reduce colonization of substrate 22, the implantable medical device and/or the surgical implantation site by bacteria, for example, for at least the period following surgery necessary for initial healing of the surgical incision.

Figure 10:
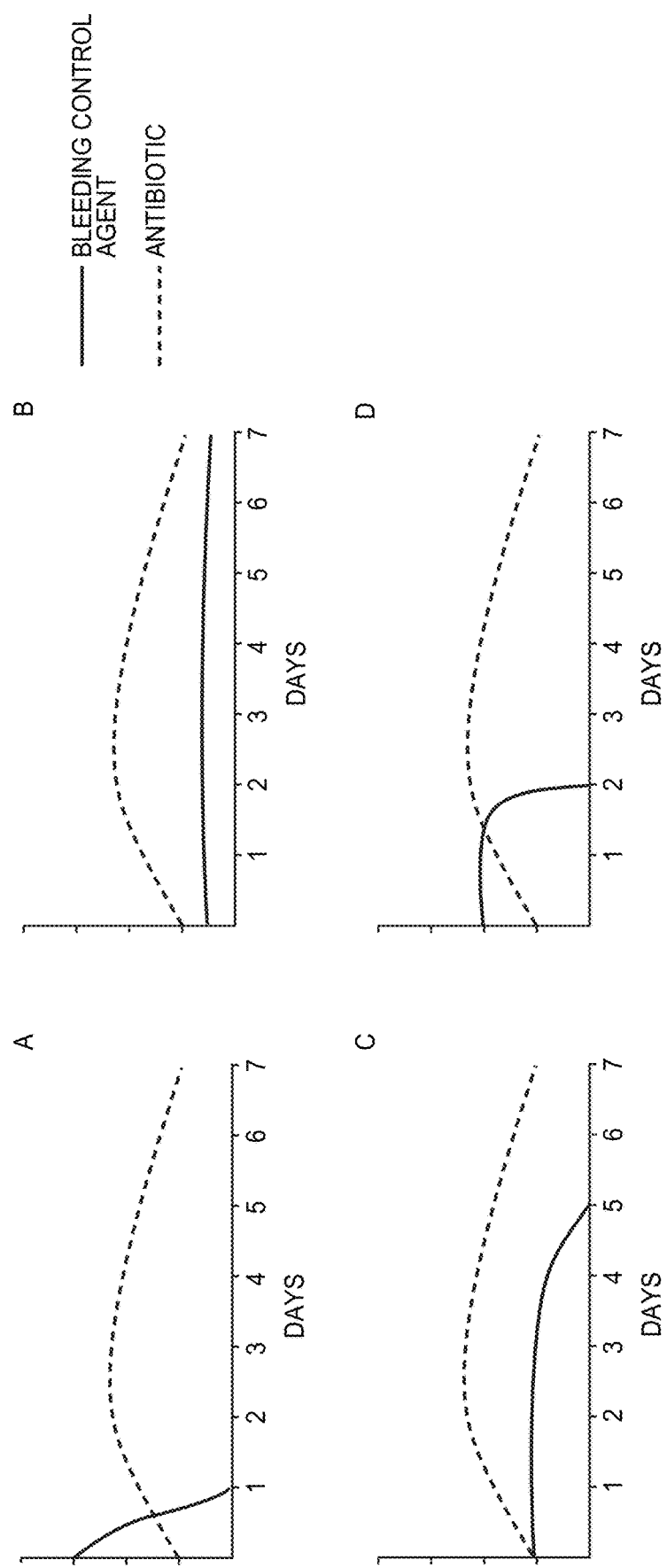
FIG. 10 is a group of graphs showing release rates of a hemostatic agent and an active pharmaceutical ingredient.

The release rates of the hemostatic agent and/or the active pharmaceutical ingredient can be varied, as desired. For example, in some embodiments, the hemostatic agent may only be released for one, two or five days, while the active pharmaceutical ingredient is released over 7 or more days, as shown in FIG. 10. In some embodiments, the hemostatic agent and the active pharmaceutical ingredient are both released for 7 or more days, as also shown in FIG. 11. It is also envisioned that the amount of the hemostatic agent and active pharmaceutical ingredient that is released can vary over time. For example, in some embodiments, a greater amount of the hemostatic agent is released upon implantation of anchorage device 20. In some embodiments, a greater amount of the active pharmaceutical ingredient is released upon implantation of anchorage device 20. In some embodiments, equal amounts of the hemostatic agent and the active pharmaceutical ingredient are released upon implantation of anchorage device 20.

In some embodiments, the hemostatic agent and/or the active pharmaceutical ingredient may be eluted for up to 30 days. In some embodiments, between about 40% and about 100% of the hemostatic agent and/or the active pharmaceutical ingredient is/are released over a period of at least about 30 hours. In some embodiments, 60% and about 100% of the hemostatic agent and/or the active pharmaceutical ingredient is/are released over a period of at least about 30 hours. In some embodiments, between about 65% and about 100% of the hemostatic agent and/or the active pharmaceutical ingredient is/are released over a period of at least about 36 hours. In some embodiments, 80% and about 100% of the hemostatic agent and/or the active pharmaceutical ingredient is/are released over a period of at least about 36 hours. In some embodiments, between about 60% and about 100% of the hemostatic agent and/or the active pharmaceutical ingredient is/are released over a period of at least about 48 hours. In some embodiments, 80% and about 100% of the hemostatic agent and/or the active pharmaceutical ingredient is/are released over a period of at least about 48 hours. In some embodiments, between about 60% and about 100% of the hemostatic agent and/or the active pharmaceutical ingredient is/are released over a period of at least about 60 hours. In some embodiments, 80% and about 100% of the hemostatic agent and/or the active pharmaceutical ingredient is/are released over a period of at least about 60 hours.

In some embodiments, anchorage device 20 includes a hydrophilic component, such as, for example, PEG and a crosslinking agent that is applied to substrate 22. The hydrophilic component and the crosslinking agent form a hydrogel that absorbs blood and reduces bleeding when in contact with blood or tissue fluid. In some embodiments, the hydrophilic component and the crosslinking agent are sprayed directly onto substrate 22. In some embodiments, the hydrophilic component and the crosslinking agent are provided in a polymer, such as, for example, one or more of the polymers discussed herein, and the polymer is applied directly onto substrate 22. In some embodiments, the hydrophilic component and the crosslinking agent are provided in a patch, such as, for example, the Veriset™ haemostatic patch available from Medtronic, Inc., and the patch is applied directly onto substrate 22. In some embodiments, the patch comprises a plurality of layers. For example, a first layer of the patch can include a hemostatic agent, such as, for example, oxidized regenerated cellulose and/or one or more of the hemostatic agents discussed herein. A second layer of the patch can include a crosslinking agent, such as, for example, trilysine and/or one or more of the crosslinking agents discussed herein. A third layer of the patch can include a hydrophilic agent, such as, for example, PEG and/or one or more of the hydrophilic agents discussed herein. The second layer of the patch is positioned between the first and third layers of the patch.

In some embodiments, the hydrophilic component comprises thermogelling hydrogels, PEG -PLGA copolymers, PEG -Poly(N-isopropyl acrylamide), Pluronic (PEO-PPO-PEO triblock), PEG-PCL polymers, PEG-based amphiphilic copolymers modified by anionic weak polyelectrolytes, (such as polyacrylic acid, polyglutamic acid) and polymers containing sulfonamide groups), PEG-based amphiphilic copolymers modified by cationic weak polyelectrolytes (such as poly (2-vinyl pyridine), Poly(beta-amino esters), poly (2-(dimethylamino)ethyl methacrylate), multiarm PEG derivatives such as those available from JenKem technology, multiarmed block and graft PLA copolymers with PEG, PEG with stereo complexed poly(lactide), acrylated polymers (such as Polyvinylalcohol, dextran, Polyvinylpyrollidone, chitosan, alginate, hyaluronic acid), and combinations thereof. In some embodiments, the crosslinking agent comprises one or more agents that induce polymerization of vinyl groups using various initiators, light or redox reactions, or by reactions such as Schiff base formation, Michael type additions, peptide ligation, clock chemistry of functional groups present; one or more agents that induce crosslinking by enzymatic reaction (transglutaminase mediated reaction between carboxamide and amine on proteins), stereo-complexation, metal chelation (alginates using calciumCal2), thermogelation, self-assembly (formation of super helices from protein chains) inclusion complexation (using cyclodextrin); and combinations thereof.

Methods

In some embodiments, an anchorage device, such as, for example, anchorage device 20 is produced having a desired size from a single substrate 22, as discussed herein. A medical device, such as, for example, one of the implantable medical devices discussed herein is implanted into a body of a patient with the anchorage device. The anchorage device releases a hemostatic agent, such as, for example, the hemostatic agent to reduce or prevent bleeding within the patient. In some embodiments, the anchorage device also releases an active pharmaceutical agent, such as, for example, the active pharmaceutical ingredient to prevent, mitigate, or treat a condition within the patient, such as, for example, a bacterial infection. In some embodiments, the anchorage device releases the hemostatic agent before the active pharmaceutical ingredient. In some embodiments, the anchorage device releases the hemostatic agent after the active pharmaceutical ingredient. In some embodiments, the anchorage device releases the hemostatic agent and the active pharmaceutical ingredient simultaneously. In some embodiments, the anchorage device releases the hemostatic agent and/or the active pharmaceutical ingredient upon implantation of the anchorage device. In some embodiments, the anchorage device releases the hemostatic agent and the active pharmaceutical ingredient in alternating sequences. In some embodiments, the anchorage device is implanted within the patient without the medical device and the medical device is coupled to or inserted into the anchorage device after the anchorage device is implanted. In some embodiments, the medical device is coupled to or inserted into the anchorage device before the anchorage device is implanted within the patient and the anchorage device and the medical device are implanted within the patient together.

In some embodiments, the implantable medical device is removed from the patient after the treatment is completed. In some embodiments, the anchorage device remains implanted within the patient after the implantable medical device is removed. In some embodiments, the anchorage device is removed from the patient after the implantable medical device is removed. To remove the anchorage device, tissue that is ingrown within the substrate of the anchorage device can be cut or otherwise detached from the substrate. In some embodiments, a portion of the anchorage device may not be removable from the tissue and will remain implanted within the patient.

Kits

In some embodiments, kits are provided that include one or a plurality of anchorage devices, such as, for example, anchorage devices 20. It is contemplated that each of the anchorage devices included can have a different configuration. In some embodiments, the anchorage devices can include different hemostatic agents, such as, for example, the hemostatic agent and/or different active pharmaceutical ingredients, such as, for example, different active pharmaceutical ingredients. In some embodiments, the anchorage devices can include different amounts of a hemostatic agent, such as, for example, the hemostatic agent and/or different amounts of an active pharmaceutical ingredient, such as, for example, different active pharmaceutical ingredients. In some embodiments, the anchorage devices can include different sizes. In some embodiments, the anchorage devices can include different shapes. In some embodiments, the anchorage devices can include different anchorage devices that are designed for use with different medical devices, such as, for example, the implantable or non-implantable medical devices discussed herein. In some embodiments, the kits include one or a plurality of medical devices, such as, for example, the implantable or non-implantable medical devices discussed herein. In some embodiments, the kit includes tools for customizing the anchorage device, such as, for example, a knife, scissor, or blade for severing a portion of the substrate from another portion of the substrate. In some embodiments, the kit includes a blank substrate that does not include any of the bonding areas discussed herein. The kit also includes the adhesives and nonstick materials discussed herein so that bonding areas can be created on the blank substrate at selected areas to make a pocket having a selected size to fit a specific implantable medical device, for example. In some embodiments, the kit includes instructions for use.

Example 1

In one example, an anchorage device having a substrate, such as, for example, one of the substrates discussed above was prepared. 5 g of Chitosan (HMW, Sigma MKBP1333V) was dissolved in a mixture of 460 mL distilled water and 40 mL 1M HCl. 10 mL of the viscous solution was poured into a Teflon petri dish and placed in a hood. After 24 h, the composition was dry to touch. It was then placed in a 50° C. oven under vacuum for 24 h. An equivalent procedure was used to prepare substrates from other materials. Details are given in Table A below.

TABLE A

| # | Agent | Supplier Lot # | Weight | Solvent | Result |
|---|---|---|---|---|---|
| 1 | Chitosan | Sigma MKBP1333V | 5 g | 460 mL water + 40 mL 1M HCl | Continuous film |
| 2 | PEG 20K | Fluka, 1303367 | 12.5 g | 25 mL Dichloromethane | No film |
| 3 | Poly-vinyl-pyrollidone (PVP) | ISP Technologies, 0550149110 | 5 g | 15 mL water + 2 mL 1M HCl | Film |
| 4 | Jello | Sugar Free strawberry flavor | 0.350 g | 5 mL water | Film |
| 5 | PEG 20K + Jello | | | 1:1 mix of 1 and 5 | No Film |

Example 2

In another example, a hemostatic coated mesh substrate was prepared. A knitted multifilament mesh was taped down on a flat Teflon sheet. Prepared hemostat solutions described above were poured onto the mesh and spread using a Gardner Knife. The compositions were allowed to dry overnight in the hood and then at 50° C. under vacuum for 24 hours. Chitosan and PVP solutions and a 1:1 mixture of Chitosan and PVP were used to prepare hemostat coated meshes.

Hemostatic properties of the anchorage devices prepared in Examples 1 and 2 were observed. Water absorption was used as the initial screening test for hemostatic properties. A commercial hemostat Surgifoam was used as the control. Not wetted Surgifoam does not soak water easily, but wetted one works as a sponge. A piece of the hemostatic composition was placed on a flat Teflon surface. 3 drops of water were placed in the center of the composition and the time for water to absorb and the physical state of the hemostats were observed. Results are shown in FIG. 12.

Example 3

In another example, an anchorage device was prepared wherein the anchorage device had an active pharmaceutical ingredients, such as, for example, at least one antimicrobial agent was applied to a substrate, such as for example, a hemostatic mesh. A sheet of organic regenerated cellulose (ORC) made from multifilament fibers was stretched over a rectangular frame (10 inches×13 inches). This was coated with a 4% Weight by volume solution containing Rifampin, minocycline and tyrosine polyarylate (15:15:70 by weight) dissolved in THF:Methanol (9:1 V/V) using an ultrasonic spraying machine (Ultrasonic Systems, Inc., Haverhill, Mass.). The coated mesh was dried under vacuum for 24 h at 50 C.

Example 4

In another example, an agent, such as, for example, at least one of the active pharmaceuticals discussed herein was selectively applied to a substrate of an anchorage device. Different patterns were created on an ORC sheet (made from multifilament fibers) by masking predetermined areas of the mesh with masking tape. The patterned sheet of ORC was stretched over a rectangular frame (10 inches×13 inches). This was coated with a 4% Weight by volume solution containing Rifampin, minocycline and tyrosine polyarylate (15:15:70 by weight) dissolved in THF:Methanol (9:1 V/V) using an ultrasonic spraying machine (Ultrasonic Systems, Inc., Haverhill, Mass.). The coated mesh was dried under vacuum for 24 h at 50 C. The masking tape was peeled off to create meshes with the predetermined pattern.

Example 5

In another example, an anchorage device having a configuration of a pocket, pouch or envelope discussed above was prepared. Two sheets of the coated synthetic mesh were coated mesh placed one on top of the other and sealed and cut into the shape using an ultrasonic weld. The anvil used in the ultrasonic welding resulted in the formation of a pouch 2.5"×2.75" in size, sealed on approximately 3 and one-half sides. By changing the size and shape of the anvil, pouches of different sizes and shapes can be made.

Example 6

In another example, an agent, such as, for example, at least one of the hemostatic agents discussed herein was prepared to be applied to a substrate of an anchorage device, such as, for example, one of the substrates discussed herein. A 5% solution of chitosan (Aldrich, low molecular weight) was prepared as follows. 5 g of chitosan, 2.5 g of succinic acid were added to 100 mL of distilled water in a 250-mL glass jar containing a magnetic stir bar. The mixture was stirred at 500 rpm until a clear viscous solution was obtained.

Example 7

In another example, an agent, such as, for example, at least one of the hemostatic agents discussed herein was applied to a substrate of an anchorage device, such as, for example, one of the pockets, pouches or envelopes discussed herein. A piece of Tyvek (blown PTFE) film (size equal to that of the inner dimensions of the envelope) was placed within the envelope. The envelope was placed on a flat sheet of Teflon. About 10 mL of the hemostat solution was poured on the envelope and spread using a polypropylene rod. After drying for 24 hours under the hood, the envelope was removed, excess hemostat was trimmed off and the inner Teflon sleeve was removed. This resulted in the hemostatic agent being applied to one side of the envelope. That is, the other side of the envelope did not include the hemostatic agent.

Example 8

In another example, an agent, such as, for example, at least one of the hemostatic agents discussed herein was applied to a substrate of an anchorage device, such as, for example, one of the pockets, pouches or envelopes discussed herein. The envelope was mounted on a plastic mandrel, which was then dipped into the viscous solution of hemostat. Excess solution was allowed to drain. The mandrel was dried under vacuum at 80 C for 36 hours. After cooling, the envelope was removed from the mandrel. This resulted in the hemostatic agent being applied to both sides of the envelope.

Example 9

In another example, an anchorage device having a configuration of a pocket, pouch or envelope discussed above was prepared. The envelopes were made from one or more sheets comprising a hemostatic agent and a mesh material that is coated with an antibiotic, such as, for example at least one of the antibiotics discussed herein. The devices may be created from hemostatic sheets and synthetic mesh by fusing them using heat, ultrasonic energy or solvent, polymeric solutions or glue, as discussed below.

Figure 13:
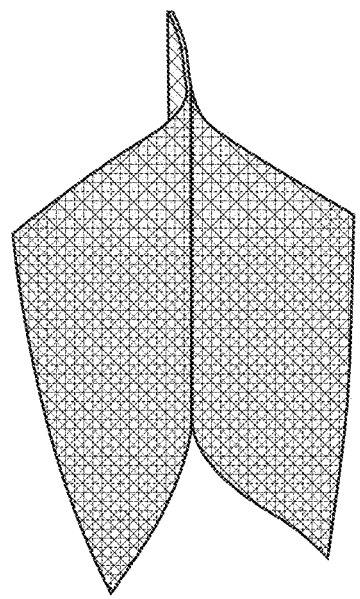
FIG. 13 is a perspective view of an anchorage device discussed in Example 9 in accordance with the principles of the present disclosure.

Heat:

1. In one example, two sheets of ORC mesh coated with tyrosine polymer plus Rifampin and Minocycline were placed within the jaws of a PACWORLD bar sealer (using the following conditions: 7 Sec, 140 C, 80 psi. The sheets were fused together, as discussed herein, and shown in FIG. 13.

Figure 14:
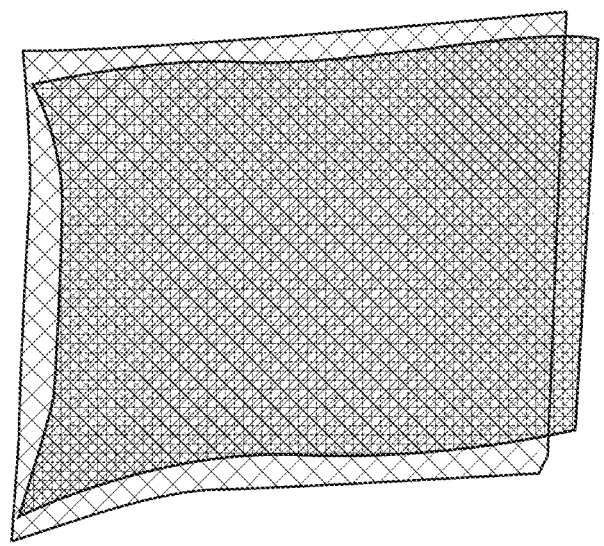
FIG. 14 is a perspective view of an anchorage device discussed in Example 9 in accordance with the principles of the present disclosure.

2. In one example, one sheet of ORC mesh coated with tyrosine polymer, Rifampin and Minocycline and one sheet of biodegradable mesh made from glycolide, caprolactone and trimethylene carbonate coated with tyrosine polymer with Rifampin and Minocycline were placed within the jaws of a PACWORLD bar sealer (using the following conditions: 7 Sec, 140 C, 80 psi. The sheets were fused together, as discussed herein and shown in FIG. 14.

Figure 15:
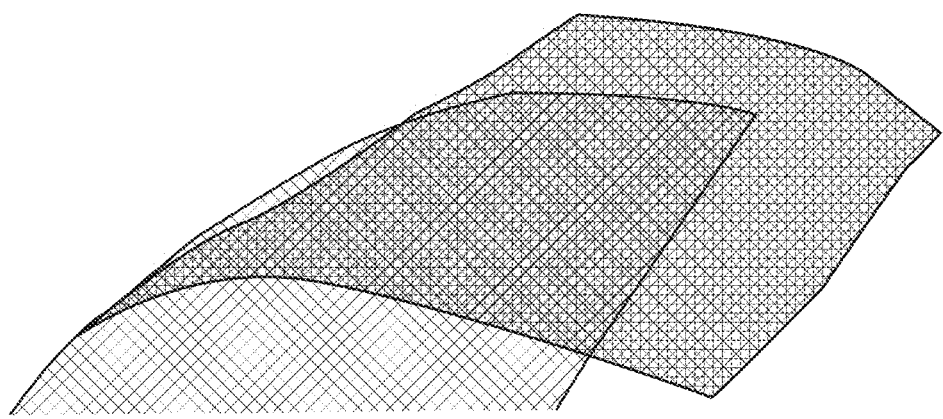
FIG. 15 is a perspective view of an anchorage device discussed in Example 9 in accordance with the principles of the present disclosure.

3. In one example, one sheet of uncoated ORC mesh and one sheet of biodegradable mesh made from glycolide, caprolactone and trimethylene carbonate coated with tyrosine polymer with Rifampin and Minocycline were placed within the jaws of a PACWORLD bar sealer (using the following conditions: 7 Sec, 140 C, 80 psi. The sheets were fused together, as discussed herein and shown in FIG. 15.

Figure 16:
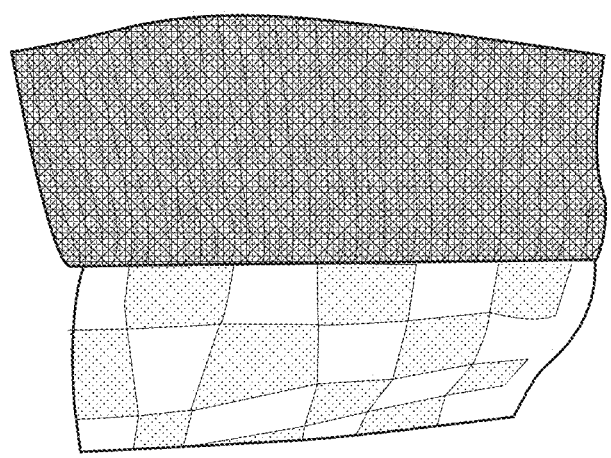
FIG. 16 is a perspective view of an anchorage device discussed in Example 9 in accordance with the principles of the present disclosure.

4. In one example, one sheet of coated ORC mesh coated with tyrosine polymer plus Rifampin and Minocycline in a pattern and one sheet of biodegradable mesh made from glycolide, caprolactone and trimethylene carbonate coated with tyrosine polymer with Rifampin and Minocycline in a pattern were placed within the jaws of a PACWORLD bar sealer (using the following conditions: 7 Sec, 140 C, 80 psi. The sheets were fused together, as discussed herein. The pattern on the ORC mesh sheet is shown in FIG. 16.

Solvent Based

5. In one example, a solution of tyrosine polymer was placed between two sheets of uncoated ORC. The sheets were clamped together. After drying for 36 h under ambient conditions, it was further dried at 80 C for 24 hours. The sheets were fused together, as discussed herein.

6. In one example, two sheets of polymer coated ORC were wetted with DMSO. The sheets were clamped together. After drying for 36 h under ambient conditions, it was further dried at 80 C for 24 hours. The sheets were fused together, as discussed herein.

7. In one example, two sheets of polymer coated ORC was wetted with DMF. The sheets were clamped together. After drying for 36 h under ambient conditions, it was further dried at 80 C for 24 hours. The sheets were fused together, as discussed herein.

Adhesive

8. In one example, a small amount of cyanoacrylate glue was placed between two sheets of uncoated ORC. The sheets were clamped together and dried at room temperature for 1 hour. The sheets were fused together, as discussed herein.

Sewing

9. In one example, two sheets of ORC mesh coated with tyrosine polymer plus Rifampin and Minocycline were sewn together 10. In one example, one sheet of ORC mesh coated with tyrosine polymer, Rifampin and Minocycline and one sheet of biodegradable mesh made from glycolide, caprolactone and trimethylene carbonate coated with tyrosine polymer with Rifampin and Minocycline were sewn together 11. In one example, one sheet of uncoated ORC mesh and one sheet of biodegradable mesh made from glycolide, caprolactone and trimethylene carbonate coated with tyrosine polymer with Rifampin and Minocycline were sewn together 12. In one example, one sheet of coated ORC mesh coated with tyrosine polymer plus Rifampin and Minocycline in a pattern and one sheet of biodegradable mesh made from glycolide, caprolactone and trimethylene carbonate coated with tyrosine polymer with Rifampin and Minocycline in a pattern were sewn together.

13. In one example, one sheet of uncoated ORC mesh and one sheet of biodegradable film made from tyrosine polymer with Rifampin and Minocycline were sewn together.

14. In one example, one sheet of ORC mesh coated with tyrosine polymer plus Rifampin and Minocycline and one sheet of biodegradable film made from tyrosine polymer with Rifampin and Minocycline were sewn together were sewn together.

Example 10

In another example, an agent, such as, for example, at least one of the hemostatic agents discussed herein was selectively applied to a substrate of an anchorage device. A sheet of biodegradable mesh made from glycolide, caprolactone and trimethylene carbonate coated with tyrosine polymer with Rifampin and Minocycline was fixed to a flat surface. Drops of a solution of Chitosan (5% w/v) in water containing succinic acid was applied to the mesh using a syringe. The mesh was dried overnight at room temperature and then at 80° C. under vacuum for 24 h.

Example 11

In another example, agents, such as, for example, at least one of the hemostatic agents discussed herein and at least one of the active pharmaceutical ingredients discussed herein were selectively applied to a substrate of an anchorage device. A 4% Weight by volume solution containing Rifampin, minocycline and tyrosine polyarylate (15:15:70 by weight) dissolved in THF:Methanol (9:1 V/V) was first prepared. Fine particles of a suitable hemostatic agent were suspended in this mixture and the suspension was sprayed onto a suitable mesh substrate. After drying under ambient condition until the coating was dry to the touch, the mesh was dried in a vacuum oven at 80° C. for 24 to 72 hours. The hemostatic agents can be selected from any of the hemostatic agents discussed herein and/or tranexamic acid, amino caproic acid (e.g., epsilon amino caproic acid), aprotinin, natural serine protease inhibitors, or polymers such as ORC or chitosan or other polysaccharides. In some embodiments, the hemostatic agents can include Arista AH hemostat and a desiccant. In some embodiments, the Arista AH hemostat is a hydrophilic, flowable, sterile, fine, dry white powder made by crosslinking purified plant starch through a proprietary process into Microporous Polysaccharide Hemispheres (MPH). In some embodiments, the hemostatic agents can include those discussed by Barnard J, Millner R, "A Review of Topical Hemostatic Agents for Use in Cardiac Surgery," Ann Thorac Surg. 2009, 88: 1377-1383. 10.1016, which is incorporated herein by reference, in its entirety. In some embodiments, the hemostatic agents can include those discussed by Jill Henley, Jerry D. Brewer, "Newer Hemostatic Agents Used in the Practice of Dermatologic Surgery," Dermatology Research and Practice 2013, 1-15, which is incorporated herein by reference, in its entirety. In some embodiments, the hemostatic agents can include those discussed by F. I. Broekema, W. Van Oeveren, J. Zuidema, S. H. Visscher, and R. R. M. Bos, "In vitro analysis of polyurethane foam as a topical hemostatic agent," Journal of Materials Science, vol. 22, no. 4, pp. 1081-1086, 2011, which is incorporated herein by reference, in its entirety.

Example 12

In another example, anchorage devices having a substrate, such as, for example, one of the substrates discussed above were prepared wherein the substrate was made from fibers that include a hemostatic agent, such as, for example, at least one of the hemostatic agents discussed herein, and fibers that do not include a hemostatic agent. In one example, the fibers that include the hemostatic agent are made from an aqueous solution that include the hemostatic agent(s). In some embodiments, an active pharmaceutical ingredient is added to the aqueous solution. In one example, the fibers that do not include the hemostatic agent are coextruded with an active pharmaceutical ingredient, such as, for example, at least one of the active pharmaceutical ingredients discussed herein. The fibers are swelled in some solvent containing the API, such as, for example, polyurethane or silicone in THF. The fibers that include the hemostatic agent and the fibers that do not include the hemostatic agent are dried, and the dried fibers are used to form a mesh. In some embodiments, the fibers that include the hemostatic agent are made as discussed by Pillai, C. K. S.; Paul, W.; Sharma, C. P. Chitin and chitosan polymers: Chemistry, solubility and fiber formation. Prog. Polym. Sci. 2009, 34, 641-678, which is incorporated herein by reference, in its entirety.

Example 13

In another example, an agent, such as, for example, at least one of the active pharmaceuticals discussed herein was applied to a substrate of an anchorage device such that the agent eluted or released from the substrate at a selected rate. The substrate was made from various combinations of Glycoprene®, ORC, polymer-coated Glycoprene® (e.g., one of the tyrosine-derived polymers discussed herein), and polymer-coated ORC (e.g., one of the tyrosine-derived polymers discussed herein). The samples were weighed in 20 mL scintillation vials and then immersed in 20 mL of phosphate buffered saline (pH 7.4). The vials were allowed to shake at 120 rpm in an incubator at 37° C. At various subsequent time points, 1 mL of the buffer was removed for analysis by UPLC. At each time point after 1 mL was removed, the buffer was decanted. The vials were replenished with fresh buffer and returned to the incubator. The volume of fresh buffer was gradually reduced from the initial 20 mL to 10 mL, 5 mL, and 2 mL in order to maintain a concentration that can be detected by UPLC.

Samples of coated ORC and coated Glycoprene® were weighed in 20 mL scintillation vials. Samples were initially dissolved in DMSO and allowed to shake for at least 15 minutes. Then, MeOH was added and vials were allowed to shake for another minimum of 15 minutes. One (1) mL of each solution was then filtered through a 0.45 micron PTFE filter and loaded onto the UPLC for analysis. Results below are reported as a cumulative % released against time.

Substrates, such as, for example, the substrates discussed herein, were prepared, as discussed herein, to include coatings (e.g., polymers) that elute an active pharmaceutical ingredient, such as, for example, at least one of the active pharmaceutical ingredients discussed herein, at different rates. Ten samples were produced (Samples 1-6 and 9-12), as shown in FIG. 17. In the data provided below, "Tyrx" or "TYRX" refers to a degradable polymer, and in particular, to one or more of the tyrosine-derived polymers discussed herein, wherein the polymer includes at least one active pharmaceutical ingredient.

Figure 18:
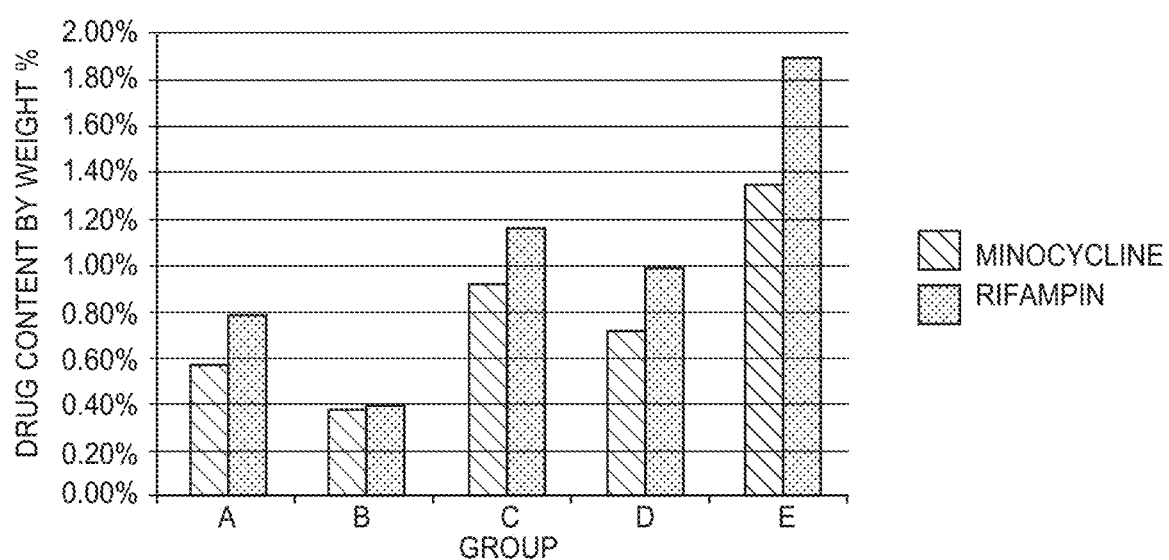
FIG. 18 is a graph showing drug content by weight of anchorages device discussed in Example 13.

The active pharmaceutical ingredient(s) or drug(s) in each of Samples 1-6 and 9-12 is shown in FIG. 18. Further details regarding the substrates used in Samples 1-6 and 9-12 are provided in FIG. 27.

Figure 19A:
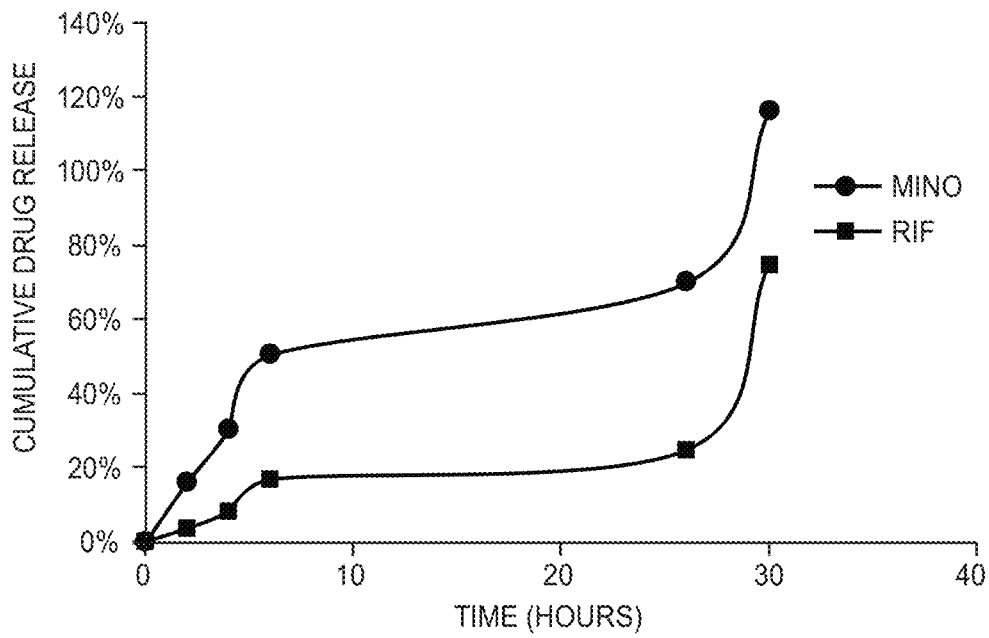
FIG. 19A is a graph showing elution profiles of Samples 1 and 2 discussed in Example 13.
Figure 19B:
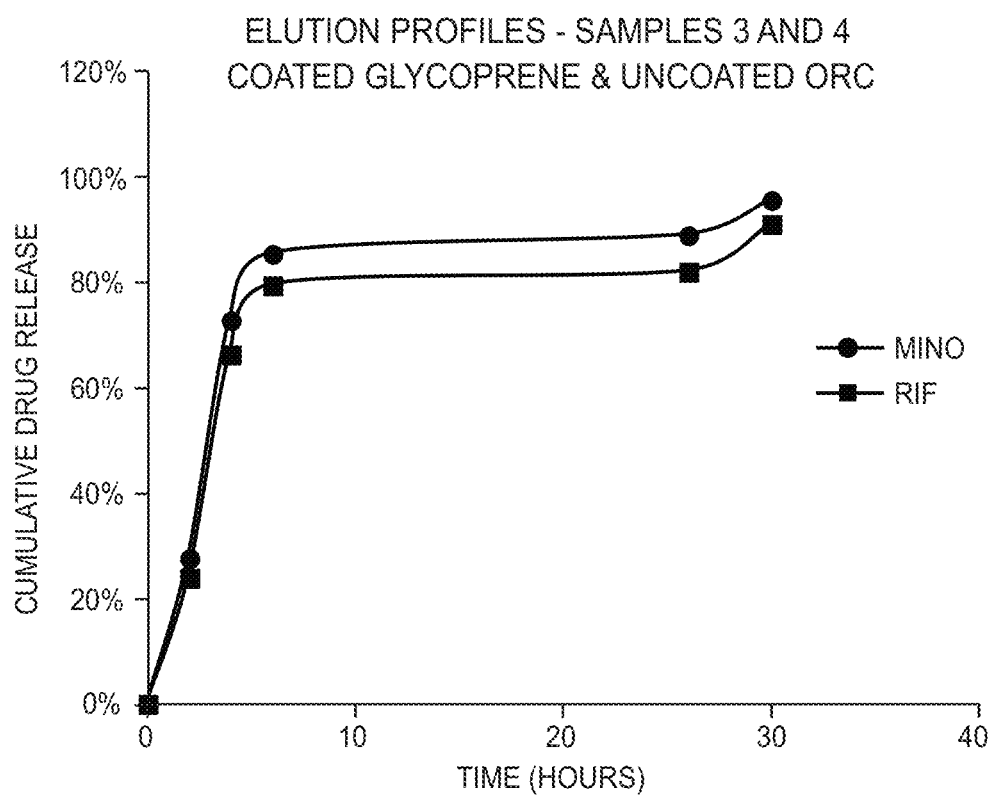
FIG. 19B is a graph showing elution profiles of Samples 3 and 4 discussed in Example 13.
Figure 19C:
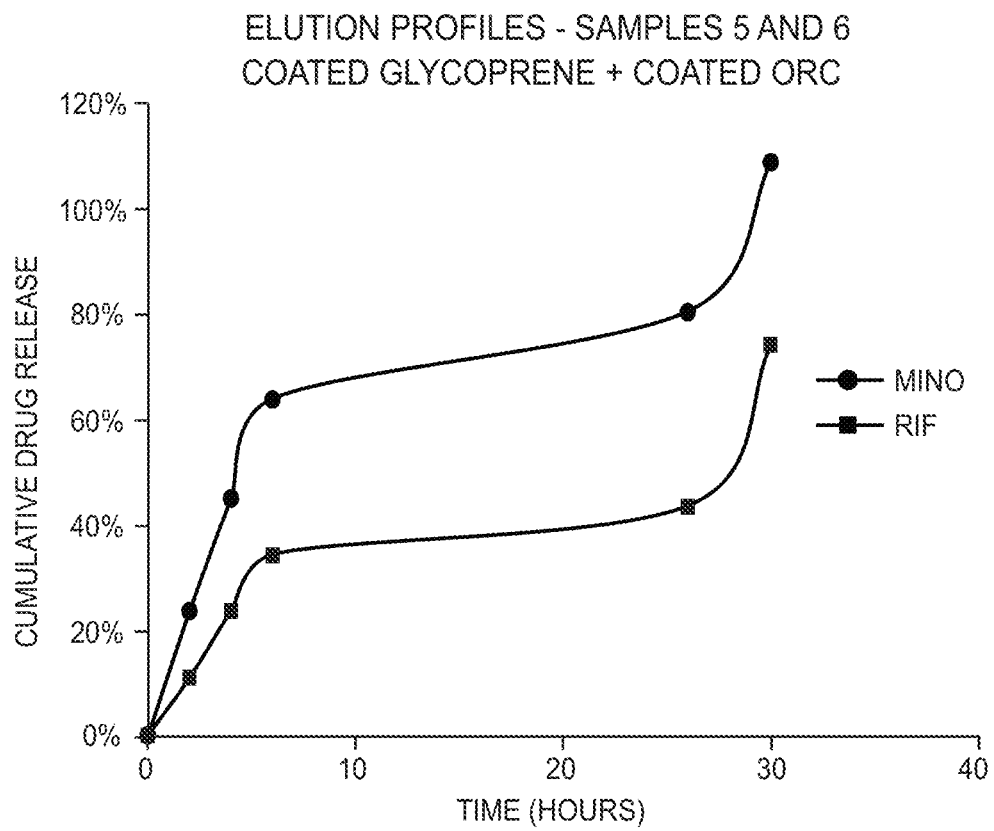
FIG. 19C is a graph showing elution profiles of Samples 5 and 6 discussed in Example 13.
Figure 19D:
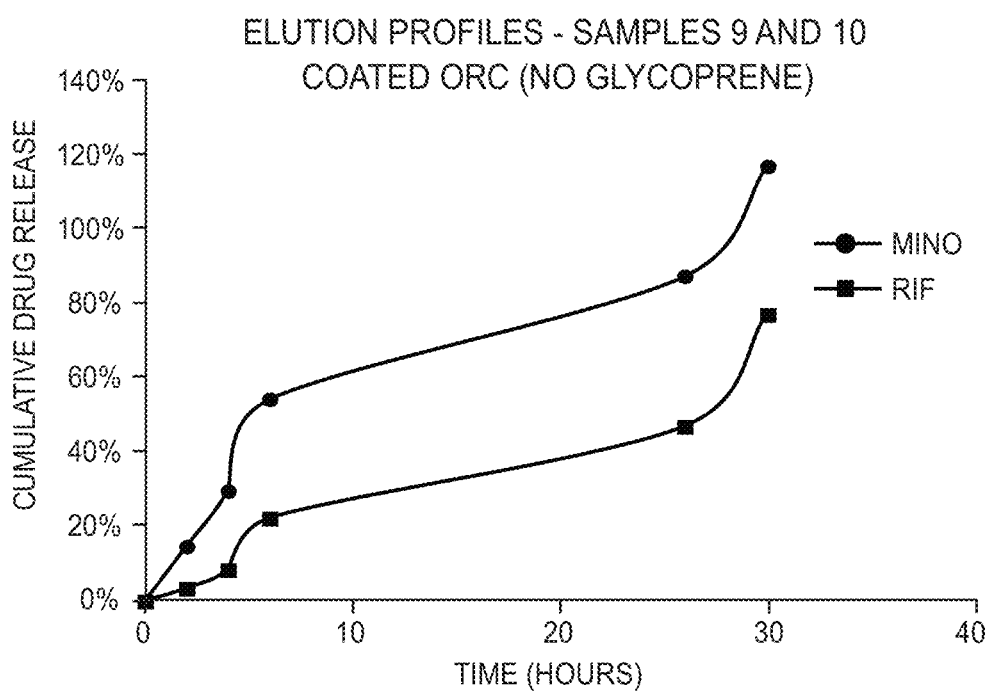
FIG. 19D is a graph showing elution profiles of Samples 9 and 10 discussed in Example 13.
Figure 19E:
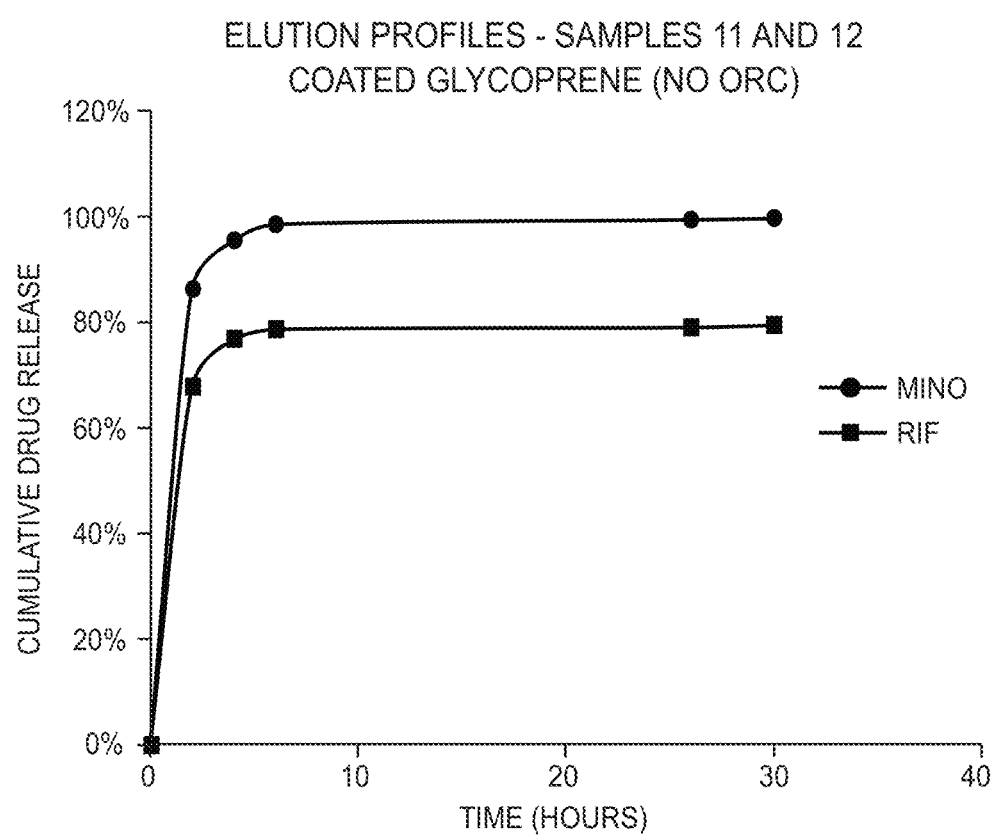
FIG. 19E is a graph showing elution profiles of Samples 11 and 12 discussed in Example 13.
Figure 19L:
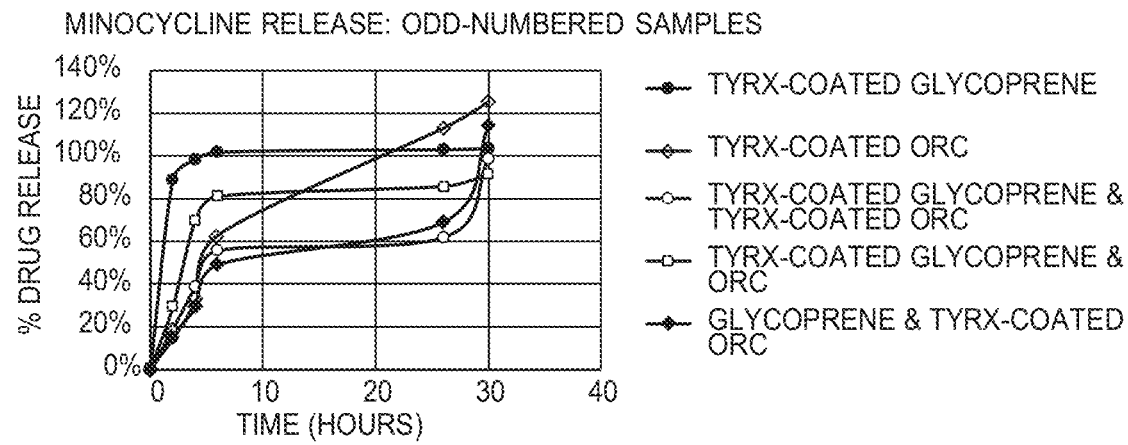
FIG. 19L includes a graph showing drug release profiles for samples discussed in Example 13.
Figure 19M:
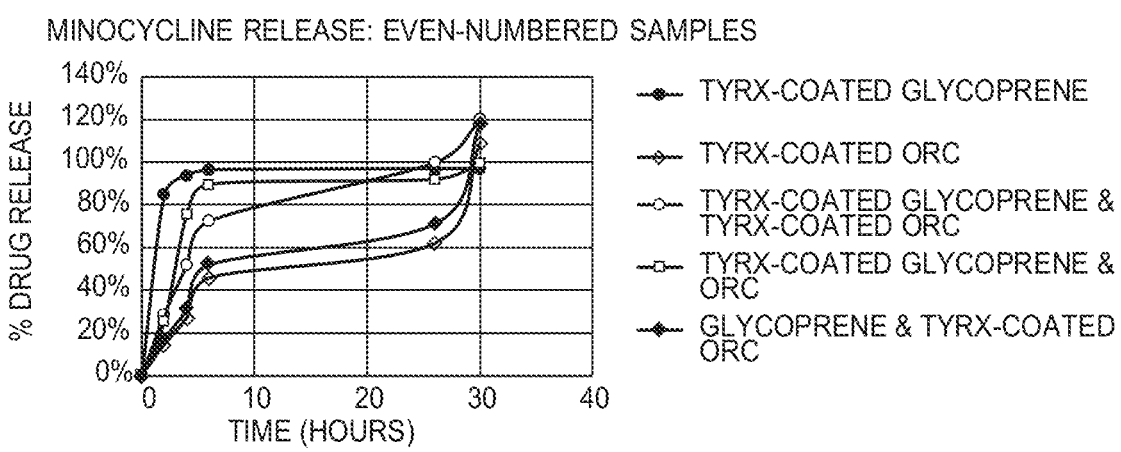
FIG. 19M includes a graph showing drug release profiles for samples discussed in Example 13.
Figure 19N:
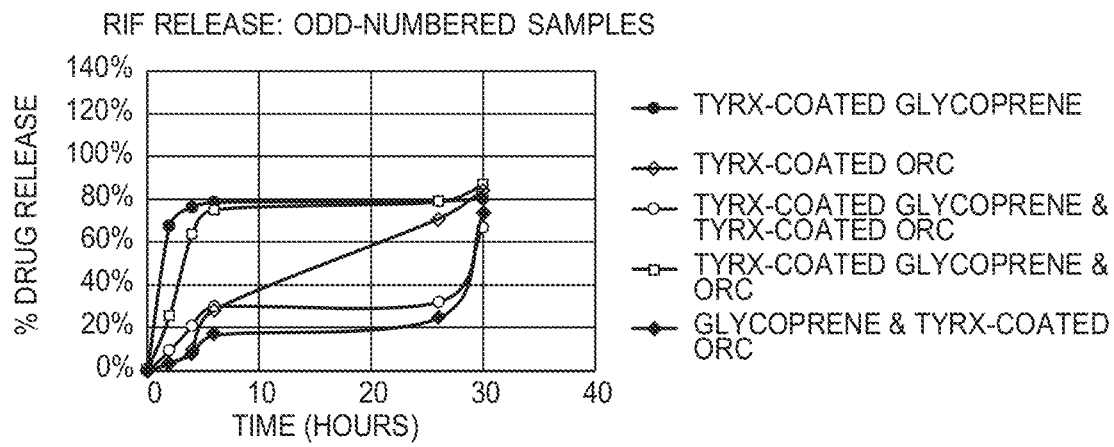
FIG. 19N includes a graph showing drug release profiles for samples discussed in Example 13.
Figure 19O:
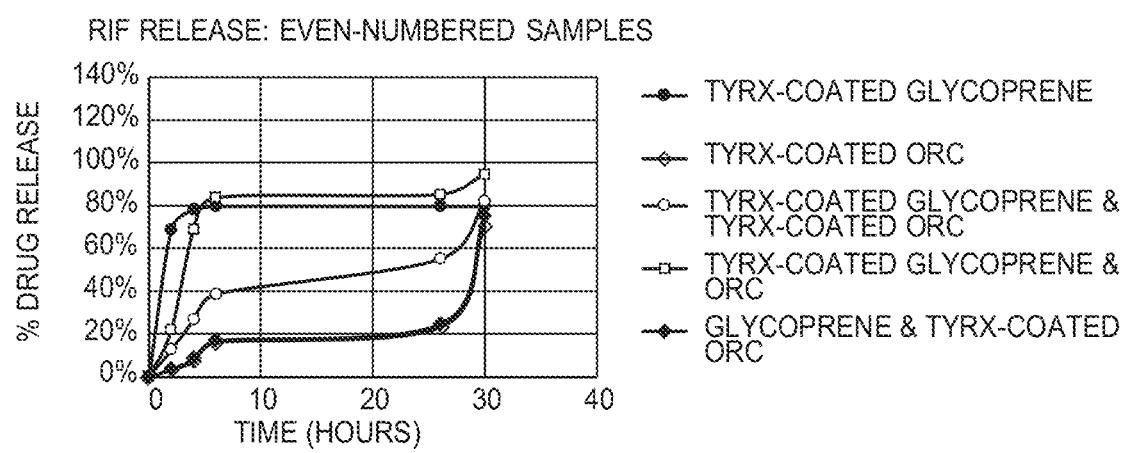
FIG. 19O includes a graph showing drug release profiles for samples discussed in Example 13.
Figure 19P:
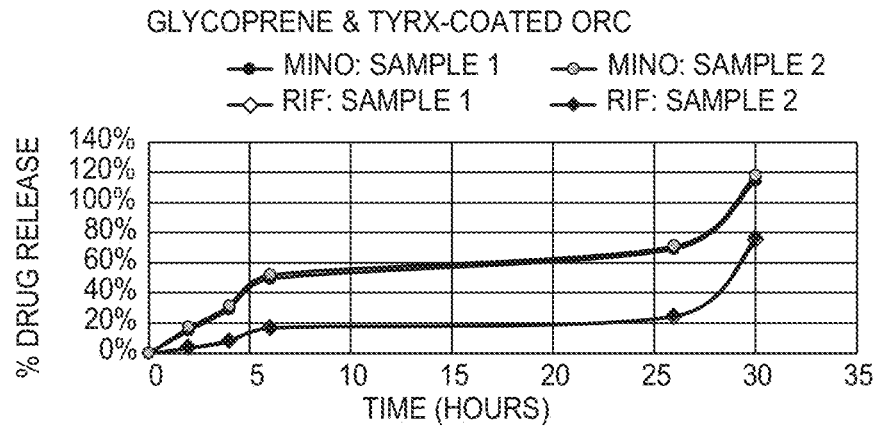
FIG. 19P includes a graph showing drug release profiles for samples discussed in Example 13.
Figure 19Q:
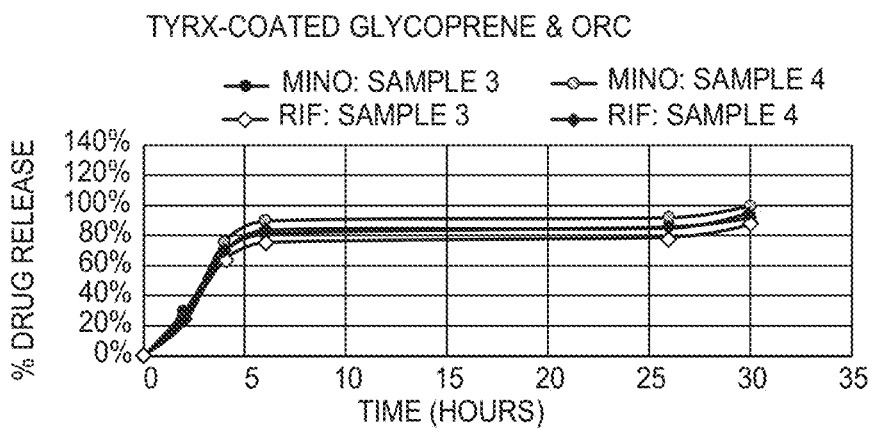
FIG. 19Q includes a graph showing drug release profiles for samples discussed in Example 13.
Figure 19R:
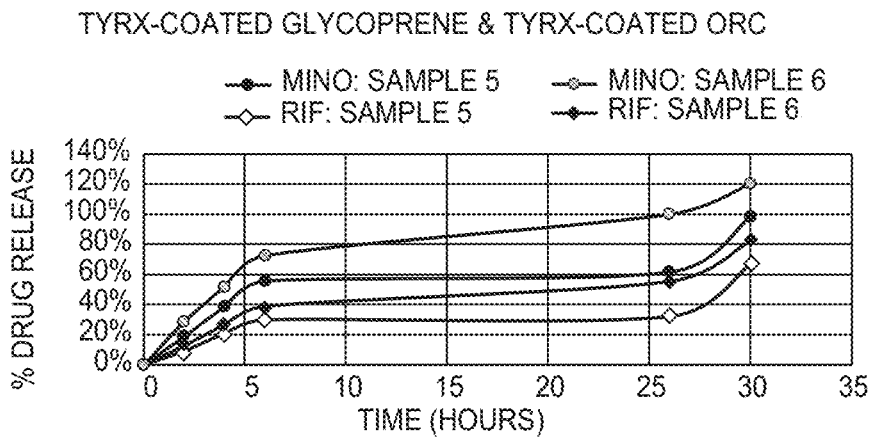
FIG. 19R includes a graph showing drug release profiles for samples discussed in Example 13.
Figure 19S:
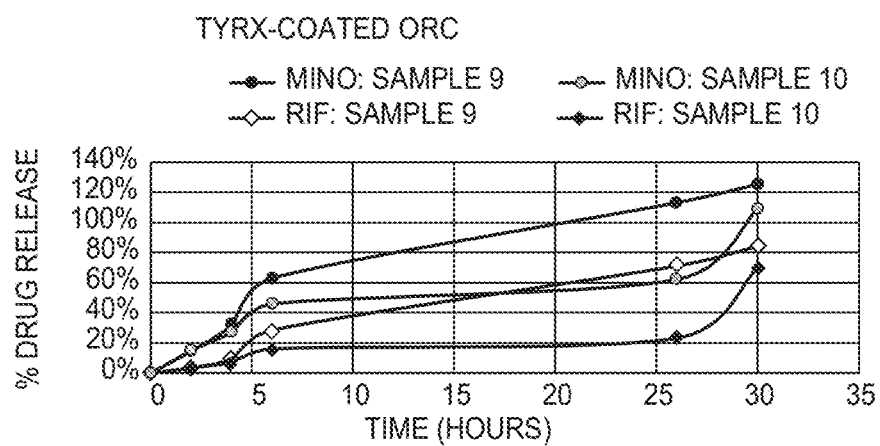
FIG. 19S includes a graph showing drug release profiles for samples discussed in Example 13.
Figure 19T:
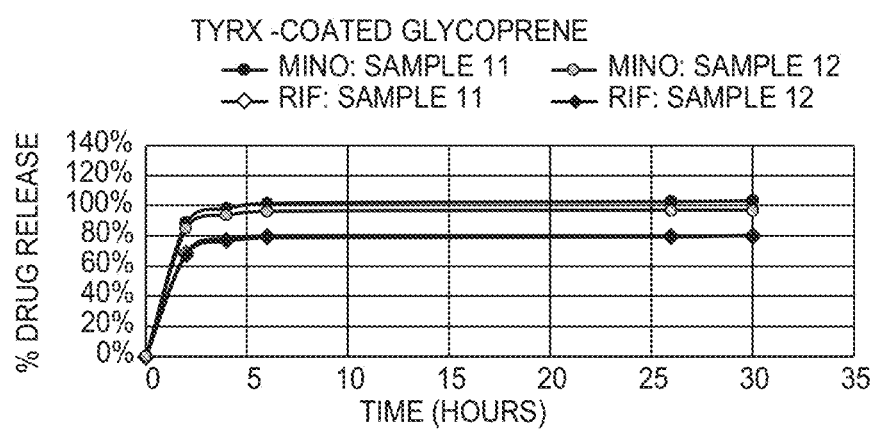
FIG. 19T includes a graph showing drug release profiles for samples discussed in Example 13.

AIGIS-R refers to a resorbable mesh substrate that is coated with a polymer, such as, for example, one of the tyrosine-derived polymers discussed herein, wherein the polymer includes at least one active pharmaceutical ingredient, as shown below. In the samples that include Glycoprene®, the Glycoprene® is a mesh that forms the substrate. The elution rates of the active pharmaceutical ingredients in Samples 1-6 and 9-12 are shown in the elution profiles in FIGS. 19A-19T.

In this example, different substrates were examined to test and compare the elution profiles of the different substrates to determine the effect, if any, of combining polymer-coated substrates with uncoated substrates.

When uncoated Glycoprene® was added to coated ORC in samples 1 and 2, both minocycline and rifampin releases were below 20% after 2 hours. By 24 hours, minocycline release was above 60%, and rifampin release was over 20%. Minocycline and rifampin releases continued to increase between 24 and 30 hours.

With the addition of uncoated ORC to coated Glycoprene® in samples 3 and 4, more than 20% minocycline and 20% rifampin was released after 2 hours. After 6 hours, minocycline release was over 80% while rifampin release was over 60%.

Samples 5 and 6 consisted of both coated Glycoprene® and coated ORC. After 2 hours, minocycline release was over 20% while rifampin release was around 50%. By 6 hours, more than 60% of minocycline was released, and more than 20% of rifampin was released. After 24 hours, rifampin release was approximately 40% while minocycline release was over 70%. Minocycline and rifampin releases continued to increase between 24 and 30 hours.

Minocycline and rifampin elution from samples 9 and 10 (coated ORC) was below 20% after 2 hours. After 24 hours, minocycline release was over 60%, while rifampin release was over 20%. Minocycline and rifampin releases continued to increase between 24 and 30 hours.

For samples 11 and 12 of coated Glycoprene®, more than 80% minocycline and more than 60% rifampin was released in 2 hours. Minocycline and rifampin release rate gradually increased until it leveled off after 6 hours.

In samples 1-6 and 9-10 after 2 hours immersion in PBS, the ORC component can be visually observed to be swollen.

Example 14

Figure 20:
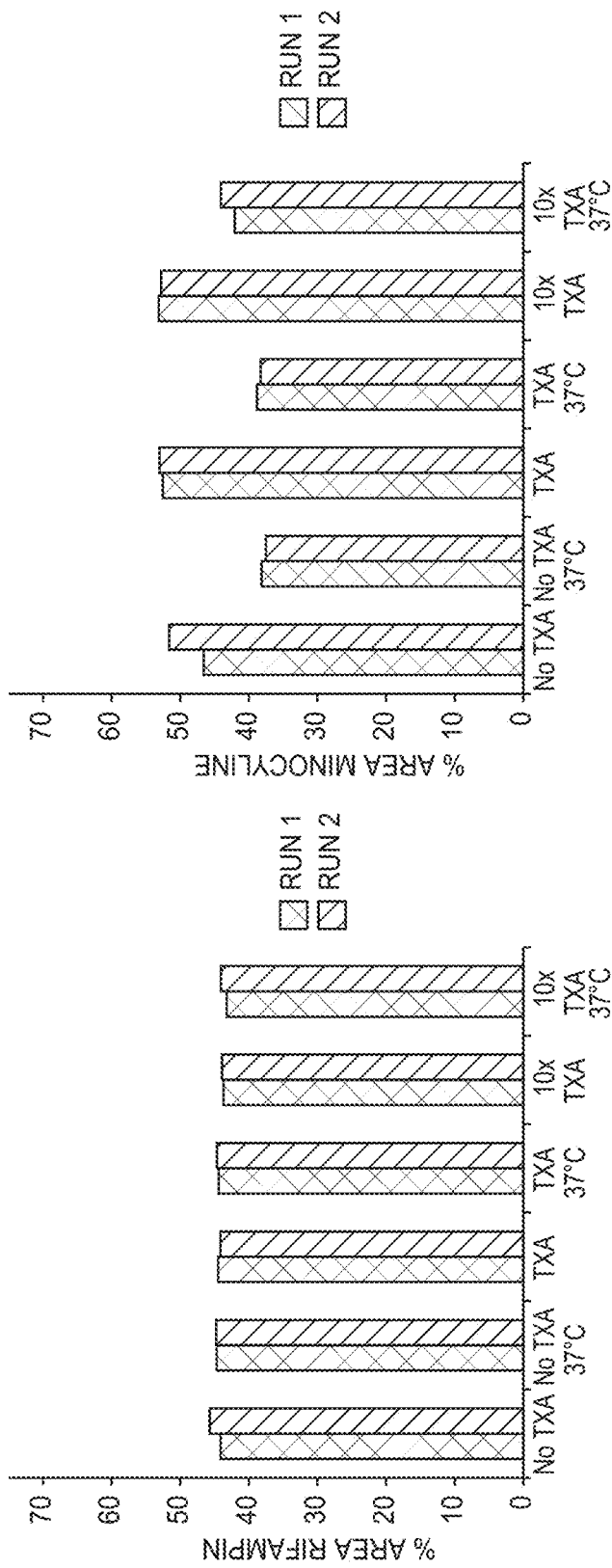
FIG. 20 includes graphs showing results discussed in Example 14.

To determine the stability of active pharmaceutical ingredients, such as, for example, one or more of active pharmaceutical ingredients 26 when combined with a hemostatic agent, such as, for example, one or more of hemostatic agents 24, mixtures of rifampin and minocycline were prepared in phosphate-buffered saline (PBS) with and without tranexamic acid (TXA). The mixtures were tested both at room temperature (RT) (about 23° C.) and at 37° C. As shown in FIG. 20, mixtures of rifampin and minocycline in PBS with and without tranexamic acid have substantially the same percentage area of rifampin and minocycline, thus indicating that tranexamic acid does not negatively affect the stability of rifampin and minocycline. In particular, the percentage area of rifampin was substantially the same for mixtures of rifampin and minocycline in PBS with and without tranexamic acid, regardless of the temperature; the percentage area minocycline was substantially the same for mixtures of rifampin and minocycline in PBS with and without tranexamic acid when the mixtures were at the same temperature.

Example 15

Figure 21:
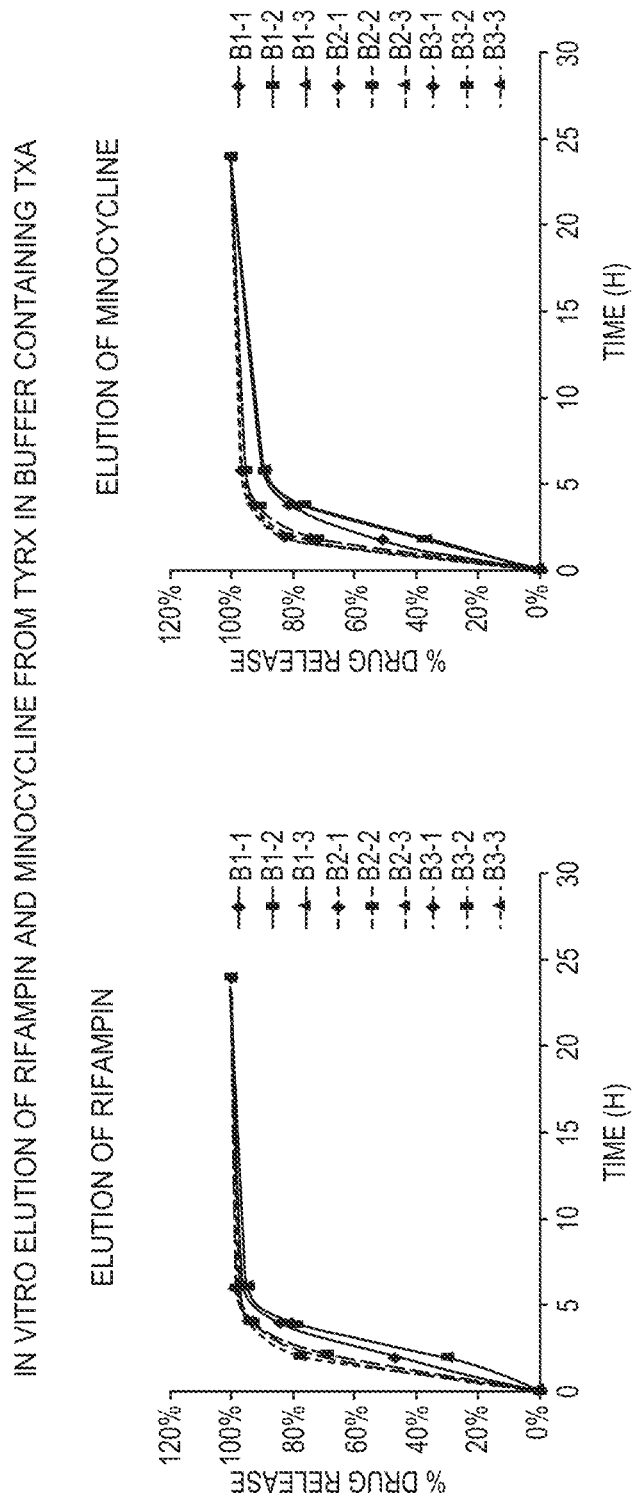
FIG. 21 includes graphs showing results discussed in Example 15.

To determine the elution of active pharmaceutical ingredients, such as, for example, one or more of active pharmaceutical ingredients 26 from a polymer, such as, for example, one of the polymers discussed herein, in vitro when the active pharmaceutical ingredients are combined with a hemostatic agent, such as, for example, one or more of hemostatic agents 24, in vitro elution of rifampin and minocycline from polymers in the p22-27.5 family containing different amounts of tranexamic acid was evaluated in a PBS buffer over 25 hours. B1=PBS pH 7.4; B2=PBS, pH 7.4+TXA (0.05 mg/mL); B3=PBS, pH 7.4+TXA (5 mg/mL). The elution rates for rifampin and minocycline are shown in FIG. 21. As shown in FIG. 21, the elution rates of rifampin and minocycline were not affected by the presence of TXA in the release media.

Example 16

Figure 22:
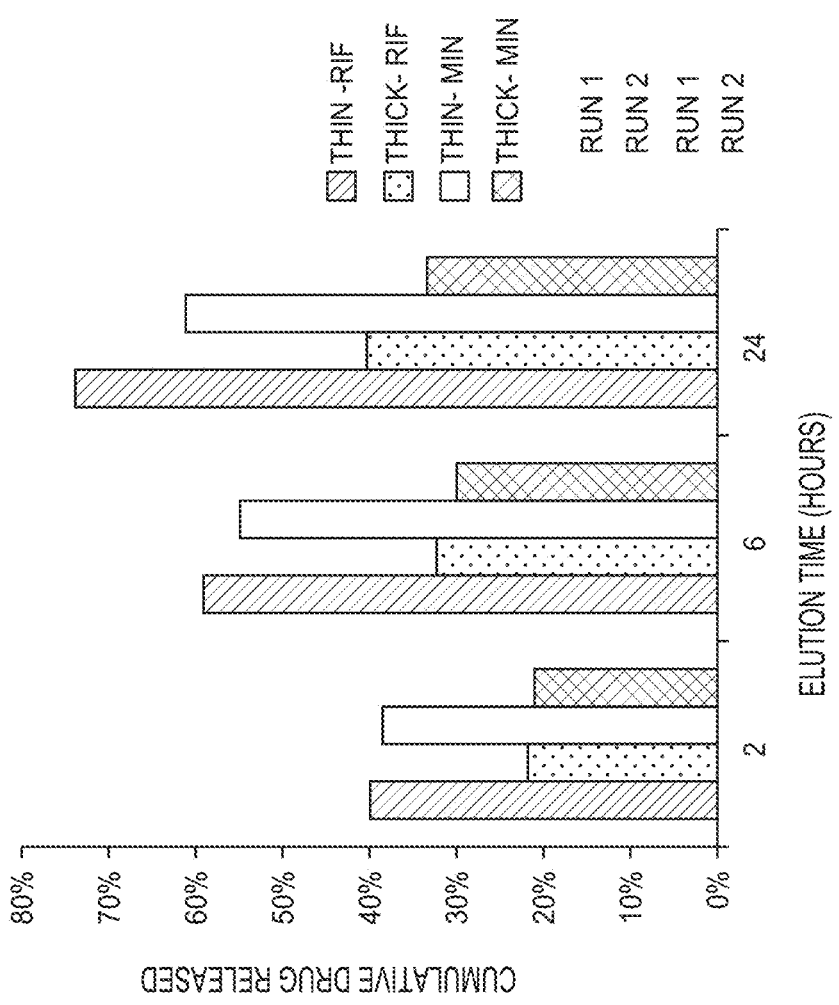
FIG. 22 is a graph showing results discussed in Example 16.

To determine the sustained release of active pharmaceutical ingredients, such as, for example, one or more of active pharmaceutical ingredients 26 from a polymer, such as, for example, one of the polymers discussed herein, when the active pharmaceutical ingredients are combined with a hemostatic agent, such as, for example, one or more of hemostatic agents 24, thin and thick solvent cast films containing rifampin (Rif) and tranexamic acid were prepared. Thin and thick solvent cast films containing minocycline (Min) and tranexamic acid were also prepared. The tranexamic acid phase was separated in each of the films. Thin films had a thickness of about 30 microns and thick films had a thickness of about 400 microns. Elution of rifampin and minocycline was measured over about 30 hours. The percentage of rifampin and minocycline released at 2 hours, 6 hours and 24 hours was recorded. As shown in FIG. 22, the thin films released rifampin and minocycline more quickly than the thick films at the same time intervals. However, for each set of films (thick and thin), rifampin and minocycline were shown to elute at similar rates.

Example 17

Figures 23, 24:
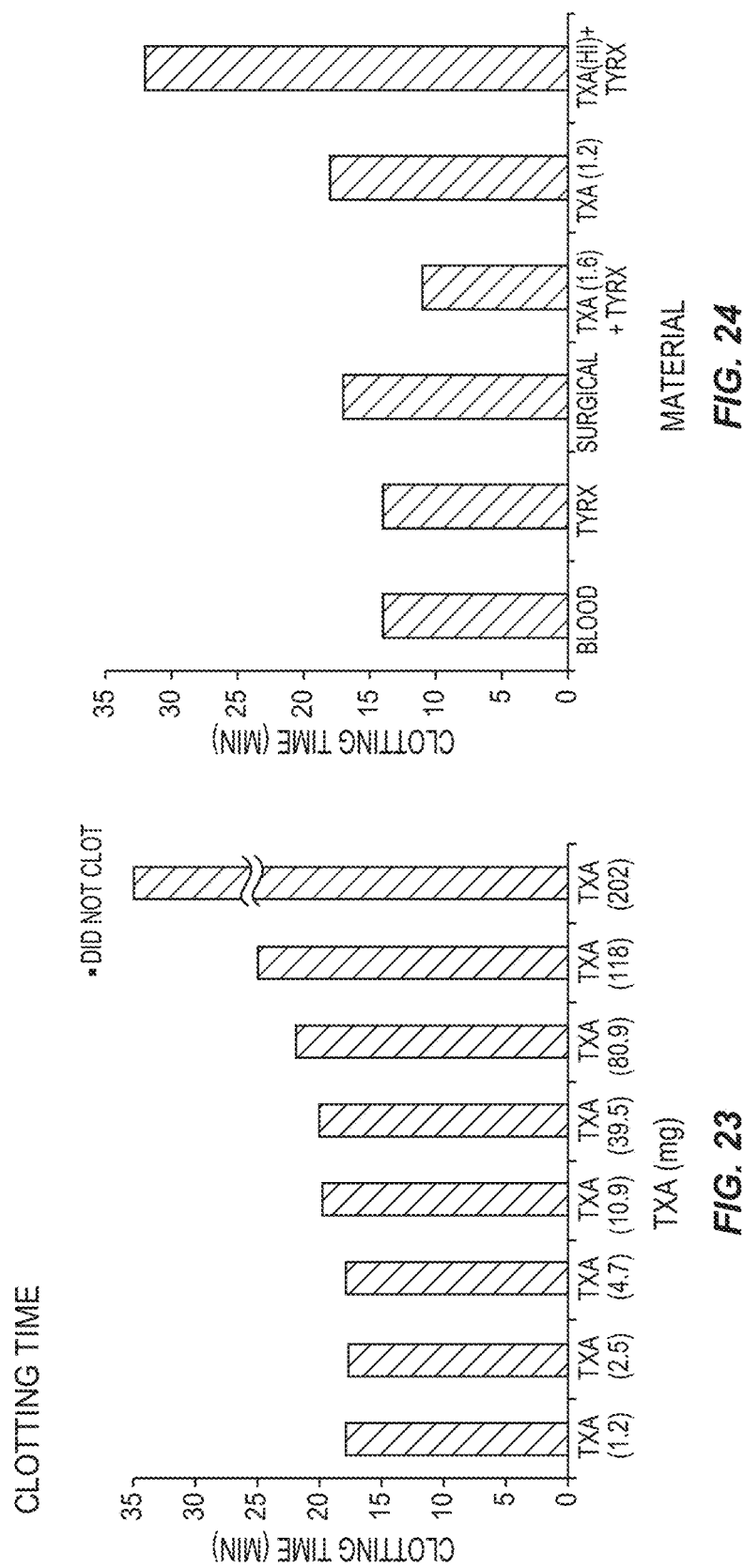
FIG. 23 is a graph showing results discussed in Example 17.
FIG. 24 is a graph showing results discussed in Example 18.
Figure 28:
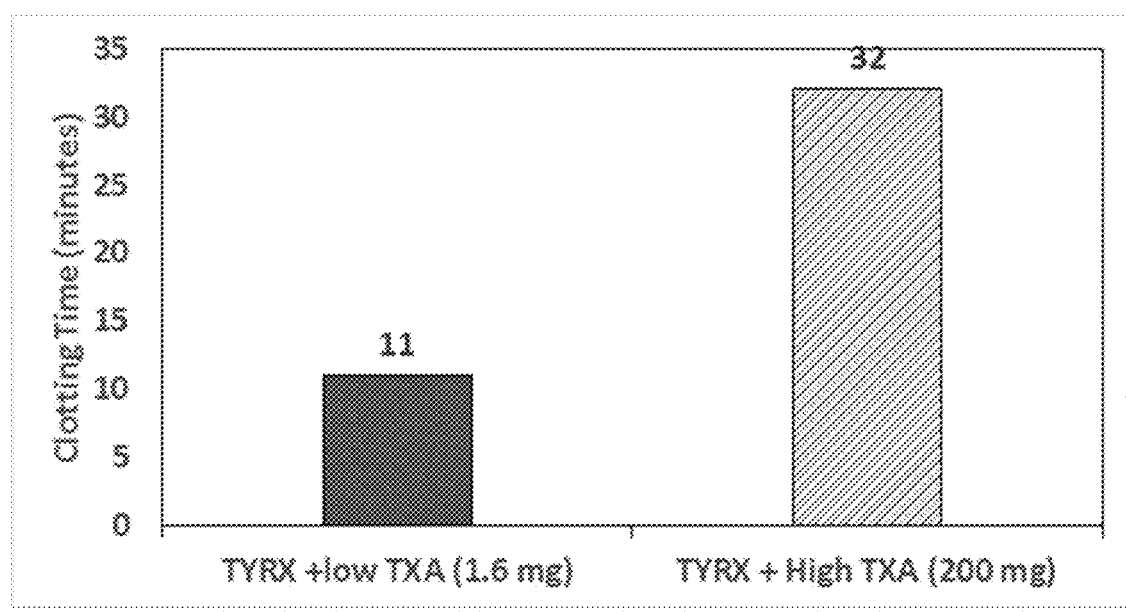
FIG. 28 includes a table showing results discussed in Example 17.

Tests were conducted to compare the time required to induce blood clotting in vitro when different amounts of hemostatic agent is administered in the presence of TYRX (degradable mesh coated with P22-27.5 containing rifampin and minocycline), as shown in FIG. 23. Clotting time was increased when higher amounts of TXA was present (1.6 mg TXA vs 200 mg of TXA), as shown in FIG. 28.

Example 18

Tests were conducted to compare the time required for different hemostatic agents to induce blood clotting in vitro versus the time required to induce blood clotting in vitro when no hemostatic agent is administered. In particular, the time required to induce blood clotting was plotted for blood alone, TYRX, Surgicel, TYRX with 1.6 mg of TXA, 1.2 mg of TXA alone and TYRX with 200 mg of TXA. In this example, TYRX refers to a Glycoprene mesh that is coated with P22-27.5 (a polymer in the P22-X family) containing Rifampin and Minocycline. As shown in FIG. 24, blood alone and TYRX were both effective to induce blood clotting in about 14 minutes; Surgicel was effective to induce blood clotting in about 17 minutes; TYRX with 1.6 mg of TXA was effective to induce blood clotting in about 12 minutes; 1.2 mg of TXA alone was effective to induce blood clotting in about 19 minutes; and the p22-27.5 polymer having 200 mg of TXA was effective to induce blood clotting in about 32 minutes, thus indicating that TYRX with low amount of TXA (1.6 mg) may induce blood clotting better than TYRX with 200 mg TXA.

Example 19

To determine the impact, if any, of a hemostatic agent, such as, for example, one or more of hemostatic agents 24 on bacterial attachment, three samples were prepared. The first sample included a TYRX polymer in the p22-xx family (P22-27.5-TYRX); the second sample included TYRX and tranexamic acid (TYRX+TXA); and the third sample included an extracellular matrix (ECM) to be used as a control. In this example, TYRX refers to a glycoprene mesh that is coated with P22-27.5 (a polymer in the P22-X family) containing rifampin and minocylcline. The samples were each suspended in 3 mL of a Brain Heart Infusion (BHI) medium at 37° C. for 24 hours. The samples were each inoculated with 2×Colony Forming Units (CFU)/mL of a clinical strain of Methicillin-resistant *Staphylococcus aureus* (MRSA). After 24 hours, each of the samples was rinsed twice and bacterial attachment was visualized by Live/Dead staining and imaged with Leica DM RXE microscope attached to a TCS SP2 AOBS confocal system (Leica Microsystems, Exton, Pa.). As shown in FIG. 25, the TYRX and TYRX+TXA samples exhibited less bacterial attachment, with the TYRX+TXA sample exhibiting less bacterial attachment than the TYRX sample.

Example 20

Chitosan Solutions for Preparing Films 1 gram of Chitosan (Sigma) was added to 100 mL of Aqueous Acetic acid (1% Acetic acid). The mixture was stirred using a magnetic stir bar until no solids remained.

Films were cast by pouring on 10 mL of the chitosan solution onto a TEFLON sheet. The solution was covered with a Petridish dried in a ventilated hood 24 hrs. The Petridish was removed and the films dried for an addition 72 hrs. A transparent film was obtained.

50 mg of Tranexamic acid was added to 10 g of the chitosan solution prepared as described above in a 20-mL scintillation vial. The vial was capped and placed on a shaker. The contents were shaken for 1 hr, when all the TXA had dissolved.

Films were cast by pouring on to a TEFLON sheet. The solution was covered with a Petridish dried in a ventilated hood 24 hrs. The Petridish was removed and the films dried for an addition 72 hrs. A transparent film was obtained.

50 mg of Tranexamic acid, 50 mg of Rifampin, 50 mg of Minocycline.HCL was added to 10 g of the chitosan solution prepared as described above in a 20-mL scintillation vial. The vial was capped and placed on a shaker. The contents were shaken for 1 hr, when all the drugs had had dissolved.

Films were cast by pouring on to a TEFLON sheet. The solution was covered with a Petridish dried in a ventilated hood 24 hrs. The Petridish was removed and the films dried for an addition 72 hrs. A transparent red film was obtained.

Two kinds of meshes were used in these experiments—a monofilament mesh of polypropylene (non-absorbable) and a multifilament absorbable mesh (GLYCOPRENE II), which is made from glycolide, caprolactone and trimethylene carbonate.

Strips of mesh approximately 1 cm×3 cm were hand dipped into the solutions of chitosan, Chitosan+Tranexamic acid and Chitosan+Tranexamic acid+Rifampin+Minocycline. HCl. These solutions were prepared as described above. Excess solution was removed using Kim wipes and wet strips were hung to dry in a hood. The coated meshes were dry to the touch after overnight drying.

Example 21

Avoiding Crystallization in Films

To assess how to avoid crystallization in films, four samples were prepared—sample J, sample L, sample B2 and sample F2. Sample J includes a polymer in the p22-xx family (P22-27.5-TYRX), rifampin, minocycline and tranexamic acid. Sample L includes a polymer in the p22-xx family (P22-27.5-TYRX), rifampin, minocycline, tranexamic acid and water. Sample B2 includes a polymer in the p22-xx family (P22-27.5-TYRX) and tranexamic acid. Sample F2 includes a polymer in the p22-xx family (P22-27.5-TYRX), tranexamic acid and water.

The samples were imaged using a digital microscope under a variety of illumination conditions and magnifications of 50×, 100×, and 200×. Transmitted crossed-polarized illumination highlighted anisotropic, apparently crystalline features in several films, as shown in FIG. 26.

Transmitted crossed-polarized illumination highlighted anisotropic, apparently crystalline features in films containing TXA. However, the apparently crystalline features were not observed in sample F2 or sample L, as shown in FIG. 26. Both of these samples were made with 1 mL aqueous TXA.

Example 22

Preparation of Electrospun Mats

Some of the properties of electro spun fibers are their high surface area, inherent 3 dimensional features and tunable porosity. In electro spinning, a thin stream of charged polymer solution is ejected from a spinneret in the presence of a high electric field (in the range of 105 to 106 V/m) applied between a conducting collector and the spinneret. Due to the application of electrostatic potential, the jet will stretch and whip around along with solvent evaporation because of the columbic repulsion between the surface charges. The resulting mass of fine fiber (nanofibers) is then collected on the target electrodes.

This technique can be used to molecules within the fiber matrix. If the drug is soluble in the polymer solution, then the drugs will be homogeneously distributed (dissolved) within the fiber. If however, the drug particles are not soluble in the polymer matrix, then the insoluble particles will be entrapped within the fiber matrix.

This technique can therefore be used to encapsulate water soluble active pharmaceutical ingredients and/or hemostatic agents (such as, for example tranexamic acid, peptides, proteins) which have poor solubility in organic solvents. Typically, a solution of the organic soluble active pharmaceutical ingredients and/or hemostatic agents with a particle size of less than 100 microns are suspended in an organic solution of a polymer and subjected to the electrospinning process, resulting in matrix of polymer fibers containing particles of drug. This technique is useful since high payloads of drugs can be incorporated into the substrate. The polymer solution may optionally contain other organic soluble compounds, including active pharmaceutical ingredients and/or hemostatic agents. More than one organic insoluble compound can be suspended in the polymer solution.

For example, the organic solution may be mixture of P22-27.5+Rifampin (10% w/w relative to polymer) and Minocycline (10% w/w relative to polymer) dissolved in a 9:1 mixture of THF: Methanol. 10% of fine powder of TXA (10% W/W relative to polymer) may be suspended in this solution and subjected to electrospray. The resulting nanofiber mat would therefore contain 10% each of Rifampin and Minocycline dissolved in the fibers and 10% TXA entrapped between fibers.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical system comprising:
an implantable medical device; and
a customizable anchorage device configured for anchoring the implantable medical device within a patient's body, the anchorage device comprising:
a substrate extending along a longitudinal axis between a first end comprising a first bonding area and an opposite second end comprising a second bonding area that is spaced apart from the first bonding area by a first non-bonding area, the first bonding area defining a first portion of a perimeter of the substrate, the second bonding area defining an opposite second portion of the perimeter, the substrate comprising a third bonding area between the first and second bonding areas, the third bonding area being spaced apart from the second bonding area by a second non-binding area, the non-bonding areas including a first composition, the bonding areas including a second composition that is different than the first composition,
wherein a hemostatic agent is applied to the substrate via a polymer, the polymer comprising an antibiotic and the hemostatic agent, the polymer being configured to elute the antibiotic and the hemostatic agent as the polymer degrades, and
wherein the substrate is configured to be folded along the longitudinal axis such that first portions of the bonding areas engage second portions of the bonding areas.

2. The surgical system recited in claim 1, wherein the bonding areas each include an adhesive and a nonstick material that covers the adhesive.

3. The surgical system recited in claim 1, wherein:
the bonding areas each include an adhesive and a removable nonstick material that covers the adhesive;
first sections of the adhesives of the first and second bonding areas engage second sections of the adhesives of the first and second bonding areas when the first portions of the first and second bonding areas engage the second portions of the first and second bonding areas; and
a first section of the nonstick material of the third bonding area engages a second section of the nonstick material of the third bonding area when the first portion of the third bonding area engages the second portion of the third bonding area.

4. The surgical system recited in claim 1, wherein:
the bonding areas each include an adhesive and a removable nonstick material that covers the adhesive;
first sections of the adhesives of the first and third bonding areas engage second sections of the adhesives of the first and third bonding areas when the first portions of the first and third bonding areas engage the second portions of the first and third bonding areas; and
a first section of the nonstick material of the second bonding area engages a second section of the nonstick material of the second bonding area when the first portion of the second bonding area engages the second portion of the second bonding area.

5. The surgical system recited in claim 1, wherein the hemostatic agent comprises tranexamic acid.

6. The surgical system recited in claim 1, wherein the substrate is a mesh substrate.

7. The surgical system recited in claim 1, wherein the antibiotic is selected from a group consisting of rifampin and minocycline and mixtures thereof.

8. The surgical system recited in claim 1, wherein the polymer is a polyarylate.

9. The surgical system recited in claim 1, wherein the polymer is member of the P22-xx family.

10. A surgical system comprising:
an implantable medical device; and
a customizable anchorage device configured for anchoring the implantable medical device within a patient's body, the anchorage device comprising:

a substrate extending along a longitudinal axis between a first end comprising a first bonding area and an opposite second end comprising a second bonding area that is spaced apart from the first bonding area by a first non-bonding area, the first bonding area defining a first portion of a perimeter of the substrate, the second bonding area defining an opposite second portion of the perimeter, the substrate comprising a plurality of spaced apart bonding areas between the first and second bonding areas, the plurality of spaced apart bonding areas each being spaced apart from the first bonding area and the second bonding area by a second non-bonding area, the non-bonding areas including a first composition, the bonding areas including a second composition that is different than the first composition, wherein a hemostatic agent is applied to the non-bonding areas via a polymer, the polymer comprising an antibiotic and the hemostatic agent, the polymer being configured to elute the antibiotic and the hemostatic agent as the polymer degrades.

11. The surgical system recited in claim 10, wherein the plurality of spaced apart bonding areas comprises third and fourth bonding areas.

12. The surgical system recited in claim 10, wherein the substrate is configured to be folded along the longitudinal axis such that first portions of the bonding areas engages second portions of the bonding areas.

13. The surgical system recited in claim 10, wherein the bonding areas each include an adhesive and a nonstick material that covers the adhesive.

14. The surgical system recited in claim 10, wherein:
the bonding areas each include an adhesive and a removable nonstick material that covers the adhesive;
first sections of the adhesives of the first and second bonding areas engage second sections of the adhesives of the first and second bonding areas when the first portions of the first and second bonding areas engage the second portions of the first and second bonding areas; and
first sections of the nonstick materials of the third and fourth bonding areas engage second sections of the nonstick materials of the third and fourth bonding areas when the first portions of the third and fourth bonding areas engage the second portions of the third and fourth bonding areas.

15. The surgical system recited in claim 10, wherein:
the bonding areas each include an adhesive and a removable nonstick material that covers the adhesive;

first sections of the adhesives of the first and third bonding areas engage second sections of the adhesives of the first and third bonding areas when the first portions of the first and third bonding areas engage the second portions of the first and third bonding areas; and
first sections of the nonstick materials of the second and fourth bonding areas engage second sections of the nonstick materials of the second and fourth bonding areas when the first portions of the second and fourth bonding areas engage the second portions of the second and fourth bonding areas.

16. A method of customizing an anchorage device comprising:
providing an anchorage device comprising a substrate extending along a longitudinal axis between a first end comprising a first bonding area and an opposite second end comprising a second bonding area that is spaced apart from the first bonding area by a first non-bonding area, the substrate comprising a plurality of spaced apart bonding areas between the first and second bonding areas, the plurality of spaced apart bonding areas each being spaced apart from the first bonding area and the second bonding area by a second non-bonding area, the non-bonding areas including a first composition, the bonding areas including a second composition that is different than the first composition, wherein a hemostatic agent is applied to at least a portion of the substrate via a polymer, the polymer comprising an antibiotic and the hemostatic agent, the polymer the antibiotic and the hemostatic agent as the polymer degrades, and wherein the bonding areas each include an adhesive and a removable nonstick material that covers the adhesive; and
folding the anchorage device along the longitudinal axis such that first portions of the bonding areas engages second portions of the bonding areas.

17. The surgical system recited in claim 1, wherein the substrate comprises opposite first and second sides, the polymer being applied to each of the first and second sides.

18. The surgical system recited in claim 1, wherein the substrate comprises opposite first and second sides, the polymer completely coating at least one of the first and second sides.

19. The surgical system recited in claim 1, wherein the second composition includes an adhesive and the first composition is free of adhesives.

* * * * *